United States Patent [19]
Hadary et al.

[11] Patent Number: 5,616,485
[45] Date of Patent: Apr. 1, 1997

[54] STREPTOMYCES PROTEASES AND IMPROVED STREPTOMYCES STRAINS FOR EXPRESSION OF PEPTIDES AND POLYPEPTIDES

[75] Inventors: Dany Hadary, Richmond Hill; Daniel Bartfeld, North York; Michael J. Butler, Beeton; David Jenish, Mississauga; Timothy Krieger, Brampton; Lawrence T. Malek, Brampton; Gisela Soostmeyer, Kleinburg; Eva Walcyzk, Mississauga, all of Canada

[73] Assignee: Cangene Corporation, Mississauga, Canada

[21] Appl. No.: 173,508

[22] Filed: Dec. 23, 1993

[51] Int. Cl.$^6$ .............. C12N 9/52; C12N 15/31; C12N 15/57; C12N 15/76
[52] U.S. Cl. .............. 435/220; 435/69.1; 435/252.35; 435/320.1; 435/172.3; 536/23.2; 536/23.7; 935/10; 935/14; 935/29; 935/75
[58] Field of Search .............. 435/220, 252.35, 435/69.1; 536/23.2

[56] References Cited

U.S. PATENT DOCUMENTS

| | | | |
|---|---|---|---|
| 4,652,639 | 3/1987 | Stabinsky | 536/27 |
| 5,200,327 | 4/1993 | Garvia et al. | 435/69.5 |

FOREIGN PATENT DOCUMENTS

| | | | |
|---|---|---|---|
| 1295566 | 4/1992 | Canada . | |
| 0300466 | 1/1989 | European Pat. Off. | 536/23.2 |
| 93-05532 | 6/1992 | WIPO | 435/220 |
| WO92/18842 | 10/1992 | WIPO . | |
| 92-16642 | 10/1993 | WIPO | 435/252.31 |
| 93-23530 | 11/1993 | WIPO | 435/220 |

OTHER PUBLICATIONS

Atlan, D., et al., "Isolation and Characterization of Aminopeptidase–Deficient *Lactobacillus bulgaricus* Mutants" *Applied and Environmental Microbiology*, 55(7): 1717–1723 (Jul. 1988).

Alvaraz, N. G., et al., "Purification and characterization of a thermosensitive X–prolyl dipeptidyl aminopeptidase (dipeptidyl aminopeptidase ysov) . . . ", *Biochimica et Biophysica Acta* 632: 119–125 (1985).

Aretz, W., et al., "Proteolytic enzymes from recombinant *Streptomyces lividens* TK24", *FEMS Microbiology Letters* 65; 31–36 (1989).

Balon, R., et al., "Purification, Substrate Specificity, and Classification of Tripeptidyl Peptidase II". *The Journal of Biological Chemistry*, 261(5): 2409–2417 (1986).

Bender, E., et al., "Secretory synthesis of human Interluekin-2 by *Streptomyces lividens*", *Gene*, 86: 227–232 (1990).

(List continued on next page.)

*Primary Examiner*—Robert A. Wax
*Assistant Examiner*—William W. Moore
*Attorney, Agent, or Firm*—Foley & Lardner

[57] ABSTRACT

A family of proteases endogenous to Streptomyces cells degrade heterologous proteins secreted from Streptomyces host cells. The previously unidentified proteases include (1) tripeptidyl aminopeptidase—Streptomyces ("Tap"), (2) a Streptomyces protease ("Ssp") which displayed significant amino acid sequence homology to Subtilisin BPN' and showed an ability to remove tripeprides from the amino termini of proteins and peptides, and (3) other proteases derived from Streptomyces which degraded certain substrates under certain conditions. Degradation was alleviated by selective inhibition of secreted proteases or by using hosts with impaired capabilities to produce proteases. An irreversible inhibitor was designed based upon the mechanism and substrate specificity of the target protease. Hosts secreting high amounts of proteases were selected. Impaired hosts were produced by deleting or altering the nucleotide sequence for the proteases.

9 Claims, 40 Drawing Sheets

OTHER PUBLICATIONS

Bibb, M., et al., "Nucleotide sequences encoding and promoting expression of three antibiotic resistance genes Indigenous to Streptomyces", *Mol Gen Genet* 199:26–36.

Brawner, M., et al., "Expression of the Soluble CD-4 Receptor in Streptomyces", *J. Cell Biochem.*, CC036 (Abstract) 14A p. 103, (1993).

Butler, M. J., et al., "Cloning of genetic loci involved in endoprotease activity in *Stretomyces lividens* 66: a novel neutral protease gene with an adjacent divergent putative . . . ", *Can. J. Microbiol.*, 38: 812–820 (1992).

Fukasawa, et al., "Purification and Properties of Dipeptidyl Peptidase IV from *Streptocpccis mitis* ATCC 9811", *Archives of Biochemistry and Biophysics*, 210(1): 230–237 (1981).

Hanson, H., et al., "Crystalline Leucine Aminopeptidase from Lens ($\alpha$-Amino acyl–Peptide Hydrolase; EC 3,4, 11.1", *Methods Enzymol.*, 45: 504–521 (1976).

Henderson, G., et al., "Characterization and Structure of Genes for Proteases A and B from *Streptomyces griseus*", *Journal of Bacteriology*, 169(6): 3776–3764 (1987).

Hopwood, D.A., et al., *Genetic Manipulation of Streptomyces: A Laboratory Manual*, Table of Contents (1985).

Ingram, C., et al., "*xylE* Functions as an Efficient Reporter Gene in Streptomyces app.: Use for the Study of *GalP*1, a Catabolite–Controlled Promoter", *Journal of Bacteriology*, 171(12): 6617–6624 (1989).

Kreil, G., "Processing of precursors by dipeptidylaminopetidases: a case of molecular ticketing", *TIBS* 15, 23–25 (1990).

Lloyd, R.J., et al., "Characterization of X–propyl dipetidyl aminopeptidase from *Lactococcus lactis* subsp. *lactis*", *Journal of General Microbiology* 137; 45–55 (1991).

Malek, L., "Secretion of Granulocyte Macrophage–Colony Stimulating Factor (GM–CSF) in *Streptomyces lividans*", *J. Cell Biochem.*, CC412 (Abstract) 14A p. 127 (1990).

McDonald, J.K., et al., "Partial Purification and Characterization of an Ovarian Tripeptidyl Peptidase: A Lysosomal Exopeptidase . . . ", *Biochemical and Biophysical Research Communications*, 126(1): 63–71 (1985).

Menn, F. et al., "Location and sequence of the *toolF* gene encoding 2–hydroxy–6–oxohepta–2,4–dienoate hydrolase in *Pseudomonas putide* F1", *Gene*, 104: 91–94 (1991).

Taguchi, S., et al., "Efficient Extracellular Expression of a Foreign Protein in Streptomyces Using Secretory Protease Inhibitor (SSI) Gene Fusions", *Bio/Technology*, 7: 1063–1066 (1989).

Tomkinson, B., et al., "Characterization of cDNA for Human Tripeptidyl Peptidase II: The N–Terminal Part of the Enzyme is Similar to Subtilisin", *Biochemistry* 30: 168–174 (1991).

Yoshimoto, T., et al., "Cloning and Expression of Aminopeptidase Gene from *Escherichia coli* HB101 and Characterization of Expressed Enzyme", *J. Biochem* 104(1): 93–97 (1988).

Yoshimoto, T., et al., "Sequencing and High Expression of Aminopeptidase P Gene from *Escherichia coli* HB101", *J. Biochem* 105: 412–416 (1989).

Bender, E., et al., Applied Microbiology and Biotechnology, 34: 203–207.

Bibb, M. J. et al., 1984, Gene, 30: 157–166.

Fornwald, J.A., et al., 1993, Bio/Technology, 11:1031–1036.

Illingworth, C., et al. 1989, Journal of Industrial Microbiology, 4:37–42.

Lichenstein, H., et al., 1988, Journal of Bacteriology, 170: 3924–3929.

Koller, K.–P., et al., 1989, Bio/Technology, 7:1055–1059.

Schoellmann, G., et al., 1963, Biochemistry, 2:252–255.

Shaw, E., et al., 1965, Biochemistry, 4:2219–2224.

Ueda, Y., et al., 1993, Gene, 129: 129–134.

Atlan, D., et al., 1989, Applied and Environmental Microbiology, 55: 1717–1723.

Svendsen, I., et al., 1991, FEBS Letters, 292: 165–167.

Sidhu, S.S., et al., 1993, Biochemistry and Cell Biology, 71: 454–461.

Von Heijne, G., 1989, Protein Engineering, 2(4):531–534.

Fontkamp, E., et al., 1986, DNA, 5(6): 511–517.

1 2 3 4

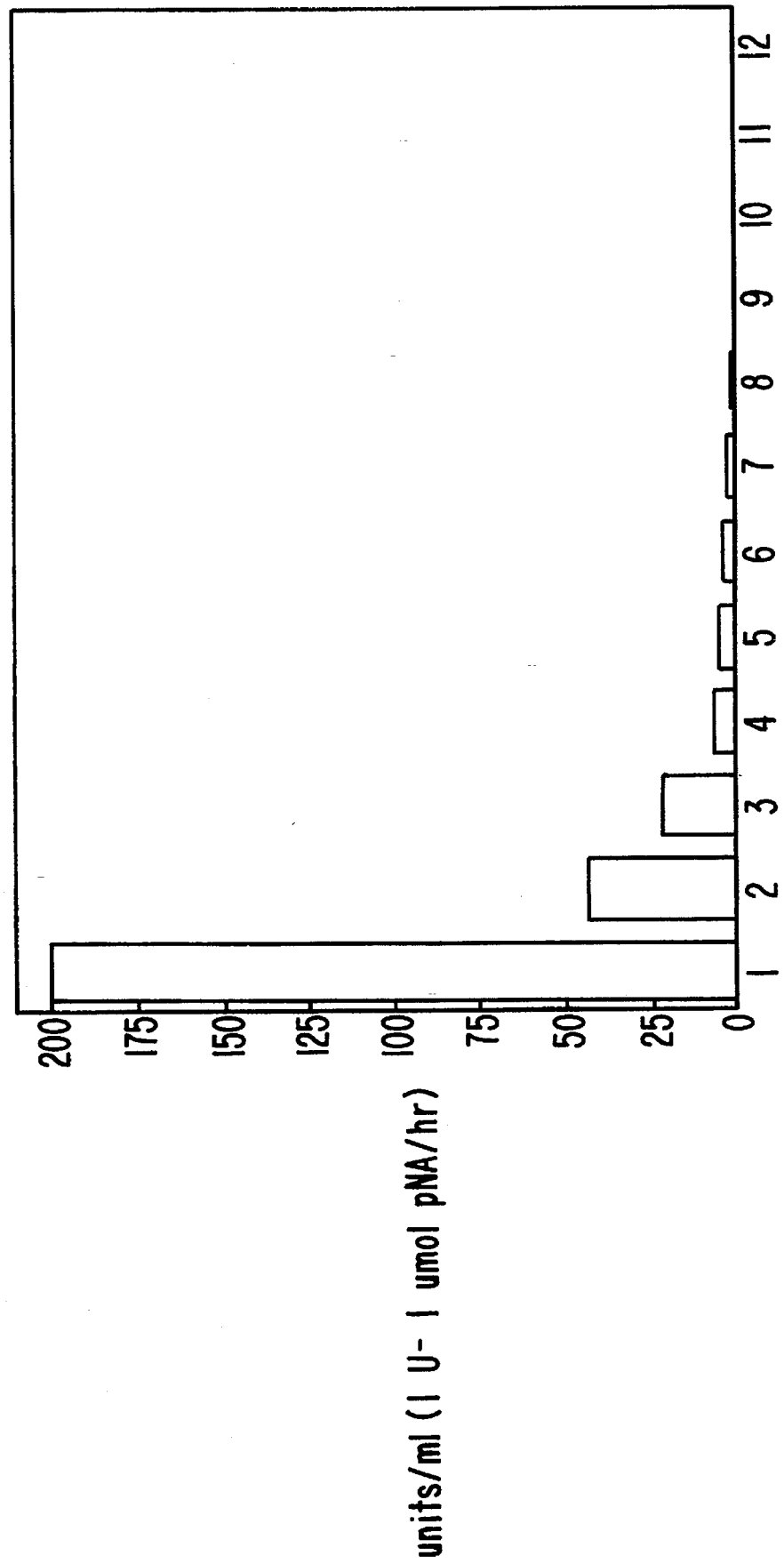

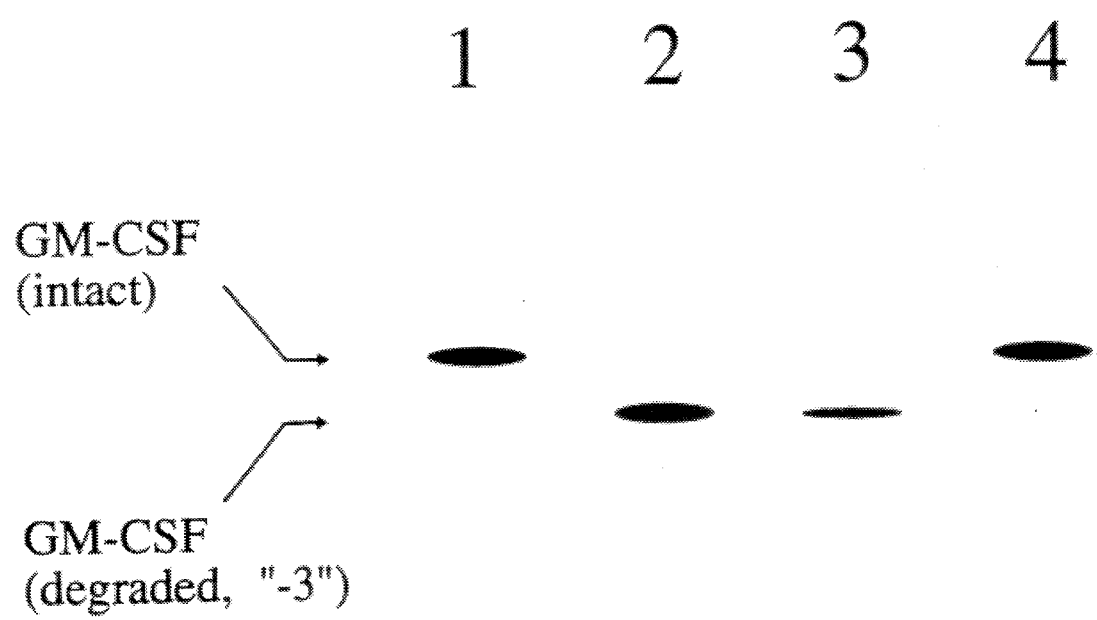

FIG. 12A

```
GGCGGGGACC GGCCGACGGC CCCGCCGAAC GAACGCCCTT CTCCGTTTAT CGGATTGGCA    60
AAGAAGTAGC ACTGGCCCTG TTCTCAGGAA ACCCACAGCG GCGAGGATCC CCGTACTTGT   120
CGCGAACACG TACGGGGAGG CCAC TTG AGG AAG AGC AGC ATA CGG CGG AGG     172
              fMet Arg Lys Ser Ser Ile Arg Arg Arg
                                -35
```

| | | | | | | | | | | | | | | | | |
|---|---|---|---|---|---|---|---|---|---|---|---|---|---|---|---|---|
| GCG | ACC | GCC | TTC | GGC | ACG | GCC | GGA | GCA | CTG | GTC | ACC | GCC | ACG | CTG | ATC | 220 |
| Ala | Thr | Ala | Phe | Gly | Thr | Ala | Gly | Ala | Leu | Val | Thr | Ala | Thr | Leu | Ile | |
| -30 | | | | -25 | | | | | -20 | | | | | | -15 | |

```
GCC GGC GCC GTC TCG GCA CCC GCC GCG AGC GCC GCC CCG GCC GAC GGC    268
Ala Gly Ala Val Ser Ala Pro Ala Ala Ser Ala Ala Pro Ala Asp Gly
            -10                  -5                       1

CAC GGG CAC GGG CGG AGC TGG GAC CGG GAG GCG CGC GGT GCC GCC ATC    316
His Gly His Gly Arg Ser Trp Asp Arg Glu Ala Arg Gly Ala Ala Ile
          5                      10                  15

GCC GCC GCC CGC GCC GCC CGG GCG GGC ATC GAC TGG GAG GAC TGC GCA    364
Ala Ala Ala Arg Ala Ala Arg Ala Gly Ile Asp Trp Glu Asp Cys Ala
    20                  25                  30

GCC GAC TGG AAC CTG CCC AAG CCC ATC CAG TGC GGC TAC GTC ACG GTG    412
Ala Asp Trp Asn Leu Pro Lys Pro Ile Gln Cys Gly Tyr Val Thr Val
35                  40                  45                  50

CCG ATG GAC TAC GCC AAG CCG TAC GGC AAG CAG ATC AGG CTC GCC GTC    460
Pro Met Asp Tyr Ala Lys Pro Tyr Gly Lys Gln Ile Arg Leu Ala Val
            55                  60                  65

GAC CGC ATC GGC AAC ACC GGA ACC AGG AGC GAG CGC CAG GGC GCC CTG    508
Asp Arg Ile Gly Asn Thr Gly Thr Arg Ser Glu Arg Gln Gly Ala Leu
            70                  75                  80

ATC TAC AAC CCC GGC GGT CCC GGC GGC TCC GGC CTG CGT TTC CCG GCC    556
Ile Tyr Asn Pro Gly Gly Pro Gly Gly Ser Gly Leu Arg Phe Pro Ala
        85                  90                  95

CGC GTC ACG AAC AAG AGC GCG GTC TGG GCC AAC ACG GCC AAG GCC TAC    604
Arg Val Thr Asn Lys Ser Ala Val Trp Ala Asn Thr Ala Lys Ala Tyr
        100                 105                 110

GAC TTC GTC GGC TTC GAC CCG CGC GGC GTC GGC CAC TCC GCG CCC ATC    652
Asp Phe Val Gly Phe Asp Pro Arg Gly Val Gly His Ser Ala Pro Ile
115                 120                 125                 130

TCC TGC GTC GAC CCG CAG GAG TTC GTC AAG GCA CCC AAG GCC GAC CCC    700
Ser Cys Val Asp Pro Gln Glu Phe Val Lys Ala Pro Lys Ala Asp Pro
                135                 140                 145

GTG CCC GGC TCC GAG GCC GAC AAG CGC GCC CAG CGC AAG CTC GCC CGC    748
Val Pro Gly Ser Glu Ala Asp Lys Arg Ala Gln Arg Lys Leu Ala Arg
            150                 155                 160

GAG TAC GCC GAG GGC TGC TTC GAG CGC AGC GGC GAG ATG CTC CCG CAC    796
Glu Tyr Ala Glu Gly Cys Phe Glu Arg Ser Gly Glu Met Leu Pro His
        165                 170                 175
```

FIG. 12B

```
ATG ACC ACG CCG AAC ACC GCG CGC GAC CTC GAC GTC ATC CGC GCC GCC    844
Met Thr Thr Pro Asn Thr Ala Arg Asp Leu Asp Val Ile Arg Ala Ala
180             185                 190

CTC GGC GAG AAG AAG CTC AAC TAC CTC GGC GTC TCC TAC GGC ACC TAC    892
Leu Gly Glu Lys Lys Leu Asn Tyr Leu Gly Val Ser Tyr Gly Thr Tyr
195             200                 205                 210

CTC GGC GCC GTC TAC GGC ACC CTC TTC CCG GAC CAC GTC CGC CGC ATG    940
Leu Gly Ala Val Tyr Gly Thr Leu Phe Pro Asp His Val Arg Arg Met
                215                 220                 225

GTC GTC GAC AGC GTC GTC AAC CCG TCC CGC GAC AAG ATC TGG TAC CAG    988
Val Val Asp Ser Val Val Asn Pro Ser Arg Asp Lys Ile Trp Tyr Gln
        230                 235                 240

GCC AAC CTG GAC CAG GAC GTC GCC TTC GAG GGC CGC TGG AAG GAC TGG   1036
Ala Asn Leu Asp Gln Asp Val Ala Phe Glu Gly Arg Trp Lys Asp Trp
            245                 250                 255

CAG GAC TGG GTC GCC GCG AAC GAC GCC GCC TAC CAC CTC GGC GAC ACC   1084
Gln Asp Trp Val Ala Ala Asn Asp Ala Ala Tyr His Leu Gly Asp Thr
260                 265                 270

CGC GCC GAG GTC CAG GAC CAG TGG CTG AAG CTG CGC GCC GCC GCC GCG   1132
Arg Ala Glu Val Gln Asp Gln Trp Leu Lys Leu Arg Ala Ala Ala Ala
275                 280                 285                 290

AAG AAG CCG CTG GGC GGC GTC GTC GGA CCG GCC GAG CTG ATC TCC TTC   1180
Lys Lys Pro Leu Gly Gly Val Val Gly Pro Ala Glu Leu Ile Ser Phe
                295                 300                 305

TTC CAG AGC GCC CCG TAC TAC GAC TCC GCC TGG GCG CCG ACC GCG GAG   1228
Phe Gln Ser Ala Pro Tyr Tyr Asp Ser Ala Trp Ala Pro Thr Ala Glu
                310                 315                 320

ATC TTC AGC AAG TAC GTC GCC GGC GAC ACC CAG GCG CTC GTC GAC GCC   1276
Ile Phe Ser Lys Tyr Val Ala Gly Asp Thr Gln Ala Leu Val Asp Ala
                325                 330                 335

GCC GCA CCC GAC CTG TCC GAC ACC GCG GGC AAC GCC TCC GCG GAG AAC   1324
Ala Ala Pro Asp Leu Ser Asp Thr Ala Gly Asn Ala Ser Ala Glu Asn
340                 345                 350

GGC AAC GCC GTC TAC ACG GCC GTC GAG TGC ACC GAC GCC AAG TGG CCC   1372
Gly Asn Ala Val Tyr Thr Ala Val Glu Cys Thr Asp Ala Lys Trp Pro
355                 360                 365                 370

GCC AAC TGG CGC ACC TGG GAC CGG GAC AAC ACC CGG CTC CAC CGC GAC   1420
Ala Asn Trp Arg Thr Trp Asp Arg Asp Asn Thr Arg Leu His Arg Asp
                375                 380                 385

CAC CCG TTC ATG ACC TGG GCC AAC GCC TGG ATG AAC CTG CCC TGT GCC   1468
His Pro Phe Met Thr Trp Ala Asn Ala Trp Met Asn Leu Pro Cys Ala
                390                 395                 400

ACC TGG CCG GTC AAG CAG CAG ACC CCG CTG AAC GTG AAG ACC GGC AAG   1516
Thr Trp Pro Val Lys Gln Gln Thr Pro Leu Asn Val Lys Thr Gly Lys
        405                 410                 415
```

FIG. 12C

```
GGA CTT CCG CCG GTG CTG ATC GTC CAG TCC GAG CGT GAC GCC GCC ACC    1564
Gly Leu Pro Pro Val Leu Ile Val Gln Ser Glu Arg Asp Ala Ala Thr
420                 425                 430

CCG TAC GAG GGC GCC GTC GAA CTG CAC CAG CGG TTC CGG GGA TCC CGC    1612
Pro Tyr Glu Gly Ala Val Glu Leu His Gln Arg Phe Arg Gly Ser Arg
435                 440                 445                 450

CTG ATC ACC GAG CGG GAC GCC GGC TCC CAC GGC GTC ACC GGC CTG GTC    1660
Leu Ile Thr Glu Arg Asp Ala Gly Ser His Gly Val Thr Gly Leu Val
            455                 460                 465

AAC CCG TGC ATC AAC GAC CGG GTC GAC ACC TAC CTG CTC ACC GGC AGG    1708
Asn Pro Cys Ile Asn Asp Arg Val Asp Thr Tyr Leu Leu Thr Gly Arg
        470                 475                 480

ACG GAC GCC CGC GAC GTG ACC TGC GCG CCG CAC GCC ACG CCC AGG CCG    1756
Thr Asp Ala Arg Asp Val Thr Cys Ala Pro His Ala Thr Pro Arg Pro
485                 490                 495                 500

TAA CCCGGGCTCA GGCCAAGCGG GGGGAGGGGG CGACCGGTCC GACCGGCCGC         1809
End
CCCCTCCCCC CACCTGTCGC TACCGTCCCT CGGCCCAGGC GTCCTCCGCC GGTAGTCGA   1869
AGAGGTCGCC GTACGCCTTG AACATCTTCG GGTAGCCT                          1908
```

FIG. 13

Tap (199) K L N Y L G V S Y G T Y L G A V Y G T L F P D H V R R M V V(228)
HOHH (98) R V D L V G N S F G G A L S L A F A I R F P H R V R R L V L(127)

FIG. 20A

```
GGTACCAGGC GACGAAGGCG ACGGTCAGCG GGAACGCGAA GGAACGGAAG GAGCGGCGCA   60
GTTCGGCGAA CTCGGCGCTC TGCTGCACTT CGGAGAACTC CTCGGCGGAG GGGAGGCGGT  120
GCTCCTCTTG CGAGGGGGGC TCCTCTTTGG AGGGGGGCGG TGCGTCGGGT GGCCACGGAG  180
TCTCCTCGTA CGACGGACAT GACGGCTTGG ACCTCGGTGT TCTCGCAGGG GGCTGATCGT  240
GCTCGGGCTC CCTGTCCAAC GACACGGCGC CCCGCGGGGC CCGGTTCAAC ACCCGTGGCA  300
CTTTCCGAAG TCGTCCTCGG CGGGTCATTG CTGGCCAGGG ACTTCGGGGG ATAGCTTCAC  360
CCTGCACCAC TACGTCATGT ACCTGCCCGG CCCGTTTCAC CCGTGCCCGG GCAGGTGCTG  420
TTTGCCGGAT GATGTGGAGA CCCCATGGAT CATCTGCGCT TCCCGCGCGA CCCGCGCTCC  480
AGACGCGGGC TCGTTTCCCG AGCTTTCCCG ACGGACTGGA GACATCACGC ATG ACC     536
                                                      fMet Thr
```

```
GCT CCC CTC TCG CGT CAC CGC CGT GCC CTC GCG ATT CCG GCG GGC CTG   584
Ala Pro Leu Ser Arg His Arg Arg Ala Leu Ala Ile Pro Ala Gly Leu
       -120               -115               -110

GCC GTG GCC GCG TCG CTC GCG TTC CTG CCG GGC ACC CCG GCC GCC GCG   632
Ala Val Ala Ala Ser Leu Ala Phe Leu Pro Gly Thr Pro Ala Ala Ala
   -105                -100                -95

ACC CCC GCG GCC GAG GCC GCG CCC TCG ACG GCG GCG GAC GCG ACC TCG   680
Thr Pro Ala Ala Glu Ala Ala Pro Ser Thr Ala Ala Asp Ala Thr Ser
-90                   -85                  -80                -75

CTC AGC TAC GTC GTC AAC GTC GCC TCC GGG CAC CGT CCT TCG GCC ACC   728
Leu Ser Tyr Val Val Asn Val Ala Ser Gly His Arg Pro Ser Ala Thr
            -70                 -65                      -60

GTG CGG CGG GCG ATA GCC AAG GCG GGC GGC ACG ATC GTC ACG TCG TAC   776
Val Arg Arg Ala Ile Ala Lys Ala Gly Gly Thr Ile Val Thr Ser Tyr
                -55             -50                  -45

GAC CGG ATC GGC GTG ATC GTC GTC CAC TCC GCC AAC CCC GAC TTC GCC   824
Asp Arg Ile Gly Val Ile Val Val His Ser Ala Asn Pro Asp Phe Ala
             -40             -35                -30

AAG ACC GTG CGC AAG GTG CGC GGC GTG CAG TCG GCC GGT GCC ACC CGC   872
Lys Thr Val Arg Lys Val Arg Gly Val Gln Ser Ala Gly Ala Thr Arg
        -25             -20                 -15

ACC GCG CCA CTG CCC TCG GCC GCC ACC ACC GAC ACG GGC GCG CCG CAG   920
Thr Ala Pro Leu Pro Ser Ala Ala Thr Thr Asp Thr Gly Ala Pro Gln
-10                 -5                   1                   5

GTG CTC GGC GGC GAG GAC CTG GCC GCC GCC AAG GCC GCC TCC GCG AAG   968
Val Leu Gly Gly Glu Asp Leu Ala Ala Ala Lys Ala Ala Ser Ala Lys
            10                  15                  20

GCC GAG GGC CAG GAC CCG CTG GAG TCG CTC CAG TGG GAC CTG CCC GCC  1016
Ala Glu Gly Gln Asp Pro Leu Glu Ser Leu Gln Trp Asp Leu Pro Ala
        25                  30                  35
```

FIG. 20B

| | | | | | | | | | | | | | | |
|---|---|---|---|---|---|---|---|---|---|---|---|---|---|---|
| ATC | AAG | GCG | GAC | AAG | GCG | CAC | GAG | AAG | TCG | CTG | GGC | AGC | AGG | AAG | GTG | 1064
| Ile | Lys | Ala | Asp | Lys | Ala | His | Glu | Lys | Ser | Leu | Gly | Ser | Arg | Lys | Val |
| | 40 | | | | 45 | | | | | 50 | | | | |

```
ATC AAG GCG GAC AAG GCG CAC GAG AAG TCG CTG GGC AGC AGG AAG GTG      1064
Ile Lys Ala Asp Lys Ala His Glu Lys Ser Leu Gly Ser Arg Lys Val
    40              45                  50

ACC GTC GCC GTC ATC GAC ACC GGC GTC GAC GAC ACC CAC CCG GAC ATC      1112
Thr Val Ala Val Ile Asp Thr Gly Val Asp Asp Thr His Pro Asp Ile
55              60                  65                  70

GCC CCG AAC TTC GAC CGG CAG GCG TCC GTC AAC TGT GTG GCG GGC AAG      1160
Ala Pro Asn Phe Asp Arg Gln Ala Ser Val Asn Cys Val Ala Gly Lys
                75                  80                  85

CCG GAC ACC GCC GAC GGG GCC TGG CGG CCG AGC GCG GCG GAG AGC CCG      1208
Pro Asp Thr Ala Asp Gly Ala Trp Arg Pro Ser Ala Ala Glu Ser Pro
            90                  95                  100

CAC GGC ACC CAC GTG GCC GGG GAG ATA GCC GCC GCC AAG AAC GGC GTC      1256
His Gly Thr His Val Ala Gly Glu Ile Ala Ala Ala Lys Asn Gly Val
                105                 110                 115

GGC ATG ACC GGC GTG GCA CCC GGG GTG AAG GTG GCC GGC ATC AAG GTC      1304
Gly Met Thr Gly Val Ala Pro Gly Val Lys Val Ala Gly Ile Lys Val
120                 125                 130

TCC AAC CCC GAC GGC TTC TTC TAC ACC GAG GCC GTG GTC TGC GGC TTC      1352
Ser Asn Pro Asp Gly Phe Phe Tyr Thr Glu Ala Val Val Cys Gly Phe
135                 140                 145                 150

ATG TGG GCG GCC GAG CAC GGC GTC GAC GTG ACC AAC AAC AGC TAT TAC      1400
Met Trp Ala Ala Glu His Gly Val Asp Val Thr Asn Asn Ser Tyr Tyr
                155                 160                 165

ACC GAC CCG TGG TAC TTC AAC TGC AAG GAC GAG CCC GAC CAG AAG GCG      1448
Thr Asp Pro Trp Tyr Phe Asn Cys Lys Asp Asp Pro Asp Gln Lys Ala
            170                 175                 180

CTC GTC GAG GCC GTC TCG CGG GCC TCC CGG TAC GCG GAG AAG AAG GGC      1496
Leu Val Glu Ala Val Ser Arg Ala Ser Arg Tyr Ala Glu Lys Lys Gly
            185                 190                 195

GCG GTC AAC GTC GCC GCG GCC GGC AAC GAG AAC TAC GAC CTC ACC TCC      1544
Ala Val Asn Val Ala Ala Ala Gly Asn Glu Asn Tyr Asp Leu Thr Ser
        200                 205                 210

GAC GAG ATC ACC GAC CCG TCC TCG CCC AAC GAC ACC ACG CCC GGC GAC      1592
Asp Glu Ile Thr Asp Pro Ser Ser Pro Asn Asp Thr Thr Pro Gly Asp
215                 220                 225                 230
```

FIG. 20C

```
CGG ACC GTC GAC CCG TCG AAG TGC CTG GAC ATC CCG ACC CAG CTG CCG    1640
Arg Thr Val Asp Pro Ser Lys Cys Leu Asp Ile Pro Thr Gln Leu Pro
            235             240             245

GGT GTC GTG ACG GTC GCG GCG ACC GGT GCG AAG GGC CTC AAG TCG TCC    1688
Gly Val Val Thr Val Ala Ala Thr Gly Ala Lys Gly Leu Lys Ser Ser
            250             255             260

TTC TCC AAC CAC GGG CTG GGC GTC ATC GAC ATC GCC GCG CCC GGC GGC    1736
Phe Ser Asn His Gly Leu Gly Val Ile Asp Ile Ala Ala Pro Gly Gly
            265             270             275

GAC TCG ACG GCC TAC CAG ACC CCG GAG CCG CCC GCC ACG AGC GGC CTG    1784
Asp Ser Thr Ala Tyr Gln Thr Pro Glu Pro Pro Ala Thr Ser Gly Leu
            280             285             290

ATC CTG GGC ACG CTG CCC GGC GGC AAG TGG GGC TAC ATG GCC GGT ACG    1832
Ile Leu Gly Thr Leu Pro Gly Gly Lys Trp Gly Tyr Met Ala Gly Thr
295             300             305             310

TCC ATG GCC TCC CCG CAC GTC GCG GGC GTC GCC GCC CTC ATC AAG TCG    1880
Ser Met Ala Ser Pro His Val Ala Gly Val Ala Ala Leu Ile Lys Ser
            315             320             325

ACG CAC CCG CAC GCC TCC CCC GCC ATG GTG AAG GCG CTG CTG TAC GCC    1928
Thr His Pro His Ala Ser Pro Ala Met Val Lys Ala Leu Leu Tyr Ala
            330             335             340

GAG GCC GAC GCC ACG GCG TGC ACC AAG CCG TAC GAC ATC GAC GGC GAC    1976
Glu Ala Asp Ala Thr Ala Cys Thr Lys Pro Tyr Asp Ile Asp Gly Asp
            345             350             355

GGC AAG GTC GAC GCG GTG TGC GAG GGC CCG AAG AAC CGC AAC GGC TTC    2024
Gly Lys Val Asp Ala Val Cys Glu Gly Pro Lys Asn Arg Asn Gly Phe
            360             365             370

TAC GGC TGG GGC ATG GCC GAC GCG CTG GAC GCG GTG ACC TGG TAG CCGGT
Tyr Gly Trp Gly Met Ala Asp Ala Leu Asp Ala Val Thr Trp ter
375             380             385

ACGCGTACCC GGTGCGTGAG GCGGGGGCGG CGGTCCGGTT CCCGTCCGGT CCGCCGCCCC  2074
CGTCGTCGTC GTCGTACGAC AGTATCTTCG CCATGGACAC TTACGAGGAT CC          2185
```

FIG. 21

```
            10v       20v       30v       40v       50v       60v
1   MTAPLSRHRRALAIPAGLAVAASLAFLPGTPAAATPAAEAAPSTAADATSLSYVVNVASGH
                                     :..:       : A :
2                                               MRGKKVWISLLFALAL
                                                 10^
            70v       80v       90v      100v      110v      120v
1   RPSATVRRAIAKAGGTIVTSYDRIGVIVVHSANPDFAKTVRKVRGVQSAGATRTAPLPSAA
      :   :  .: : .::.   .:  .:  V  :: :.   A  .:.V : ::: . :    .AA
2   IFTMAFGSTSSAQAAGKSNGEKKYIVGFKQTMSTMSAAKKKDVISEKGGKVQKQFKYVDAA
         20^       30^       40^       50^       60^       70^
           130v      140v      150v      160v      170v      180v
1   TTDTGAPQVLGGEDLAAAKAASAKAEGQDPLESLQWDLPAIKADKAHEKSLGSRKVTVAVI
    ::. .. .V . .. ::.    .... ::.   :S:...::..IKA   H.:: .:.:V.VAVI
2   SATLNEKAVKELKKDPSVAYVEEDHVAHAYAQSVPYGVSQIKAPALHSQGYTGSNVKVAVI
         80^       90^      100^      110^      120^      130^
           190v      200v      210v      220v      230v      240v
1   DTGVDDTHPDIAPNFDRQASVNCVAGKPDTADGAWRPSAAESPHGTHVAGEIAAAKNGVGM
    D:G:D..:HPD:              VAG :. .  :....P ..:::HGTHVAG.:AA :N::G:
2   DSGIDSSHPDL-----------KVAGGASMVPSETNPFQDNNSHGTHVAGTVAALNNSIGV
    140^                 150^      160^      170^      180^
           250v      260v      270v      280v      290v      300v
1   TGRWHPGVKVAGIKVSNPDGFFYTEAVVCGFMWAAEHGVDVTNNSYYTDPWYFNCKDDPDQ
      G    P:...:  ::KV .:DG    . ::  G: WA .:.:DV.N S   . :
2   LGV-APSASLYAVKVLGADGSGQYSWIINGIEWAIANNMDVINMSLGGPSGS---------
    190^      200^      210^      220^      230^
           310v      320v      330v      340v      350v      360v
1   KALVEAVSRASRYAEKKGAVNVAAAGNENYDLTSDEITDPSSPNDTTPGDRTVD-----PS
     AL   AV  A       G V VAAAGNE          T  SS      PG
2   AALKAAVDKA---V-ASGVVVVAAAGNEG--------TSGSSSTVGYPG-KYPSVIAVGAV
    240^      250^      260^              270^      280^
           370v      380v      390v      400v      410v      420v
1   KCLDIPTQLPGVVTVAATGAKGLKSSFSNHGLGVIDIAAPGGDSTAYQTPEPPATSGL-IL
                          F    G  D                              G: I
2   DSSN-----------------RASFSSVG-PELD-----------------VMAPGVSIQ
    290^                 300^                          310^
           430v      440v      450v      460v      470v      480v
1   GTLPGGKWGYMAGTSMASPHVAGVAALIKSTHPHASPAMVKALLYAEADATACTKPYDIDG
    :TLPG.K.G  .GTSMASPHVAG.AALI S.HP: : : V:: L ..:.  :     Y:' :
2   STLPGNKYGAYNGTSMASPHVAGAAALILSKHPNWTNTQVRSSLENTTTKLGDSFYYGKGL
         320^      330^      340^      350^      360^      370^
           490v      500v      510v
1   DGKVDAVCEGPKNRNGFYGWGMADALDAVTW
     .  .A.
2   INVQAAAQ
       380^
```

FIG. 25A

```
CCCGGGCCCG CGTCGGAGTC ATGACCGGTT GACGCCGTAA CACGTACGGG GCACGCGCAC  60
CACGCACCGC AACTGCTTCG TCGCGGAGAG TTACGCTCGC TGA ATG GAC ACA AGG  115
                                               Met Asp Thr Arg
                                                   -45
```

| | | | | | | | | | | | | | | | |
|---|---|---|---|---|---|---|---|---|---|---|---|---|---|---|---|
| CGC | ACT | CAC | CGC | AGG | ACC | CGC | ACC | GGC | GGC | ACC | CGT | TTC | CGG | GCC | ACG | 163 |
| Arg | Thr | His | Arg | Arg | Thr | Arg | Thr | Gly | Gly | Thr | Arg | Phe | Arg | Ala | Thr |
|     |     | -40 |     |     |     |     | -35 |     |     |     |     |     | -30 |     |     |

CTG CTC ACC GCC GCG CTG CTC GCC ACC GCC TGC TCG GCC GGG GGC GCG  211
Leu Leu Thr Ala Ala Leu Leu Ala Thr Ala Cys Ser Ala Gly Gly Ala
        -25             -20                 -15

TCG ACG TCC GCC GGA TCC CCC GCG GCC AAG GCG GCC GGC GCG ACG GAG  259
Ser Thr Ser Ala Gly Ser Pro Ala Ala Lys Ala Ala Gly Ala Thr Glu
        -10             -5                   1              5

GCG GCC ACG GCG ACC CTG ACC CCC CTG CCG AAG GCC ACG CCC GCC GAG  307
Ala Ala Thr Ala Thr Leu Thr Pro Leu Pro Lys Ala Thr Pro Ala Glu
            10              15                      20

CTG TCC CCG TAC TAC GAG CAG AAG CTC GGC TGG CGC GAC TGC GGC GTC  355
Leu Ser Pro Tyr Tyr Glu Gln Lys Leu Gly Trp Arg Asp Cys Gly Val
        25                  30                      35

CCG GGC TTC CAG TGC GCC ACC ATG AAG GCC CCG CTC GAC TAC GCC AAG  403
Pro Gly Phe Gln Cys Ala Thr Met Lys Ala Pro Leu Asp Tyr Ala Lys
        40                  45                      50

CCC GCC GAC GGC GAC GTC CGG CTC GCG GTG GCC CGC AAG AAG GCC ACG  451
Pro Ala Asp Gly Asp Val Arg Leu Ala Val Ala Arg Lys Lys Ala Thr
    55                      60                  65

GGG CCG GGC AAG CGC CTC GGC TCG CTG CTG GTC AAC CCG GGC GGA CCG  499
Gly Pro Gly Lys Arg Leu Gly Ser Leu Leu Val Asn Pro Gly Gly Pro
70              75                  80                      85

GGC GGC TCG GCG ATC GGC TAC CTC CAG CAG TAC GCG GGC ATC GGC TAC  547
Gly Gly Ser Ala Ile Gly Tyr Leu Gln Gln Tyr Ala Gly Ile Gly Tyr
                90              95                  100

CCG GCG AAG GTC CGC GCC CAG TAC GAC ATG GTG GCG GTC GAC CCC CGG  595
Pro Ala Lys Val Arg Ala Gln Tyr Asp Met Val Ala Val Asp Pro Arg
        105                 110                 115

GGC GTG GCC CGC AGT GAA CCC GTC GAG TGC CTG GAC GGG CGC GAG ATG  643
Gly Val Ala Arg Ser Glu Pro Val Glu Cys Leu Asp Gly Arg Glu Met
        120                 125                 130

GAC GCG TAC ACG CGC ACC GAC GTC ACC CCG GAC GAC GCG GGC GAG ACG  691
Asp Ala Tyr Thr Arg Thr Asp Val Thr Pro Asp Asp Ala Gly Glu Thr
    135                 140                 145

FIG. 25B

```
GAC GAG CTG GTC GAC GCC TAC AAG GAG TTC GCC GAG GGC TGC GGG GCG   739
Asp Glu Leu Val Asp Ala Tyr Lys Glu Phe Ala Glu Gly Cys Gly Ala
150                 155                 160                 165

GAC GCG CCG AAG CTG CTG CGC CAC GTC TCC ACG GTC GAG GCG GCA CGC   787
Asp Ala Pro Lys Leu Leu Arg His Val Ser Thr Val Glu Ala Ala Arg
            170                 175                 180

GAC ATG GAC GTC CTG CGC GCG GTG CTG GGC GAC GAG AAG CTG ACC TAC   835
Asp Met Asp Val Leu Arg Ala Val Leu Gly Asp Glu Lys Leu Thr Tyr
                185                 190                 195

GTG GGA GCG TCG TAC GGC ACC TTC CTG GGC GCG ACC TAC GCC GGT CTG   883
Val Gly Ala Ser Tyr Gly Thr Phe Leu Gly Ala Thr Tyr Ala Gly Leu
        200                 205                 210

TTC CCC GAC CGG ACG GGC CGC CTG GTC CTG GAC GGC GCG ATG GAC CCC   931
Phe Pro Asp Arg Thr Gly Arg Leu Val Leu Asp Gly Ala Met Asp Pro
    215                 220                 225

TCG CTG CCC GCC CGC CGC CTG AAC CTG GAG CAG ACG GAG GGC TTC GAG   979
Ser Leu Pro Ala Arg Arg Leu Asn Leu Glu Gln Thr Glu Gly Phe Glu
230                 235                 240                 245

ACG GCG TTC CAG TCC TTC GCG AAG GAC TGC GTG AAG CAG CCG GAC TGC  1027
Thr Ala Phe Gln Ser Phe Ala Lys Asp Cys Val Lys Gln Pro Asp Cys
                250                 255                 260

CCC CTC GGC GAC AAG GAC ACC ACC CCC GAC CAG GTC GGC AAG AAC CTC  1075
Pro Leu Gly Asp Lys Asp Thr Thr Pro Asp Gln Val Gly Lys Asn Leu
            265                 270                 275

AAG TCC TTC TTC GAC GAC CTG GAC GCG AAG CCC CTG CCC GCC GGC GAC  1123
Lys Ser Phe Phe Asp Asp Leu Asp Ala Lys Pro Leu Pro Ala Gly Asp
        280                 285                 290

GCC GAC GGC CGC AAG CTC ACC GAA TCC CTC GCC ACC ACC GGC GTG ATC  1171
Ala Asp Gly Arg Lys Leu Thr Glu Ser Leu Ala Thr Thr Gly Val Ile
    295                 300                 305

GCC GCG ATG TAC GAC GAG GGC GCC TGG CAG CAG CTG CGC GAG TCC CTC  1219
Ala Ala Met Tyr Asp Glu Gly Ala Trp Gln Gln Leu Arg Glu Ser Leu
310                 315                 320                 325

ACC TCG GCG ATC AAG GAG AAG GAC GGT GCG GGC CTG CTG ATC CTC TCC  1267
Thr Ser Ala Ile Lys Glu Lys Asp Gly Ala Gly Leu Leu Ile Leu Ser
                330                 335                 340

GAC AGC TAC TAC GAG CGC GAG GCC GAC GGC GGC TAC AGC AAC CTG ATG  1315
Asp Ser Tyr Tyr Glu Arg Glu Ala Asp Gly Gly Tyr Ser Asn Leu Met
            345                 350                 355
```

FIG. 25C

```
TTC GCC AAC GCC GCC GTG AAC TGC CTC GAC CTC CCC GCC GCC TTC TCC    1363
Phe Ala Asn Ala Ala Val Asn Cys Leu Asp Leu Pro Ala Ala Phe Ser
        360                 365                 370

TCC CCG GAC GAG GTG CGC GAC GCC CTC CCC GAC TTC GAG AAG GCG TCC    1411
Ser Pro Asp Glu Val Arg Asp Ala Leu Pro Asp Phe Glu Lys Ala Ser
    375                 380                 385

CCG GTC TTC GGC GAG GGC CTC GCC TGG TCC TCC CTG AAC TGC GCG TAC    1459
Pro Val Phe Gly Glu Gly Leu Ala Trp Ser Ser Leu Asn Cys Ala Tyr
390                 395                 400                 405

TGG CCG GTG AAG CCC ACG GGG GAG CCG CAC CGC ATC GAG GCG GCC GGC    1507
Trp Pro Val Lys Pro Thr Gly Glu Pro His Arg Ile Glu Ala Ala Gly
            410                 415                 420

GCC ACC CCG ATC GTC GTG GTC GGC ACC ACC CGC GAC CCG GCC ACC CCC    1555
Ala Thr Pro Ile Val Val Val Gly Thr Thr Arg Asp Pro Ala Thr Pro
                425                 430                 435

TAC CGC TGG GCC GAG GCC CTC TCC GAC CAG CTC ACC TCC GGC CAC CTC    1603
Tyr Arg Trp Ala Glu Ala Leu Ser Asp Gln Leu Thr Ser Gly His Leu
            440                 445                 450

CTC ACC TAC GAG GGA GAC GGC CAC ACC GCG TAC GGC CGC GGC AGC TCC    1651
Leu Thr Tyr Glu Gly Asp Gly His Thr Ala Tyr Gly Arg Gly Ser Ser
        455                 460                 465

TGC ATC GAC TCC GCG ATC AAC ACG TAC CTG CTG ACC GGC ACC GCC CCG    1699
Cys Ile Asp Ser Ala Ile Asn Thr Tyr Leu Leu Thr Gly Thr Ala Pro
470                 475                 480                 485

GAG GAC GGC AAG CGC TGC TCG TAA CCCCC GCCTGCCCGC CCCGGGACCC ACGCCTCCGG    1758
Glu Asp Gly Lys Arg Cys Ser ter
                490
GGGCGGGTTC GGAGCACCCC GGGAAACTGT GTAGACTTGC CGACGTTGCT GATCGCACCA TGG    1821
```

FIG. 26

```
P5-6  MDTRRTHRRTRTGGTRFRATLLTAALLATACSAGGASTSAGSPAAKAAGATEAATATLTPLKATPAELSPYYEQKLGWRDCGVPGFQCATHKAPLDYAKP   101
       R:: R R:.:  ::L:TA:L:A.A SA :AS::::. :.: :..A :: .: ::A:.A.:: . :W.  P :QC: :..P:DYAKP              96
Tap   MRKSSIRRRATAFGTAGALVTATLIAGAVSAPAASAAPADGHGHGRSWDREARGAAIAARAARAGID-WEDCAADWNL-PKP-IQCGYTVPMDYAKP

P5-6  ADGDVRLAVARKKATG-PGKRLGSLLVNPGGPGGSAIGYLQQYAGIGYP-AKVRAQYDMVAVDPRGVARSEPVECLDGREMDAYTRTDVTPDDAGETDELV  200
       : ::RLAV.R  .TG .:.R G:L: NPGGPGGS:: : .: A:. .YD.V: DPRGV::S.P:.C:D :E.   .::D .P:..::..            197
Tap    YGKQIRLAVDRIGNTGTRSERQGALIYNPGGPGGSGLRFPARVTNKSAVNMNTAKAYDFVGFDPRGVGHSAPISCVDPQEFVKAPKADPVPGSEADKRAQR

P5-6  DAYKEPAEGCGADAPKLLRHVSTVEAARDMDVLRAVLGDEKLTYVGASYGTFLGATYAGLFPDRTGRLVLDGAMDPSLPARRL--NLEQTEGFETAFQSFA  299
      . :R:AEGC . :  :L.:H:T  ::ARD:DV:RA.LG:.KL.Y:G.SYGT:LGA.Y:.LFPD:. R:V:D:.::PS   :  NL:Q. :FE. .:...   298
Tap   KLAREYAEGCFERSGEMLPHMTTPNTARDLDVIRAALGEKKLMYLGVSYGTYLGAVIGTLFPDHVRRMVVDSVVNPSRDKIWYQANLDQDVAFEGRWKDWQ

P5-6  K-DCVKQPDCPLGDKDTTPDQVGKNLKSFFDDLDAKPLPAGDADGRKLTESLATTGVIAAMYDEGAHQQLRESLTSAIKEKDGAGLLILSDSYYEREADGG  399
       .:::...LGD. :. ::   :L::  .  .KPL Q:. G.    ..L : ... A: .  E ::. : ... A: YD :AM.  ::   ::         300
Tap   DWVAANDAAYHLGDTRAEVQDQWLKLRA---AAAKKPL--GGVVGP---AELISFFQSAPYYD-SAWAPTAEIFSKYVAGDTQALVDAAAPDLSDTAGNAS

P5-6  YSNLMFANAAVNCLDLPAAFSSPDEVRDALPDFEKASPVFGEGLAWSSLNCAYWPVKPTGEPHRIEAAGATPIVVGTTRDPATPYRWAEALSDQLTSGHL  500
       .N  .:AV:C D    :   :.   RD.. :::.  P .. : AW :L CA WPVK. . . :: Q .P::V :.RD:ATPY  A .L ::: :::L   490
Tap   AENGNAVYTAVECTDAKWPANWRTWDRDN-TRLHRDHPFMTWANAWMNLPCATHPVKQQTPLNVKTGKGLPPVLIVQSERDAATPYEGAVELHQRFPGSRL

P5-6  LT-YEGDGHTAYGRGSSCIDSAINTYLLTGTAPEDGKRCS                                                             540
      :T :::::H. G :::C:.. ::TYLLIQ :. .: C:                                                               537
Tap   ITERDAGSHGVTGLVNPCINDRVDTYLLTGRTDARDVTCAPHATPRP
```

FIG. 29A

```
GGTACCGGCG GCCAAGACCG TGTGCTCCTG ACCGCGGACG CCACCACAGG TCGGCAGAAG         60
CAGCAGATCG ACAGAAGTAG CAGGTCAGAG CGTTATCCAC AGGCGTCGGC GGGTGCTGCC        120
CCCGCCACCT ACCATGGCAG GAACGCCATC CGCCGCACGG CGCGGACGGC TTGCCAGGGG        180
GGAGAGGAC ATG GCG CGT CTC GTC CGG TGG ACG GCT CTG ACG GCC GCC GCC GCA   234
          fMet Ala Arg Leu Val Arg Trp Thr Ala Leu Thr Ala Ala Ala Ala
                        5                  10                       15

CTG CTG ACG GCG GGC TGC AGC GGC GGC TCG TCC GAC GAG GAC AAG GAC         282
Leu Leu Thr Ala Gly Cys Ser Gly Gly Ser Ser Asp Glu Asp Lys Asp
                 20                  25                  30

GAC GGG GGC AGG AGC AGC GCG GGA CCT TCG GCG GCG GCA CCC TCC GGG         330
Asp Gly Gly Arg Ser Ser Ala Gly Pro Ser Ala Ala Ala Pro Ser Gly
                 35                  40                  45

GTG CCG GAG GCA CTG GCG TCC CAG ACG CTG GAC TGG GCC CGA TGC GAG         378
Val Pro Glu Ala Leu Ala Ser Gln Thr Leu Asp Trp Ala Arg Cys Glu
             50                  55                  60

GGC AGC GAC GAT GCC CCG GCG CCG GAC GGC GAC TGG CGG TGC GCC ACG         426
Gly Ser Asp Asp Ala Pro Ala Pro Asp Gly Asp Trp Arg Cys Ala Thr
         65                  70                  75

CTG AAG GCA CCG CTG GAC TGG TCC GAC CCC GAC GGC GAG ACG ATC GAT         474
Leu Lys Ala Pro Leu Asp Trp Ser Asp Pro Asp Gly Glu Thr Ile Asp
 80                  85                  90                      95

CTC GCG CTG ATC CGG TCC CGG GCG AGC GGG GAC GAC CGC ATC GGC TCC         522
Leu Ala Leu Ile Arg Ser Arg Ala Ser Gly Asp Asp Arg Ile Gly Ser
                100                 105                 110

CTG CTG TTC AAC TTC GGC GGC CCG GGC GCC TCC GGC GTC TCC ACG ATG         570
Leu Leu Phe Asn Phe Gly Gly Pro Gly Ala Ser Gly Val Ser Thr Met
             115                 120                 125

CCG TCC TAC GCC GAC ACC GTC TCC TCC CTG CAC GAG CGG TAC GAC CTG         618
Pro Ser Tyr Ala Asp Thr Val Ser Ser Leu His Glu Arg Tyr Asp Leu
         130                 135                 140

GTG AGC TGG GAC CCG CGC GGG GTG GCC GCC AGC GAG GGC GTC CGC TGC         666
Val Ser Trp Asp Pro Arg Gly Val Ala Ala Ser Glu Gly Val Arg Cys
     145                 150                 155

CGC ACC GAC GAG GCG ATC GAG GCC GCC GAG TCG GTG GAC TCC ACG CCG         714
Arg Thr Asp Glu Ala Ile Glu Ala Ala Glu Ser Val Asp Ser Thr Pro
160                 165                 170                 175

GAC TCC CCG GCC GAG GAG CAG GCC TAC CTG AAG GAC GCC GCC GAC TTC         762
Asp Ser Pro Ala Glu Glu Gln Ala Tyr Leu Lys Asp Ala Ala Asp Phe
                180                 185                 190
```

FIG. 29B

| | |
|---|---|
| GGC AGG GGC TGC GAG AAG GCC GCC GGC AAG CTC ATG GAA CAC GTC TCG<br>Gly Arg Gly Cys Glu Lys Ala Ala Gly Lys Leu Met Glu His Val Ser<br>            195                    200                  205 | 810 |
| ACC ACG GAC ACG GCC CGC GAC ATG GAC CTG ATG CGG CAC GTC CTG GGC<br>Thr Thr Asp Thr Ala Arg Asp Met Asp Leu Met Arg His Val Leu Gly<br>            210                    215                  220 | 858 |
| GAC GAG AGG ATG CAC TAC TTC GGC ATC TCC TAC GGC ACC GAA CTC GGC<br>Asp Glu Arg Met His Tyr Phe Gly Ile Ser Tyr Gly Thr Glu Leu Gly<br>            225                    230                  235 | 906 |
| GGC GTC TAC GCC CAT CTG TTC CCC GAG CAC GTG GGC CGC GTG ATC CTC<br>Gly Val Tyr Ala His Leu Phe Pro Glu His Val Gly Arg Val Ile Leu<br>240                    245                    250                  255 | 954 |
| GAC GCG GTG GTG GAC CCG GGC GCC GAC ACG ATG GGC CAC GCC GAG AAC<br>Asp Ala Val Val Asp Pro Gly Ala Asp Thr Met Gly His Ala Glu Asn<br>                      260                    265                  270 | 1002 |
| CAG GCC AGG GGT TTC CAG CGC GCG CTG GAC GAC TAC CTG GAG TCG ACC<br>Gln Ala Arg Gly Phe Gln Arg Ala Leu Asp Asp Tyr Leu Glu Ser Thr<br>            275                    280                  285 | 1050 |
| GGC CAG GAA CCC GAA CAG GGG TCG CGG AAG ATC GCC GGC CTG CTG GAG<br>Gly Gln Glu Pro Glu Gln Gly Ser Arg Lys Ile Ala Gly Leu Leu Glu<br>            290                    295                  300 | 1098 |
| CGG CTG GAC GCC GAG CCA CTG CCC ACG TCC TCG CCG GGG CGG GAG CTG<br>Arg Leu Asp Ala Glu Pro Leu Pro Thr Ser Ser Pro Gly Arg Glu Leu<br>            305                    310                  315 | 1146 |
| ACG CAG ACC CTC GCG TTC ACC GGC ATC GTG CTG CCG CTG TAC AGC GAG<br>Thr Gln Thr Leu Ala Phe Thr Gly Ile Val Leu Pro Leu Tyr Ser Glu<br>320                    325                    330                  335 | 1194 |
| AGC GGC TGG CCG GCC CTG ACC AGT GCG CTG AAG GCG GCC GAG GAG GGC<br>Ser Gly Trp Pro Ala Leu Thr Ser Ala Leu Lys Ala Ala Glu Glu Gly<br>                      340                    345                  350 | 1242 |
| GAC GGC TCG GAG TTG CTG GCC CTC GCC GAC GGC TAC AAC GAG CGT GAT<br>Asp Gly Ser Glu Leu Leu Ala Leu Ala Asp Gly Tyr Asn Glu Arg Asp<br>            355                    360                  365 | 1290 |
| CCC TCG GGG CGC TAC GGC ACG ACG ACC CAC TCG CAA AGG GTC ATA TCG<br>Pro Ser Gly Arg Tyr Gly Thr Thr Thr His Ser Gln Arg Val Ile Ser<br>            370                    375                  380 | 1338 |
| TCG CTG GAC GAC AAG CAG AGG CCG ACC GTG GAG GAG ACG AAG AAG CTG<br>Cys Leu Asp Asp Lys Gln Arg Pro Thr Val Glu Glu Thr Lys Lys Leu<br>385                    390                    395 | 1386 |

FIG. 29C

```
CTG CCG AGG TTC GAG AAG GTC TCT CCC GTC TTC GGC GCC TTC CTC GGC      1434
Leu Pro Arg Phe Glu Lys Val Ser Pro Val Phe Gly Ala Phe Leu Gly
400             405             410             415

TGG GAC ACG GCC GGG TGG TGC CAC GAC TGG CCG GTG GCC GGT CAG CAC      1482
Trp Asp Thr Ala Gly Trp Cys His Asp Trp Pro Val Ala Gly Gln His
                420             425             430

GAG ACC GCG GAG GTG AGC GCG CCC GAC GCG GCC CCG GTC CTG GTG GTC      1530
Glu Thr Ala Glu Val Ser Ala Pro Asp Ala Ala Pro Val Leu Val Val
            435             440             445

GGC AAC ACG GGC GAC CCG GCC ACG CCC TAC GAG GGC GCC CGC AGG ATG      1578
Gly Asn Thr Gly Asp Pro Ala Thr Pro Tyr Glu Gly Ala Arg Arg Met
        450             455             460

GCG GAC GAG CTG GGC AAG GAC GTC GGC GTG GTG CTG ACC TGG CAG GGC      1626
Ala Asp Glu Leu Gly Lys Asp Val Gly Val Val Leu Thr Trp Gln Gly
    465             470             475

GAG GGA CAC GGT GCC TAC GGG AAC GGA AGC GAC TGT GTC GAC TCC GCG      1674
Glu Gly His Gly Ala Tyr Gly Asn Gly Ser Asp Cys Val Asp Ser Ala
480             485             490             495

GTG GAC GCC TAC CTG TTG AAG GGG ACG GTG CCG AAG GAC GGC AAG GTC      1722
Val Asp Ala Tyr Leu Leu Lys Gly Thr Val Pro Lys Asp Gly Lys Val
                500             505             510

TGC TCA TGA CGGCGGCGGG GGCTTCGGGC ACCTGCGGTG CGCGAAACCC CCGCCG       1771
Cys Ser End
```

STREPTOMYCES PROTEASES AND IMPROVED STREPTOMYCES STRAINS FOR EXPRESSION OF PEPTIDES AND POLYPEPTIDES

FIELD OF THE INVENTION

This invention relates generally to proteases produced by Streptomyces which degrade products expressed in genetically-engineered Streptomyces as hosts, inhibitors of such proteases, improved hosts with impaired protease systems, hosts selected for high expression of such proteases and the use of such proteases, inhibitors and improved hosts.

BACKGROUND OF THE INVENTION

Production methods employing recombinant technology use genetic expression systems. These systems generally consist of host cells encompassing the genetic system to be expressed, and expression vectors which introduce the genetic expression capabilities into the host cells.

Host cells have a variety of endogenous proteases, each with a specific characteristic of action. Degradation by proteases may cause problems in commercial use of genetic expression systems. Degradation of product may also decrease the shelf lives of the bulk protein product and of the final dosage form of drugs.

Endogenous proteases degrade substrates in different ways.

Aminopeptidases have broad substrate specificity, e.g., leucine aminopeptidase (Hanson and Frohne, 1976). However, when a proline residue is reached during degradation, such enzymes are unable to further degrade the peptide. Aminopeptidase P enzymes hydrolyse aminoacyl-proline bonds when proline is in the penultimate position from the amino terminus (X-Pro) of a polypeptide (Yoshimoto et al., 1988). After that action, proline aminopeptidase is capable of removing the exposed amino terminal proline residue.

Dipeptidyl peptidases have been found in many eukaryotic species (Kreil, 1990), but only in a few prokaryotic species (Lloyd et al., 1991; Fukusawa and Harada, 1981). These enzymes can remove N-terminal dipeptides including X-Pro dipeptides.

Tripeptidyl aminopeptidases are capable of degrading a peptide or polypeptide at its amino terminus by removing an amino acid triplet. Tripeptidyl aminopeptidase activity has not previously been reported in prokaryotes; however, serine proteases from human, rat and pig tissues with tripeptidyl aminopeptidase activity have been characterized (McDonald et al., 1985, Balon et al., 1986), and a cDNA sequence has been reported (Tomkinson & Jonsson, 1991).

Endoproteases can also cause rapid degradation of secreted proteins. Serine proteases are widespread throughout the prokaryotes as are metalloproteases. A wide variety of cleavage site specificities have been observed in various microbial species. Enzymes which cleave adjacent to positively charged, negatively charged, and aromatic amino acids have all been reported.

Proteases may be neutralized by various methods including by using inhibitors and by constructing improved strains with impaired proteases.

The use of protease inhibitors to prevent the degradation of proteins during their purification is well established for proteins derived from yeast and higher eukaryotes. This approach has also been employed in the isolation and purification of proteins generated as inclusion bodies from *E. coli*. The general method involves lysing the protein source in the presence of broad spectrum protease inhibitors. Such inhibitors may include leupeptin, EDTA, phenylmethanesulfonylfluoride, or pepstatin.

The application of protease inhibitors in a system involving a living organism is more delicate. EDTA increases the fragility of many microorganisms and can cause cell lysis. Some inhibitors may be taken up by the organism. Such a process may lead to cell death or a disruption of cellular functions. Ideally, a protease inhibitor employed under these conditions should 1) be soluble in the fermentation media, 2) inhibit the target protease as selectively as possible, 3) not inhibit cell growth, and 4) be cost-effective.

Chloromethylketones are known to provide selective inhibition of some proteases. The earliest studied chloromethylketones, tosyllsine chloromethylketone (TLCK) and tosylphenylalanine chloromethylketone (TPCK), selectively inhibit trypsin and chymotrypsin, respectively (Schoellman et al., 1963, Shaw et al., 1965). Longer peptide sequences are needed for the inhibition of certain proteases and improve the specificity of the inhibition in some cases.

The use of improved strains with impaired proteases also can prevent degradation of proteins during production. Improved strains carrying deletional mutations in multiple protease-encoding genes have been made in Bacillus strains (Sloma et al, 1992). International Application Number PCT/US92/01598 of Omnigene, Inc. describes a Bacillus cell containing a mutation in the residual protease III gene resulting in the inhibition of the production by the cell of proteolytically active RP-III. In that case, the inactivation of the major protease allowed detection of other minor proteases which were still present in quantities sufficient to cause degradation of secreted products.

International Application Number PCT/US92/05532 of Amgen Inc. entitled "Isolation and Characterization of a Novel Protease from *Streptomyces Lividans*" describes a protease called "Protease X" of *S. lividans*, its DNA and amino acid sequence, antibodies raised against such protease and a strain of *S. lividans* deficient in such protease. Protease X has different DNA and amino acid sequences than the proteases described in this application and cleaves different substrates than those described in this application.

A specific recombinant genetic expression system designated CANGENUS™ has been used to ferment and produce a variety of protein products, for example, granulocyte macrophage-colony stimulating factor (GM-CSF), interleukin-3 (IL-3), interleukin-6 (IL-6), and erythropoietin (EPO) (see Canadian Patent Numbers 1,295,563; 1,295,566; and 1,295,567; and U.S. Pat. No. 5,200,327).

Although the CANGENUS™ system has been successful in producing exogenous products, some undesirable proteases produced by expression of endogenous genes deleteriously affect the quality, quantity or stability of exogenous products.

Thus, a need exists to impair the action of these Streptomyces proteases. Among strategies which can be employed to meet this need are the use of inhibitors to inhibit the effect of proteases during the production processes and the use of improved strains which lack such proteases or which have impaired proteases.

Isolation of the protease genes could also be useful in the design of vectors directing the expression and secretion of heterologous proteins from Streptomyces. The promoter and signal sequence of such proteases could be used to enhance and direct the export of heterologous proteins from Streptomyces. The proteases themselves could be usefully employed to remove specific amino acid sequences, peptides or polypeptides from a protein. Furthermore, it would be useful if the level of expression of such proteases could be enhanced through mutation, selection or genetic engineering.

SUMMARY OF THE INVENTION

Streptomyces strains secrete a wide variety of heterologous proteins including GM-CSF, IL-3, IL-6, EPO, TNF, SCF, IL-7 and IL-2. However, proteases of such Streptomyces strains impair the quality and quantity of secreted proteins. Before this invention, persons have strived to improve the quality and quantity of such proteins. This invention meets that goal by (A) inhibiting certain Streptomyces proteases, and (B) providing new Streptomyces strains which lack or have impaired degradative proteases.

To circumvent protein degradation, this invention uses selective inhibitors which are capable of protecting secreted peptides, polypeptides including heterologous protein biopharmaceuticals from degradation by secreted host proteases.

This invention also uses improved strains that have impaired protease production systems, but which are capable of expressing desired products.

This invention relates to the selection of Streptomyces strains with enhanced expression of proteases and the isolation and purification of Streptomyces proteases. Amino acid sequences of the proteases and substantially equivalent sequences are aspects of the present invention. Promoters and signal sequences of such proteases are further aspects of the present invention.

A signal sequence is typically composed of the aminoterminal portion of the unprocessed polypeptide, extending from the amino terminal residue to the beginning of the mature protein sequence. The signal sequence is typically a small peptide which directs the protein to a particular cellular or extracellular location, or for export from the cell, at which point the signal peptide is preferably cleaved.

This invention also relates to nucleotide sequences encoding impaired proteases and the use of those sequences to increase the quality, quantity or stability of peptides and polypeptides including heterologous proteins secreted from a host transformed with a vector containing the nucleotide sequence for such impaired proteases.

This invention also relates to the use of the isolated and purified proteases to cleave peptides or polypeptides or to cleave amino acids, peptides or polypeptides from a protein.

A further aspect of this invention is the construction of an inhibitor comprising, L-alanyl-L-prolyl-L-alanine chloromethylketone, its salts and analogs. Another aspect of this invention is the use of the inhibitor L-alanyl-L-prolyl-L-alanine chloromethylketone to inhibit a tripeptidyl aminopeptidase derived from Streptomyces.

This invention also relates to a method of increasing the quality, quantity or stability of peptides or polypeptides including heterologous proteins secreted from a host by using an inhibitor comprising, L-alanyl -L-prolyl -L-alanine chloromethylketone.

Another aspect of this invention is the construction of an improved Streptomyces strain having impaired expression of at least one endogenous protease. The strain is capable of expressing an exogenous gene product. The impaired expression decreases the activity or quantity of endogenous protease resulting in an increase in quality, quantity or stability of exogenous gene product.

Impaired expression is accomplished by deleting or mutating one or more nucleotides in the sequence encoding for a protease, or by deleting and substituting nucleotides in the sequence encoding for a protease.

A further aspect of this invention is a vector which has a recombinant DNA sequence encoding a Streptomyces protease or an impaired Streptomyces protease and a regulatory sequence for expression of the coding sequence. The regulatory sequence includes a promoter sequence, an operator sequence, a transcriptional-start sequence, a ribosome-binding site sequence, and a signal sequence.

Another aspect of this invention is a method of fermentation using genetically engineered Streptomyces host cells with impaired protease activity, The method includes the steps of: (a) constructing Streptomyces host cells with impaired protease activity and which express a desired exogenous product under suitable conditions; and (b) placing the cells in suitable conditions for expression of the desired product. The method of fermentation can be used to express GM-CSF, IL-3, IL-6, EPO, TNF, SCF, IL-7 and IL-2 or any other desired product.

In another aspect, this invention envisions introducing the DNA sequences encoding such proteases into recombinant vectors which, when transformed into suitable host strains, enable the production of heterologous proteases having the biological activity of the wild type proteases. Both prokaryotic and eucaryotic hosts may serve as hosts for producing such proteases.

Further aspects of this invention are kits containing (a) isolated and purified proteases derived from Streptomyces, or (b) inhibitors of proteases derived from Streptomyces.

A kit for ELISA would consist of:

1) A protease, Tap, covalently linked to biotin or other carrier capable of participating in the formation of an antigen-antibody complex (example: Tap covalently linked to a goat antirabbit IgG);

2) A substrate, APA-pNA or APA-AMC, which would be cleaved by the Tap bound in the antigen-antibody complex thereby generating an increase in light absorbance at 405 nm with APA-pNA as substrate or an increase in fluorescence when an excitation/emission near 380/460 nm is employed with APA-AMC as substrate.

In this application, the following terms have the following meanings:

"Heterologous" or "exogenous" refers to nucleic acids, amino acids, peptides, polypeptides or proteins which do not naturally occur in a particular host cell. "Host cell" means a prokaryotic or eucaryotic cell, strain, specie or genera, suitable for introduction and for expression of heterologous DNA sequences. Such DNA sequences may be modified for expression in a particular host as a DNA sequence containing (i) codons preferably used by the host, or (2) promoters, operators, ribosome binding sites and terminator sequences used by the host.

"Substantially equivalent" in reference to a sequence means a sequence, whether natural or engineered, which has additions, deletions, or substitutions compared to the sequence of another protease described or claimed in this application and which produces a functionally similar protease to the protease described or claimed.

"Wild type" means the activity characteristic of a host cell in which endogenous proteases are not impaired. Illustrative embodiments of impaired proteases include a host strain in which DNA at the chromosomal locus encoding a protease in a Streptomyces strain is deleted. This strain exhibits a significantly reduced level of activity or no activity when compared to a wild type Streptomyces strain.

"Impaired" means that the activity and/or the quantity of protease produced by a nucleotide sequence is impaired compared to a "wild type" nucleotide sequence, that is, a sequence not altered to affect expression as it generally occurs in the host species and strain.

"Endogenous protease" means a protease that is able to cleave one or more of the substrates referred to in this application.

"Selective inhibitor" means an inhibitory molecule that inhibits a secreted protease, or a protease released into the fermentation as a result of cell breakage.

| | |
|---|---|
| -3 = | protein from which three amino acid residues have been removed from the N-terminus of the protein |
| -4 = | protein from which four amino acid residues have been removed from the N-terminus of the protein |
| -6 = | protein from which six amino acid residues have been removed from the N-terminus of the protein |
| aa = | amino acid |
| AAPA-pNA = | L-alanyl-L-alanyl-L-prolyl-L-analine p-nitroanilide |
| AA-pNA = | L-alanyl-L-alanine p-nitroanilide |
| AMC = | 7-amino-4-methylcoumarin |
| APACMK = | L-alanyl-L-prolyl-L-alanine chloromethylketone |
| APA-AMC = | L-alanyl-L-prolyl-L-alanine 7-amino-4-methylcoumarin |
| APF-bNA = | L-alanyl-L-prolyl-L-phenylalanine beta-naphthylamide |
| APA-pNA = | L-alanyl-L-prolyl-L-alanine p-nitroanilide |
| APM-pNA = | L-alanyl-L-prolyl-L-methionine p-nitroanilide |
| A-pNA = | L-alanine p-nitroanilide |
| APS-bNA = | L-alanyl-L-prolyl-L-serine beta-naphthylamide |
| bNA = | beta-naphthylamide |
| Boc = | N-t-butoxycarbonyl |
| Boc-AAPA-pNA = | N-t-butoxycarbonyl L-alanyl-L-alanyl-L-prolyl-L-alanine p-nitroanilide |
| Boc-APARSPA-bNA = | L-alanyl-L-prolyl-L-analyl-L-arginyl-L-seryl-L-prolyl-L-alanine beta-napthylamide |
| D-FPR-bNA = | D-phenylalanyl-L-prolyl-L-arginine beta-napthylamide |
| DMSO = | dimethyl sulphoxide |
| D-PFR-pNA = | D-prolyl-L-phenylalanyl-L-arginine p-nitroanilide |
| EDTA = | Ethylenediaminetetraacetic acid |
| ELISA = | enzyme-linked immunosorbent-assay |
| FPLC = | fast protein liquid chromatography |
| GPL-bNA = | Glycyl-L-prolyl-L-leucine beta-napthylamide |
| GP-pNA = | Glycyl-L-proline p-nitroanilide |
| GPM = | Glycly-L-prolyl-L-methionine |
| HEPES = | N-2-hydroxyethylpiperazine-N'-2-ethanesulphonic acid |
| HOHD = | 2-hydroxy-6-oxohepta-2,4-dienoate |
| L-pNA = | L-leucine p-nitroanilide |
| MNNG = | N-methyl-N'-nitro-N-nitrosoguanidine |
| N-Ac = | N-acetyl |
| N-Ac-APA-pNA = | N-acetyl-L-alanyl-L-prolyl-L-alanine p-nitroanilide |
| N-Bz = | N-benzoyl |
| N-Bz-R-pNA = | N-benzoyl-L-arginine |
| N-Bz-VGR-pNA = | N-benzoyl-L-alanyl-glycyl-L-arginine p-nitroanilide |

-continued

| | |
|---|---|
| nt = | nucleotide |
| ORF = | open reading frame |
| PAGE = | polyacrylamide gel electrophoresis |
| PMSF = | phenylmethanesulfonyl fluoride |
| pNA = | p-nitroaniline |
| P-pNA = | L-proline p-nitroanilide |
| R-pNA = | L-arginine p-nitroanilide |
| SDS = | sodium dodecyl sulphate |
| S-bNA = | L-serine beta-napthylamide |
| SPA-bNA = | L-seryl-L-prolyl-L-alanine beta-napthylamide |
| Ssp = | Streptomyces Subtilisin-like protein |
| ssp = | gene encoding Ssp |
| Tap = | tripeptidyl aminopeptidase-S |
| tap = | gene encoding Tap |
| TSB = | Trypticase Soya Broth |

DESCRIPTION OF DRAWINGS

FIG. 2. Cleavage of Synthetic Substrates by S. dividans Fermentation Broth.

FIG. 8. (B) The tap-deletion clones.

FIG. 8. (C) The tap-integration clones.

FIG. 11. Conversion of the substrate of intact GM-CSF to its "-3 form" upon incubation with fermentation culture supernatants from cells carrying the tap clones.

FIGS 12A–12C. Nucleic acid and encoded amino acid sequences of the tripeptidyl aminopeptidase (tap) gene SEQ ID NOS 1 and 2).

FIG. 13. Amino acid sequence similarity between Tap (residues 199–228 of SEQ ID NO:2) and HOHD (SEQ ID NO:11) from *Pseudomonas putida* F1.

FIGS 20A–20C. Nucleic acid and encoded amino acid sequences of the cloned P5-4 DNA (SEQ ID NOS 3 and 4).

FIG. 21. Comparison of the predicted amino acid sequence encoded by the P5-4 DNA (SEQ ID NO:4) and that of subtilisin BPN (SEQ ID NO:12)

FIGS 25A–25C. Nucleic acid and predicted amino acid sequence of P5-6 DNA.

FIG. 26. Comparison of the predicted amino acid sequences for the Tap (SEQ ID NO:2) and P5-6-encoded putative protein (SEQ ID NO:8).

FIGS 29A–29C. Nucleic acid and predicted amino acid sequence of P8-2 (SEQ ID NOS 5 and 6).

DETAILED DESCRIPTION OF PREFERRED EMBODIMENTS

Figure 1A:
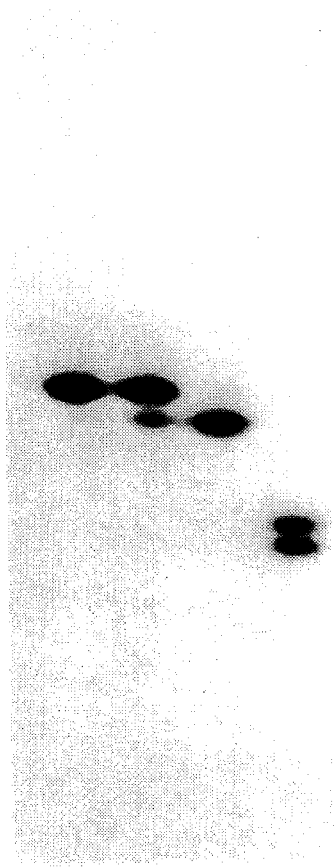
FIGS 1A–1B. Degradation of GM-CSF and IL-3 by S. lividans Fermentation Broth.

A previously unknown protease, a tripeptidyl aminopeptidase derived from Streptomyces ("Tap"), has been identified, isolated, and characterized. The enzyme was purified by pH precipitation and chromatography. The proteolytic activity was followed both by assaying the degradation of GM-CSF and by the release of the yellow p-nitroaniline molecule from the specially synthesized substrate L-alanyl-L-prolyl-L-aniline p-nitroanilide (APA-pNA). The pure protease had an apparent molecular weight of 55,000 daltons as determined by SDS-PAGE. The amino terminal sequence of the purified protease was determined by Edman degradation of the protein after purification.

A selective inhibitor of Tap, L-alanyl-L-prolyl-L-alanine chloromethylketone (APACMK), has been designed, synthesized, and applied to inhibit this protease. APACMK stopped the release of p-nitroaniline from APApNA by Tap. APACMK stopped the cleavage of GM-CSF by Tap. In fermentations of GM-CSF, APACMK prevented cleavage of GM-CSF by Tap during fermentation but did not significantly retard the rate of cell growth.

A tripeptidyl aminopeptidase gene (tap) was cloned from S. lividans 66 by screening for overexpression of endogenous enzyme activity using the chromogenic substrate GPL-bNA as a liquid overlayer on colonies of Streptomyces growing on agar medium. When these colonies were selected on the basis of activity they exhibited according to the chromogenic assay disclosed herein, and were grown in liquid culture, a major secreted protein with an estimated apparent molecular weight of 55,000 daltons as determined by SDS-PAGE was identified in the culture supernatant. The appearance of this protein was correlated with elevated levels of Tap activity in liquid assays using GPL-bNA and other substrates, suggesting that Tap presence was causative of the activity detected by the assay.

The amino terminal sequence of the overexpressed protein was determined by various procedures, e.g., by Edman degradation of the protein after purification by SDS-PAGE. The amino terminal sequence of the overexpressed protein matched the amino terminal sequence of Tap isolated from fermentations of the host strain. The tap gene was localized within the cloned DNA fragment by monitoring the Tap activity of strains containing various subclones and deletion clones derived from the original clones.

DNA sequences adjacent to the tap gene were used to construct a subclone in which the tap gene was precisely deleted. This deletion clone was then substituted into the chromosomes of S. lividans 66 strains by homologous recombination to replace the wild type tap locus with a mutant gene which encoded a defective Tap.

Disruption of the chromosomal tap gene in S. lividans resulted in a reduction in Tap activity of at least tenfold, indicating that this enzyme was responsible for the majority of the activity observed in S. lividans strains. Deletional inactivation of the gene encoding a second protease (Ssp) resulted in a further reduction in the ability of cell-free broth to hydrolyse APA-bNA. Strains carrying such chromosomal DNA deletions generally exhibited significantly lower Tap activity (FIG. 22), reducing the degradation of proteins produced by genetically engineered host cells, and enabling higher recovery of secreted proteins from the culture supernatant produced by fermentation of the host strain in liquid medium.

I. Prokaryotic Tripeptidyl Aminopeptidases

Tripeptidyl aminopeptidase

Degradation products were found in fermentations producing GM-CSF and IL-3.

Figure 1B:

FIG. 1 shows the degradation products derived from GM-CSF and IL-3. (A) shows a native gel electrophoresis analysis of GM-CSF degradation. Lane 1 shows intact, full length GM-CSF. Lane 2 shows GM-CSF from S. lividans fermentation. Lane 3 shows degraded isolated GM-CSF (–3). Lane 4 shows a mixture of isolated GM-CSF (–4) and GM-CSF (–6). (B) shows an analysis of IL-3 degradation by electrophoresis on an SDS-urea gel (6M urea in the polyacrylamide gel). A 20-fold concentrated fermentation broth was prepared by subjecting a cell-free fermentation broth to ultrafiltration employing a membrane with a 10 kDa cutoff. Lane 1 shows IL-3 before incubation. Lane 2 shows IL-3 after 2 hours incubation at 32° C.

The major degradation products were isolated and analyzed by amino acid sequencing. This analysis indicated that the major degradation products (FIG. 1A, Lane 3 and FIG. 4, Lane 5) were produced by the removal of the N-terminal tripeptides, APA and APM, from GM-CSF and IL-3, respectively.

Based upon this information, the molecule APA-pNA was synthesized as a potential substrate. This and several commercial substrates were employed in a survey of proteolytic activities in S. lividans fermentation broths.

FIG. 2 is the quantification of proteolytic activities in the fermentation broth as measured with synthetic substrates. The assays were conducted in 50 mM Tris-HCl, pH 8.0 with 0.8 mM substrate incubated at 37° C. The change in absorbance at 405 nm was measured after 1, 2, and 4 hours of incubation. The results are reported as micromoles of p-nitroaniline released in 1 hour by 1.0 ml of fermentation broth.

1=APA-pNA; 2=D-PFR-pNA; 3=L-pNA; 4=R-pNA; 5=P-pNA; 6=AP-pNA; 7=A-pNA; 8=AA-pNA; 9=N-Benzoyl-R-pNA; 10=Boc-AAPA-pNA; 11=N-Acetyl-APA-pNA; 12=N-Benzoyl-Y-pNA.

As shown in FIG. 2, APA-pNA cleaving activity was greater than any other activity measured in the broth. This data suggested that a single protease, a tripeptidyl peptidase, not a group of several enzymes, was responsible for the activity. Additionally, the lack of activity towards the amino-blocked analog, N-Ac-APA-pNA, indicated that the enzyme responsible was an aminopeptidase.

Figure 3A:
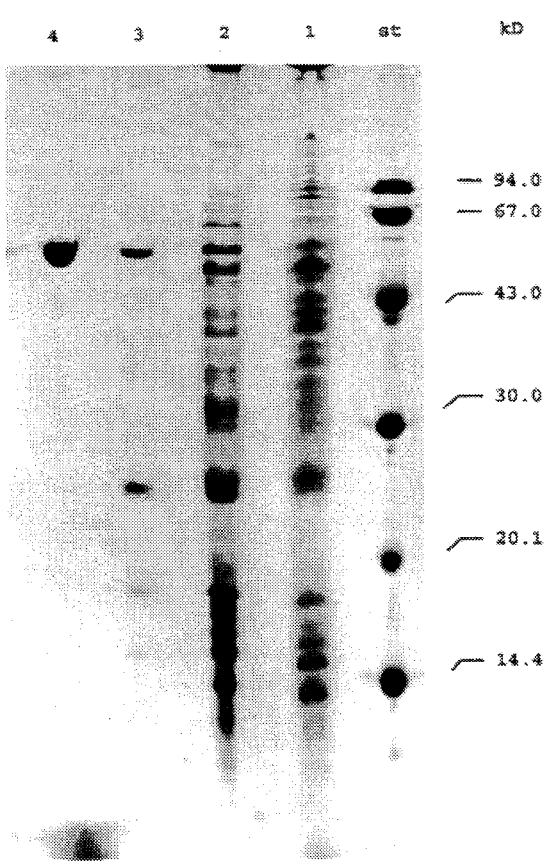
FIGS 3A–3B. Demonstration of Purification of Tap.
Figure 3B:
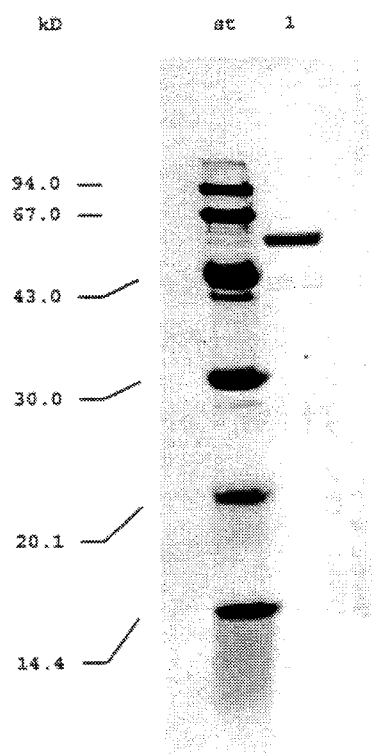

The wild-type protease was purified after cell removal and concentration of the fermentation broth by ultrafiltration. The method of purification is described in Example 1. To purify Tap FIGS 3A–3B, approximately 20 ug of protein were denatured under reducing conditions and analyzed by SDS-PAGE on 10% polyacrylamide gel. (A) represents purification of wild-type Tap. St=Molecular weight standards; Lane 1=Broth obtained after cell removal and concentration of broth by ultrafiltration through a 10 kDa membrane; Lane 2=Redissolved pH 4.0 precipitate; Lane 3=Q-Sepharose chromatography pool; Lane 4=Phenyl-Sepharose chromatography pool. (B) represents purified Tap from the overproducer strain. St=Molecular weight standards; Lane 1=Tap purified from fermentation of the overexpressor (P3-5) strain.

The pure protease cleaved the N-terminal tripepride from GM-CSF and cleaved the N-terminal tripepride from IL-3. When GM-CSF or IL-3 were used as a substrate, the cleaved products produced by the pure Tap were identical to the major degradation products found in Streptomyces fermentations. These assays are described in Example 2.

As described in Example 2, Tap releases p-nitroaniline from APApNA. The enzyme was also active when APM-pNA, APA-AMC, APS-bNA, GPL-bNA, and SPA-bNA were used as substrates. It did not release the reporter group from A-pNA, L-pNA, P-pNA, R-pNA, S-bNA, N-Bz-R-pNA, AA-pNA, GP-pNA, D-PFR-pNA, N-Ac-APA-pNA, N-Bz-VGR-pNA, AAPA-pNA, Boc-AAPA-pNA, and Boc-APARSPA-bNA. The enzyme only released the reporter group from substrates with a free amino terminal. The enzyme cleaved only tripepride units since no reporter release was seen with mono-, di-, or tetra-amino acid substrates.

The effect of pH on the activity of Tap has been examined. When APA-pNA was used as a substrate, the enzyme was active from between pH 5.0–9.5 with the maximal activity obtained from between 8.0–8.5. The enzyme cleaved GM-CSF from between pH 4.0–10.0 with greatest activity from between 5.0–9.0. The broad maximum for GM-CSF reflected the high sensitivity of this substrate to Tap. The enzyme cleaved IL-3 from between pH 5.0–9.0 with maximal activity attained between 7.0 and 8.5.

An inhibitor survey indicated that tripeptidyl aminopeptidase was a serine protease. Table I shows the inhibition of Tap activity by various protease inhibitors. The protease and inhibitor were preincubated for 15 minutes at 22° C. Substrate was added and the mixture was incubated at 37° C. Activity was measured by monitoring the change in absorbance at $\lambda$=405 nm.

TABLE 1

Inhibition of TAP in the APA-pNA Assay

| Sample | Concentration | Residual Activity |
|---|---|---|
| Enzyme only | — | 100 |
| PMSF | 1.6 mM | 7 |
| HgCl$_1$ | 0.1 mM | 99 |
|  | 1.0 mM | 93 |
| CaCl$_2$ | 1.0 mM | 96 |
|  | 10 mM | 97 |
| CoCl$_2$ | 1.0 mM | 98 |
|  | 10 mM | 97 |
| EDTA | 1.0 mM | 95 |
|  | 10 mM | 95 |
| IDA | 1.0 mM | 82 |
| DTT | 1 mM | 86 |
| DTT + EDTA | 1 mM + 10 mM (respectively) | 97 |
| Elastatinal | 0.1 mM | 97 |
| Chymostatin | 0.1 mM | 98 |
| Pepstatin | 0.1 mM | 95 |
| Benzamidine | 10 mM | 94 |

The enzyme was inhibited by the serine protease inhibitor, phenylmethanesulfonyl fluoride (PMSF). Treatment of Tap with PMSF inhibited cleavage of GM-CSF, IL-3, and APA-PNA.

Figure 4:
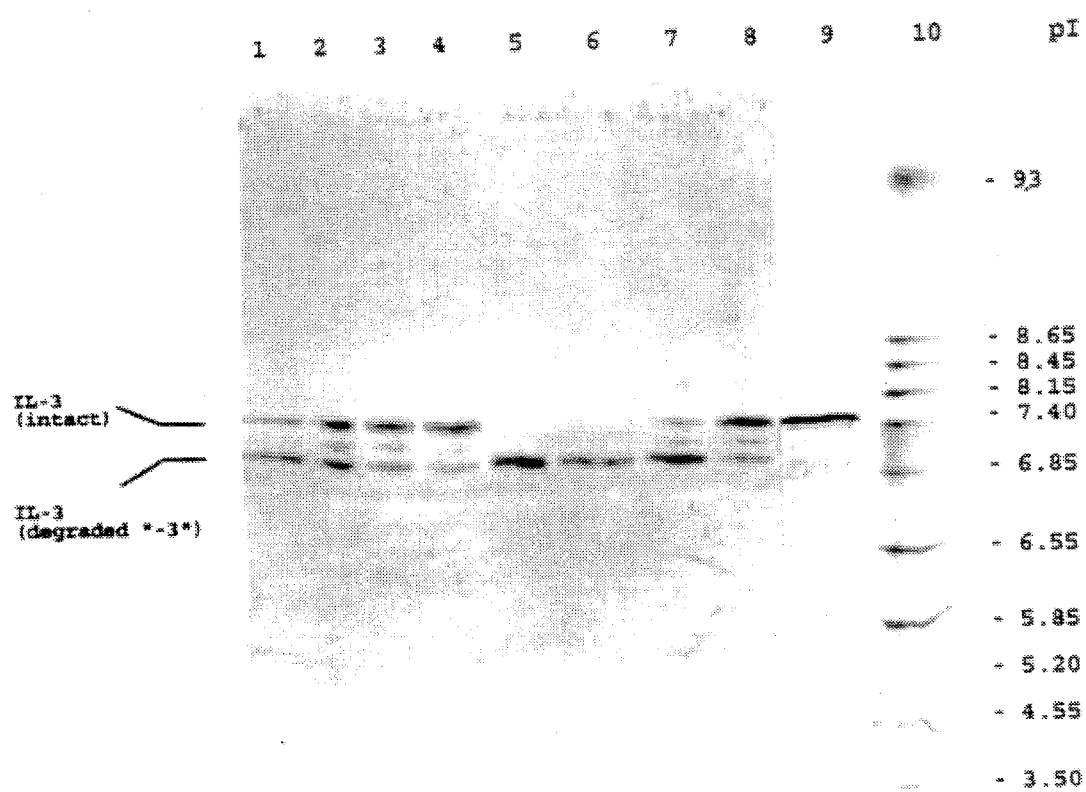
FIG. 4. Inhibition of IL-3 Cleavage by Tap After PMSF Treatment.

The inhibition of IL-3 cleavage is demonstrated in FIG. 4 and the inactivation protocol is described in Example 3. Lanes 1–4 show the incubation of IL-3 with TAP-S that has been treated with PMSF. Lane 1=4 hrs; Lane 2=2 hours; Lane 3=1hr.; Lane 4=0 hours. Lanes 5–8 show the incubation of IL-3 with uninhibited Tap. Lane 5=4 hrs.; Lane 6=2 hrs.; Lane 7=1 hrs.; Lane 8=0 hrs. Lane 9 is a human carbonic anhydrase marker, pI=7.4. Lane 10 contains pI markers. As can be seen in Lanes 5–8 of FIG. 4, the IL-3 (pI=7.4) is completely converted to the −3 form (pI=7.1) by Tap within 2 hours. Lanes 1–4 show that with PMSF treatment, intact IL-3 is clearly detected after 4 hours. The enzyme is not affected by sulfhydryl reagents, chelators or aspartyl protease inhibitors (Table I).

Table II shows the N-terminal sequence of the isolated wild-type Tap. The sequence data was obtained as described in Example 4.

TABLE II

N-Terminal Sequence of Isolated Tap

| Cycle | Amino Acid, Wild-Type |
|---|---|
| 1 | Asp |
| 2 | Gly |
| 3 | His |
| 4 | Gly |
| 5 | His |
| 6 | Gly |
| 7 | Arg |
| 8 | Ser |
| 9 | Trp |
| 10 | Asp |
| 11 | Arg |
| 12 | Glu |
| 13 | Ala |
| 14 | Arg |
| 15 | Gly |

II. L-Alanyl-L-Prolyl-L-Alanine Chloromethylketone (APACMK)

The synthesis of APACMK is described in Example 5.

Figure 5:
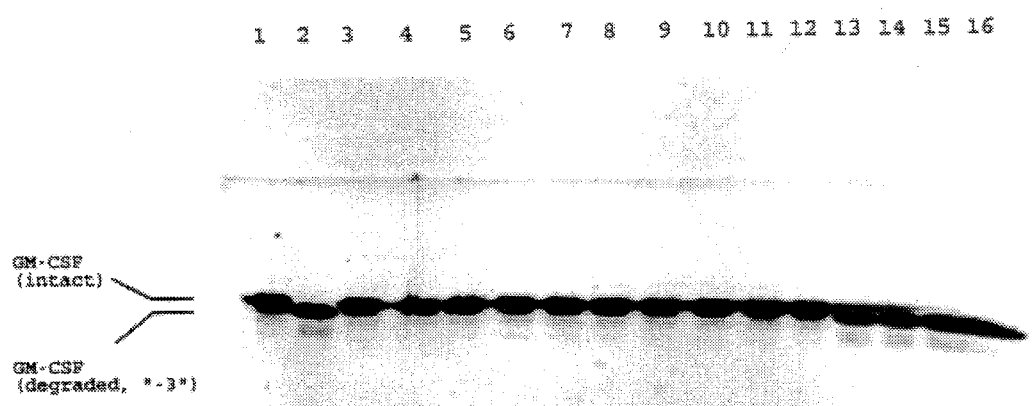
FIG. 5. Inhibition of Tap by APACMK: GM-CSF Assay.
Figure 6:
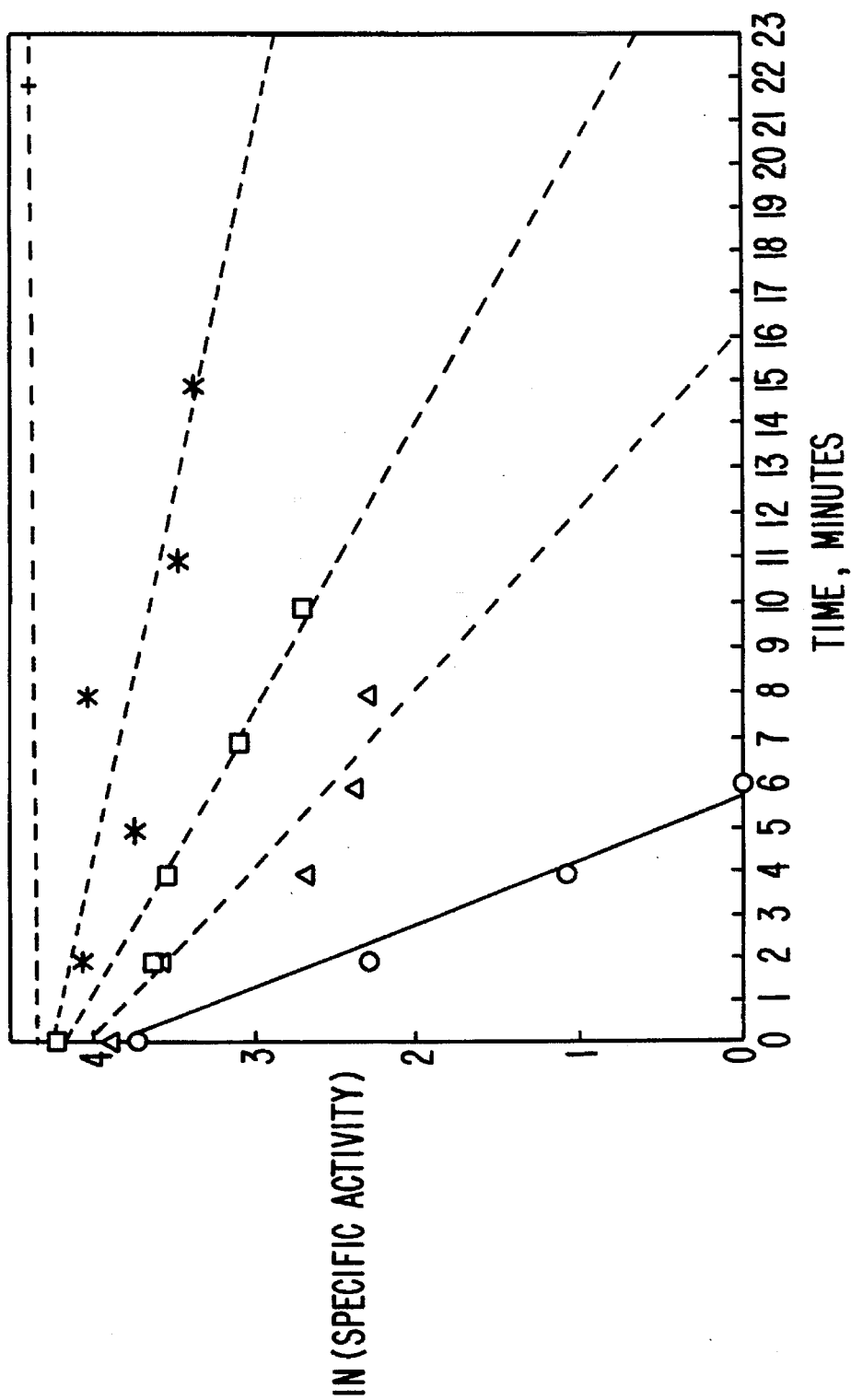
FIG. 6. Inhibition of Tap by APACMK: APA-pNA Assay.

APACMK inactivated Tap at very low concentrations when residual activity was assayed with GM-CSF or APA-pNA respectively (FIGS. 5 and 6).

FIG. 5 shows the titration of Tap with APACMK as assayed with GM-CSF. The assay was performed as described in Example 7. The Tap concentration in the assays was 5 nM. Lane 1=GM-CSF standard; Lane 2=GM-CSF after digestion with Tap in the absence of APACMK; Lanes 3 and 4=150 uM APACMK; Lanes 5 and 6=15 uM APACMK; Lanes 7 and 8=1.5 uM APACMK; Lanes 9 and 10=150 nM APACMK; Lanes 11 and 12=15 nM APACMK; Lanes 13 and 14=1.5 nM APACMK; Lanes 15 and 16=150 pM APACMK.

FIG. 6 shows the inactivation of Tap by various APACMK concentrations when assayed with APA-pNA as substrate. The concentration of Tap in the inactivations was 1.0 uM. The inactivation and assay were conducted as described in Example 8. In FIG. 6, (O)=2.70 uM APACMK; (Δ)=2.16 uM APACMK; (□)=1.73 uM APACMK; (*)=1.38 uM APACMK; (+)=No APACMK.

The inhibitor APACMK yielded $K_i$=3.3 uM and $k_{inact}$= 0.14 min$^{-1}$ with >99% inactivation within 6 minutes at 0° C. at an inhibitor concentration of 2.7 uM and an inhibitor/ enzyme molar ratio of 2.7 (FIG. 6). The methods employed are described in Examples 6, 7, and 8.

Figure 7:
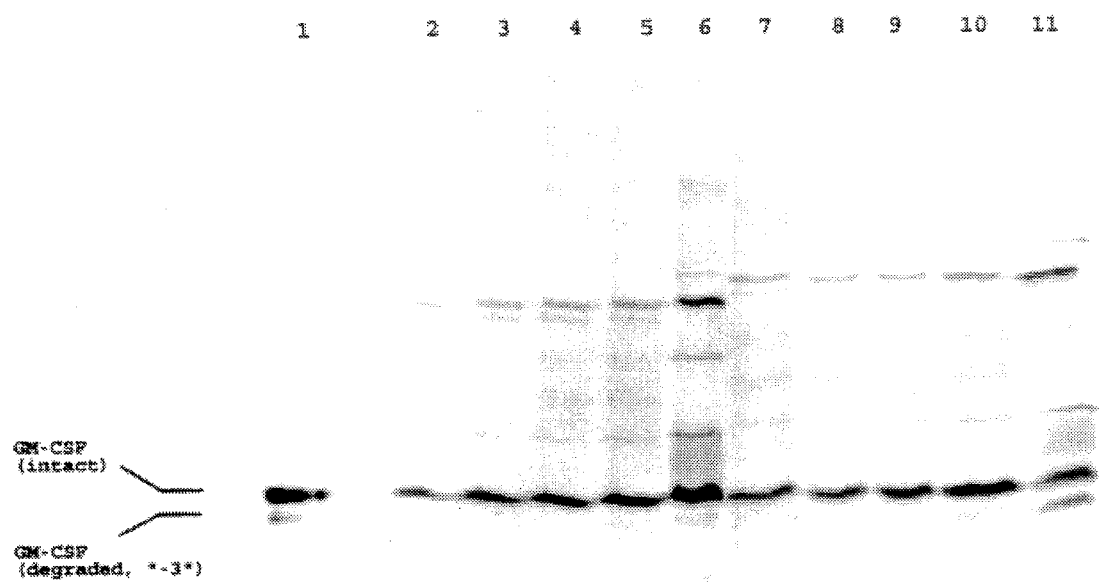
FIG. 7. Inhibition of Degradation of GM-CSF During Fermentation in the Presence of APACMK.

FIG. 7 demonstrates the inhibition of Tap by APACMK during the fermentation of *S. lividans* grown in the presence and absence of 10 uM APACMK as described in Example 9. When APACMK and GM-CSF were added to the protease-containing broth from *S. lividans* fermentations, the formation of the GM-CSF(−3) degradation product was inhibited. Lane 1=Standard containing GM-CSF and GM-CSF (−3). Lanes 2–6 show a fermentation in the presence of 10 uM APACMK. Lane 2=25 hours growth; Lane 3=27 hours growth; Lane 4=29 hours growth; Lane 5=31 hours growth; Lane 6=48 hours growth. Lanes 7–11 show a fermentation without APACMK. Lane 7=25 hours growth; Lane 8=27 hours growth; Lane 9=29 hours growth; Lane 10=31 hours growth; Lane 11=48 hours growth. GM-CSF degradation was analyzed by native gel electrophoresis.

III. Nucleotide Sequence Encoding Streptomyces Proteases and Amino Acid Sequence of Such Proteases Methods of identifying and isolating the DNA encoding Tap are described in Example 10.

Figure 8:
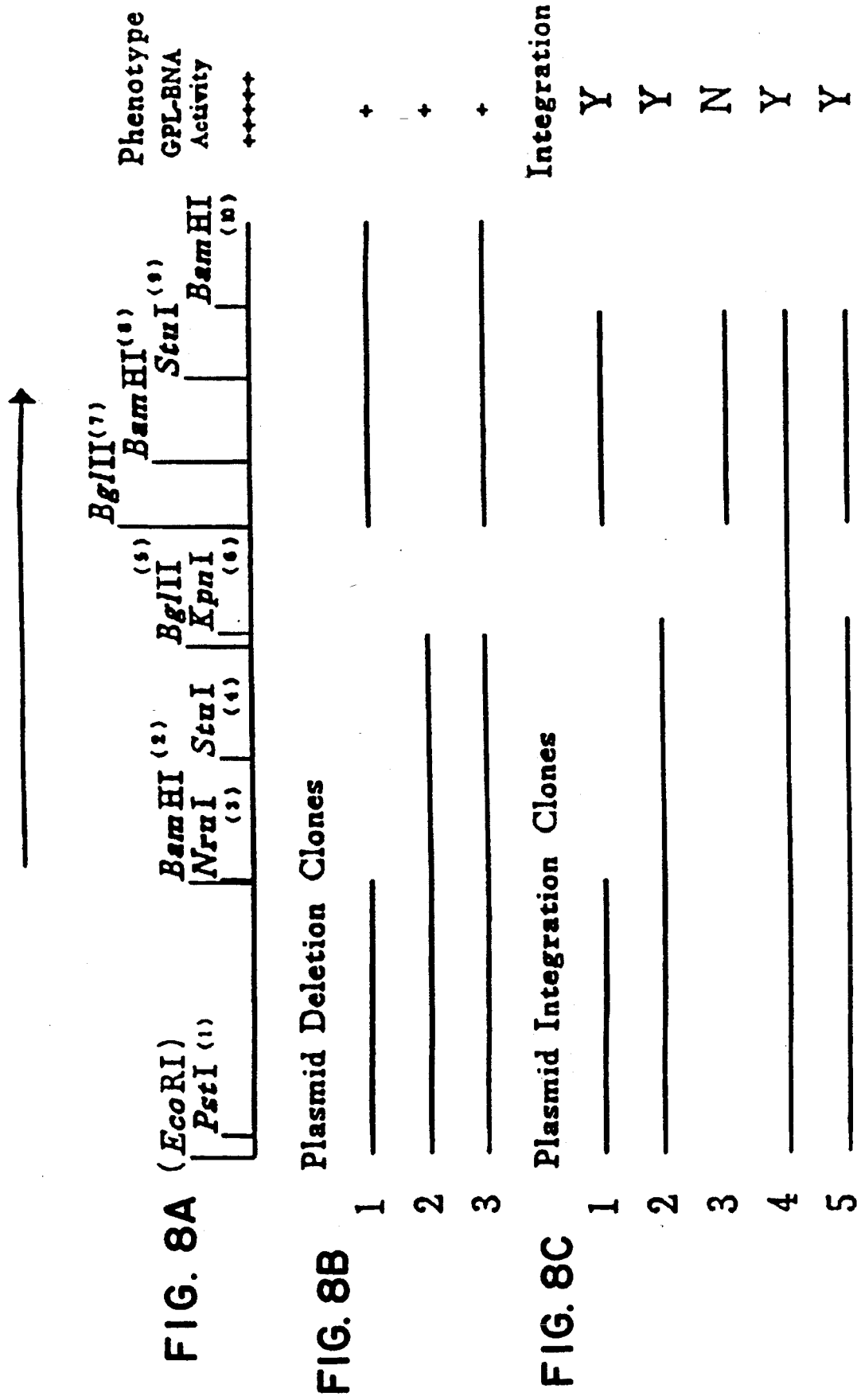
FIG. 8. (A) Common restriction map for tap-containing plasmid DNA isolated from clone P3-13 (and P3-5).

FIG. 8 is a restriction enzyme site map of cloned tap DNA. FIG. 8(A) The location and direction of potential protein encoding regions is shown by arrows, of which the larger represents the tap gene. Phenotype in the GPL-bNA hydrolysis agar plate assay is shown qualitatively as the number of + signs judging red colour developed on the colonies. The EcoRI site shown in parentheses was present in the pSS12 vector adjacent to the BamHI cloning site. FIG. 8(B) None of the three deletion clones shown produced any more red colour in colonies than did the pSS12 control plasmid and they were scored as "+" due to the background level of hydrolysis from the chromosomally-encoded tap gene in the *S. lividans* 66 host. (C) The DNA fragments shownwere subcloned into the integration plasmid and used to transform protoplasts of *S. lividans* 66 to thiostrepton resistance. Clone numbers 1, 2, 4 and 5 all produced thiostrepton-resistant transformants, whereas clone 3 did not presumably due to the small size of the homologous DNA fragment in this clone.

Figure 9:
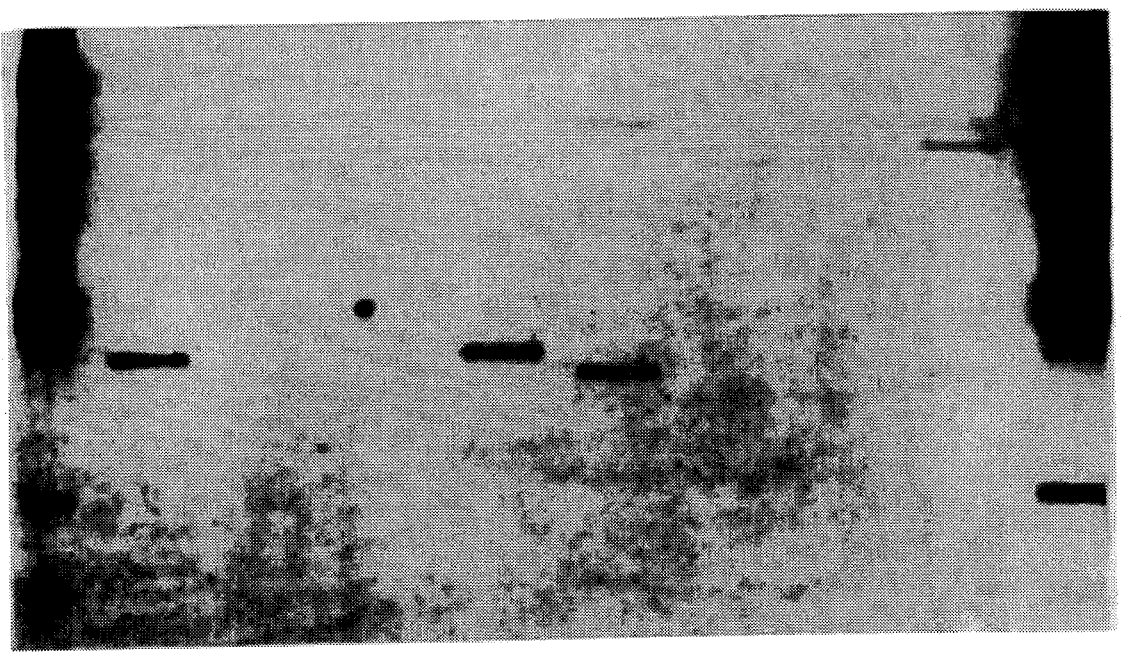
FIG. 9. Southern hybridization analysis of chromosomal DNA from S. lividans 66 and S. lividans MS7, using DNA from the P3-13 plasmid (0.3 kb BglII) as a probe.

FIG. 9 is a Southern hybridization analysis of the chromosomal tap locus in *Streptomyces lividans* 66 and deletion mutant strains. The DNA was digested with BamHI or StuI and transferred to a nylon membrane (Hybond, Amersham). Using a $^{32}$P-labelled probe for the BglII fragment internal to the tap gene resulted in a strong band of hybridisation at approximately 1.8 kbp in the BamHI digests (lanes 2 and 5) and two bands in the StuI digests (lanes 6 and 9) for both the *S. lividans* control and colony #3 indicating that this DNA fragment was present in both strains. However, no hybridizing bands were observed for colonies 2 and 3 (lanes 3, 4, 7 and 8) confirming the loss of the 0.3 kbp BglII fragment. Lanes 1 and 10 show a Lambda / HindIII molecular weight marker.

Figure 10:
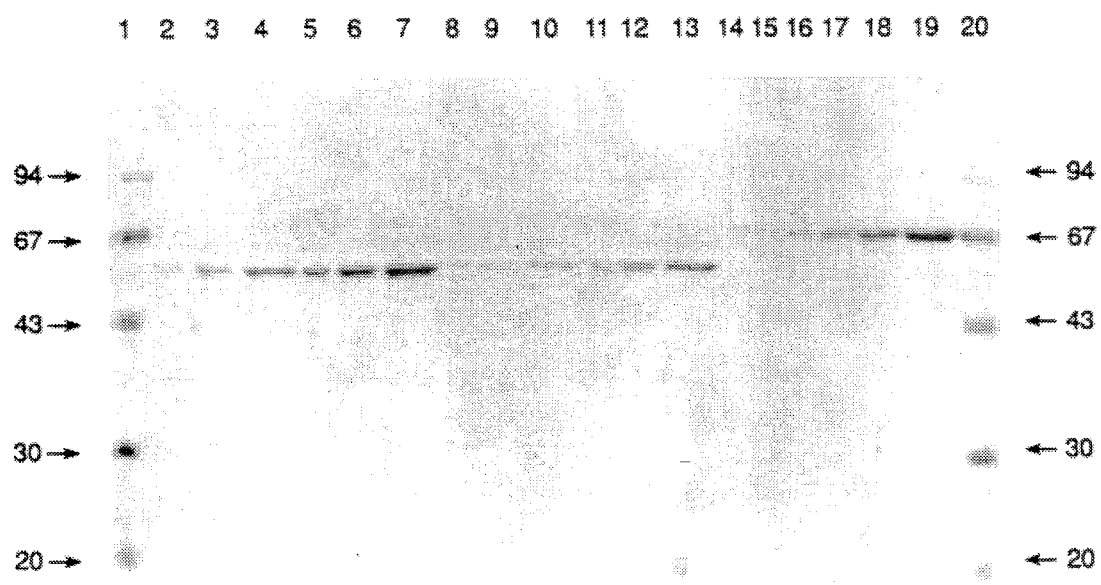
FIG. 10. Profiles of extracellular proteins from S. lividans 66 strains carrying the P3-5 and P3-13 clones; the profiles were generated by SDS-PAGE and the gels stained with Coomassie Brilliant Blue.

FIG. 10 is an SDS-PAGE analysis of cell-free broth supernatants from cultures of *S. lividams* 66 carrying the P3-13 or P3-5 plasmids. Cultures were sampled at 23 or 29 hours after inoculation into TSB medium.

FIG. 11 is a conversion of exogenously added, purified full length GM-CSF degraded to the −3 form upon incubation with fermentation culture supernants from culture samples carrying the tap clones.

The nucleic acid sequence (SEQ ID NO:1) for the *S. lividans* tap gene is shown in FIGS 12A–12C. The deduced amino acid sequence (SEQ ID NO:2) is shown for each codon.

Serine proteases possess a nucleophilic serine which attacks the carbonyl of the peptide bond to catalyze hydrolysis (White, Handler and Smith, 1973). Although the nucleophilic serine modified by PMSF has not been isolated, a homology study of the DNA sequence can identify potential candidates. The protease is encoded by the DNA sequence (SEQ ID NO:1) shown in FIGS 12A–12C. The amino acid sequence derived from the DNA sequence (SEQ ID NO:2) is also shown.

The most likely active site serine residue was identified by its homology with that described for a serine esterase enzyme characterized in a Pseudomonas species by the conserved amino acid sequence motif G X S X G (SEQ ID NO:9) (Menn et al., 1989). The homologous sequence in Tap would be GVSYG (residues 243–247 204–208 of SEQ ID NO:2).

FIG. 13 is the amino acid sequence similarity between Tap (residues 19–228 of SEQ ID NO:2) and the HOHD from *Pseudomonas putida* F1 (SEQ ID NO:11) (. The amino acid sequences were compared using the BLAST (Altschulet al) program to screen the protein sequence databases.

The first 15 residues of the N-terminal of the isolated wild-type protease (Table II) have been determined and identically matched amino acids 40–54 derived from the DNA sequence (FIGS 12A–12C (SEQ ID NOS 1and 2). Residues −39 to −4 appear to be a signal peptide. An autolyric tripepride cleavage removing APA after signal peptide removal would yield the N-terminal found for the secreted protease.

Table III shows the amino acid composition of the wild-type Tap. The amino acid composition derived from the corresponding portion of the tap gene DNA sequence (FIGS 12A–12C, SEQ ID NOS 1 and 2) is shown for comparison. The composition data was obtained as described in Example 4.

The small differences in composition may be attributable to low level impurities in the enzyme sample. The method of analysis for the wild type enzyme is described in Example 4.

The N-terminal of the protease from the overproducer (P3-5) (Example 13) matches the sequence of the N-terminal of the wild-type enzyme. Both the isolated wild-type and isolated overproducer proteases had an apparent molecular weight of 55,000 daltons as determined by SDS-PAGE (FIG. 3). These factors indicated that the wild-type protease and the P3-5 overproduced protease were the same enzyme.

A further embodiment of this invention relates to the use of strains, containing specific impairments in their capability to

TABLE III

| Amino Acid | Mole percentage | |
|---|---|---|
| | Protein | DNA |
| Asp + Asn | 13.6 | 12.4 |
| Glu + Gln | 10.9 | 7.6 |
| Ser | 4.7 | 4.7 |
| Gly | 10.0 | 8.9 |
| His | 2.2 | 2.3 |
| Arg | 7.4 | 7.4 |
| Thr | 6.3 | 6.3 |
| Ala | 14.3 | 14.3 |
| Pro | 7.2 | 7.2 |
| Tyr | 3.9 | 3.8 |
| Val | 6.4 | 7.6 |
| Met | 1.2 | 1.3 |
| Ile | 2.3 | 3.0 |
| Leu | 5.6 | 6.3 |
| Phe | 1.7 | 2.5 |
| Lys | 2.5 | 4.4 | produce secreted proteases, and the isolation and purification of other proteases which cleave substrates such as APAbNA and which also exist in the wild type strain but are expressed at much lower levels than Tap. Methods are described in Examples 20–23 to identify the genes encoding such minor proteolytic activities. It would be extremely difficult to purify such proteases from the wild type strain whereas the methods described here are rapid and simple. One protease (designated Ssp) having significant amino acid sequence homology with the B. subtilis protein Subtilisin BPN was identified by virtue of its ability to cleave APA-bNA using the agar plate assay screening method. Furthermore, deletion of this gene from the S. lividans chromosome in a strain in which the Cap gene had already been inactivated resulted in an incremental reduction in the APA-pNA hydrolyric capability of the strain.

Another protease gene was identified and shown to encode a protease which catalysed the hydrolysis of APA-pNA and also showed a significant amino acid sequence homology to that of the Tap. Particularly strong sequence conservation was noticed around the putative active site serine residue of the Tap.

IV. Methods of Preparing Nucleic Acid Sequences Capable of Coding For the Impaired Proteases Methods of preparing nucleic acid sequences capable of coding for the impaired proteases include: site specific mutagenesis to alter the sequence coding for an essential component of the activity and/or the expression of the protease; and deletion or mutation of the wild type gene by exposure to mutagens. Generally, the deletion of a wild type gene together with the insertion of an impaired gene, would be preferred.

Example 15 describes production of DNA clones with various deletions and mutations resulting in the identification of DNA sequences the removal of which lead to inactivation of the tap gene.

V. Methods of Producing Host Cells with Impaired Protease Activity

Vectors were prepared according to Section III.

Recombinant vectors and isolated segments may therefore variously include the basic protease active site encoding region in an inactive form, coding regions bearing selected alterations or modifications in the basic coding regions, or larger proteins which include the basic coding region. An example is shown in FIG. 8B. In any event, it should be appreciated that due to codon redundancy, this aspect of the invention is not limited to alteration of the particular DNA sequences shown in FIGS. 8B or 8C.

Recombinant vectors such as the foregoing are useful both as a means for preparing qantities of the protease-encoding DNA itself, or as a means of producing defective proteases for use in transforming recombinant host cells for use in fermentation processes to produce various peptides and proteins.

Example 16 describes the use of the deletion clones of the tap gene for integrational mutation into the S. dividans 66 chromosome resulting in inactivation of the wild type tap gene. Loss of the wild type tap gene occurred by homologous recombination with the integrated mutant DNA sequence using the natural ability of the S. lividans host cell to resolve such regions of chromosomal DNA containing directly repeated nucleotide sequences. Resolution occurred apparently at random to produce strains carrying either the wild type parental tap gene or the exchanged mutant tap gene. Mutant strains were identified by their inability to hydrolyse the chromogenic substrate GPL-bNA.

Example 14 describes the use of chemical mutagenic treatment of spores of the S. lividans 66 strain to produce mutant strains in which the Tap encoding DNA is defective, resulting in reduced or abolished expression of Tap.

EXAMPLES

Example 1

Purification of Wild-Type Tripeptidyl Aminopeptidase

S. lividans 66 was grown in 11 liters of minimal media (minimal media=12 g Difco Soytone, 10.6 g $K_2HPO_4$, 5.3 g $K_2PO_4$, 2.5 g $(NH_4)_2SO_4$, and 1.0 g $MgSO_4$–$7H_2O$ per liter) for 24 hrs at 32° C. with stirring at 300 rpm in a Chemap fermenter. Cells were removed from the media by ultrafiltration with a 0.45 μm filter (Pellicon System, Millipore). Proteins in the filtrate were concentrated by ultrafiltration employing a membrane with a 10 kDa cutoff (Millipore). The protease activity was followed by assaying with APA-pNA and GMCSF as described in Example 2. The protease was precipitated at 4° C. by lowering the pH to 4.0 with 0.1M HCl. The precipitate was collected by centrifugation (Model J2-21, Beckman) at 10,000 g at 4°–10° C. and was redissolved in 50 ml 10 mM Tris-HCl, pH 8.0. After dialysis against 4 liters of the Tris buffer at 4° C., the protease was loaded at ambient temperature onto a 1.6×10 cm anion exchange column (Q-Sepharose Fast Flow, Pharmacia) equilibrated with the Tris buffer. After washing with equilibration buffer, the bound protease was eluted with a 200 ml gradient from 0 to 500 mM NaCl at a flow rate of 2 ml/minute. The active fractions were pooled and made 2M in ammonium sulfate. This material was loaded at ambient temperature onto a 1.6×10 cm hydrophobic interaction column (Phenyl-Sepharose Fast Flow, Pharmacia) equilibrated in 10 mM Tris-HCl, pH 8.0, 2M ammonium sulfate. After washing with equilibration buffer, the column was eluted with a 200 ml gradient from to 2 to 0M ammonium sulfate at a flow rate of 2 ml/minute. The active fractions were assayed for purity by SDS-PAGE.

Example 2

Assays of Tap Activity

Aliquots of Tap column fractions were diluted 100-fold with 20 mM Tris-HCl, pH 8.0.

GM-CSF as Substrate

To 10 ul of rhGM-CSF (10 ug, Cangene) and 20 ul 20 mM Tris-HCl, pH 8.0, 20 ul of Tap were added. The assays were incubated at 37° C. for 2 hrs. 20 ul of 125 mM Tris-HCl, pH 6.8, 0.1% bromophenol blue in 50% aqueous glycerol were added. Products were separated by native gel electrophoresis at constant current on a 17% polyacrylamide gel by a modification of the method of Davies (Davies, 1964) in which the pH of all buffers was modified with $HSO_4$. Products were visualized by staining with Coomassie Blue G-250 (see FIG. 1A).

IL-3 as Substrate

To 50 ul 20 mM Tris-HCl, pH 8.0, 40 ul rhIL-3 (2.5 ug/ul, Cangene) was added followed by 10 ul Tap. The assays were incubated at 37° C. 25 ul aliquots were withdrawn at the desired time points and frozen on crushed dry ice. The products were separated by isoelectric focusing from pH 3–10 using Pharmalyte 3–10 (Pharmacia) ampholytes (FIG. 4). Products were visualized by staining with Coomassie Blue G-250. Intact IL-3 had a pI=7.4. The −3 form demonstrates a pI=7.1.

APA-pNA as Substrate

The assay was conducted in a 96 well microtiter plate. To each well in the assay, 50 ul 100 mM Tris-HCl, pH 8.0, were added followed by 25 ul 3.2 mM APA-pNA. 25 ul of Tap were added to the wells and the absorbance was read at 405 nm. The assays were incubated at 37° C. for 2 hours. The absorbance was read at 405 nm. The activity (release of p-nitroaniline) was calculated from the change in absorbance.

Example 3

Inactivation of Tap with PMSF: Assayed with IL-3

Tap stock (Example 1) was diluted 100-fold with 20 mM Tris-HCl, pH 8.0. A fresh solution of 80 mM PMSF was prepared in isopropanol (iPrOH). A Stock Buffer of 20 mM Tris-HCl, pH 8.0 was prepared. Four preincubations were prepared as follows.

iPrOH=58 ul Stock Buffer+2 ul iPrOH

PMSF=58 ul Stock Buffer+2 ul PMSF/iPrOH

Tap+iPrOH=18 ul Stock Buffer+40 ul Tapgw 2 ul iPrOH

Tap+PMSF=18 ul Stock Buffer+40 ul Tap+2 ul PMSF/iPrOH

These were incubated at 22° C. for 30 minutes. When the preincubation was complete, 40 ul rhIL-3 (2.5 ug/ul, Cangene) were added and incubation was initiated at 37° C. Aliquots of 25 ul were removed at 0, 1, 2, and 4 hours. These aliquots were immediately frozen on dry ice. When the sampling process was complete, the products were analyzed by isoelectric focusing from pH 3–10 (Example 2).

Example 4

Amino Acid Sequencing of Tap

Tap was purified as described in Example I and was desalted by size exclusion chromatography. An Immobilon PVDF membrane (Millipore) was solvated according to the manufacturers instructions. Tap was adsorbed to the membrane by filtration employing a slot blot assembly. Protein bound to the membrane was visualized with Amido Black. The sample was excised and subjected to automated Edman degradation for 15 cycles.

Example 5

Synthesis of APACMK 21.3 g (70 mmol) Boc-Ala-Pro (Bachem Biosciences) dissolved in 175 ml anhydrous dimethylformamide (DMF) were activated by adding 7.8 ml (70.7 mmol) 4-methylmorpholine followed by 9.3 ml (70.7 mmol) isobutylchloroformate at −20° C. with stirring. After 15 minutes, 15.1 g A-OBz in 175 ml anhydrous DMF were added. The solution was stirred for 1 hour at −20° C. and then for 17 hours at ambient temperature. The DMF was remove by vacuum rotaryevaporation. The residue was taken up in 175 ml ethyl acetate and extracted each with 5% citric acid, saturated sodiumbicarbonate, water, and brine. The organic layer was dried over anhydrous sodium sulfate for 1 hour. The sodium sulfate was remove by filtration.

2.5 g 5% pd on activated carbon were added and the suspension was agitated under a hydrogen atmosphere for 2 hours. At that time, the starting material had been completely converted to product. The hydrogenation catalyst was removed by filtration through Celite. The solvent was removed by vacuum rotary evaporation.

The resulting 23.7 g (66.3 mmol) of Boc-APA were dissolved in 140 ml anhydrous ethyl acetate and reacted with 7.8 ml (70 mmol) of 4-methylmorpholine followed by 9.2 ml (70 mmol) of isobutylchloroformate at −20° C. with stirring. After 15 minutes, a solution of diazomethane in anhydrous ether prepared from 100 mmol N-methyl-N-nitroso-p-toluenesulfonamide (Aldrich) was added. After 1 hour at ambient temperature, the solution was extracted twice with 140 ml portions of water. The organic layer was dried over 2 g anhydrous sodium sulfate powder for 1 hour. The solution was removed by decantation. Deblocking of the N-terminal and generation of the chloromethylketone group were achieved simultaneously by adding 100 ml of HCl(g) saturated ethyl acetate. The resulting solution was allowed to stand at ambient temperature for 30 minutes. The product was removed from the organic solvent by extraction into 400 ml of water. The aqueous pool was frozen and lyophilized to yield the product, APACMK, as its hydrochloride salt.

Example 6

Inactivation of Tap by APACMK: Assayed with APA-pNA

A stock solution of 10 nM Tap in 100 mM Tris-HCl, pH 8.0 was prepared. Serial dilutions of 210 uM, 21 uM, 2.1 uM, 210 nM, 21 nM, and 2.1 nM APACMK (Example 5) were prepared. To the microtiter well, 25 ul of Tap followed by 25 ul of an APACMK dilution or distilled water, for an uninhibited control, were added. The assays were incubated for 20 minutes at 22° C. 50 ul 1.6 mM APA-pNA were added to each well. The absorbance was read at 405 nm then incubated at 37° C. The change in absorbance at 405 nm was read after 15 and 60 minutes of incubation.

Example 7

Inactivation of Tap by APACMK: Assayed with GM-CSF

A stock solution of 10 Nm Tap in 20 mM Tris-HCl, pH 8.0 was prepared. Serial dilutions of 210 uM, 21 uM, 2.1 uM, 210 nM, 21 nM, and 2.1 nM APACMK (Example 5) were prepared. To 20 ul Tap, 20 ul of an APACMK dilution (or water for an uninhibited enzyme control) were added and incubated at 22° C. for 30 minutes. 10 ul of GM-CSF (1 ug/ul, Cangene) were added and incubated at 37° C. for 2 hours. Products were analyzed by native gel electrophoresis as described in Example 2.

Example 8

Inactivation of Tap by APACMK—Determination of Kinetic Constants

A stock solution of 1.1 uM Tap in 50 mM Tris-HCl, pH 8.0 was prepared. APACMK stock solutions of 11 uM, 13.8 uM, 17.3 uM, 21.7 uM, 27.0 uM, 54.0 uM, 108 uM, and 1.08 mM were prepared. The Substrate Solution was 50 mM Tris-HCl, pH 8.0, 0.8 mM APA-pNA. The inactivation was performed by placing 90 ul of Tap (1 nanomole) in a 1.5 ml Eppendorf tube on ice and adding 10 ul of water (uninhibited control) or 10 ul of APACMK. A 10 ul aliquot was removed immediately and was assayed by adding it to a cuvette containing 390 ul Substrate Solution at 22° C. The initial velocity was obtained from the change in absorbance at 405 nm during the first 10 seconds of the assay. Additional aliquots were removed at time points and assayed by the same method. At APACMK concentrations greater than 5.0 uM in the incubation, it was not possible to remove an aliquot from the incubation before 90% inactivation occurred.

Example 9

Application of APACMK in Fermentation 100 ml of media was inoculated in 500 ml baffle-bottom flasks with 100 ul of S. lividans 66 working seed bank material. The cultures were grown in a New Brunswick gyratory incubator at 32° C. and 240 rpm. The cultures were sampled at 25, 27, 29, 31, and 48 hours post-inoculation and analyzed by native gel electrophoresis (see FIG. 7). Following removal of the 25 hour sample, 100 mM APACMK in sterile water were added to yield a final concentration of 10 uM. A control flask without APACMK was retained. The addition of APACMK significantly reduced formation of GM-CSF(–3) but did not inhibit cell growth.

Example 10

Construction and Screening of a S. lividans Genomic Library

A S. lividans 66 (Hopwood et al., 1983) genomic library was made using size fractionated (3–12 kbp) fragments of chromosomal DNA partially digested with Sau 3AI and ligated into the BamHI site of the bifunctional cloning vector, pSS12 (Butler et al., 1992). The ligated DNA was used to transform competent cells of E. coli HB101 and pooled plasmid DNA was isolated from a mixture of approximately 30,000 transformed colonies grown in SOB medium (Maniatis et al., 1982) containing ampicillin (Sigma). This DNA was used for transformation of S. dividans 66 protoplasts yielding 15,000 transformant colonies resistant to thiostrepton (E. R. Squibb). Two days later the colonies were screened by overlaying with substrate mixture (containing 5 ml phosphate buffer (50 mM, pH 7.0), 25 μl GPLbNA (20 mg.ml$^{-1}$ in DMSO), 0.1 ml Fast Garnet GBC [10 mg.ml$^{-1}$ in water]). The plates were incubated for three minutes at room temperature and washed three times with saline solution (Atlan et al., 1989, Alvafez et al., 1985). Positive colonies stained intensely orange against a background for pale orange colonies.

Two colonies reproducibly showed strong colour. Plasmid DNA was isolated from each of these two colonies and the phenotype was retained when the DNA was used to transform protoplasts of S. dividans 66.

The plasmid DNA from each of these clones (P3-5 and P3-13) was investigated by restriction enzyme analysis. The data indicated that P3-5 and P3-13 were identical (presumably siblings) and the common restriction map is shown in FIGS 8A–8C. Southern hybridization analysis of chromosomal DNA, using the plasmid P3-13 as a probe (FIG. 9), suggested that the DNA contained in P3-13 had not been rearranged during cloning.

Example 11

Tap Activity of S. lividans 66 Strains Carrying the P3-5 and P3-13 Clones

The S. lividans 66 strains carrying the P3-5 and P3-13 clone or pSS12 were grown in TSB (containing 1% glucose, 0.1M MOPS and 20 μg ml$^{-1}$ thiostrepton). Aliquots (40 ml) of each culture were removed at 23 and 29 hours, and the supernatant and mycelium fractions were separated by centrifugation. Aliquots of the supernatant fractions were added to reactions (100 μl) containing various tripeptide-bNA substrates (8 nmol) in microtiter wells. After incubation at 37° C. for 4 hours, a solution (50 μl) containing Fast Garnet GBC dye was added and the $A_{540}$ was measured in a microtiter plate reader. The results are shown in Table IV.

TABLE IV

| | Tripeptidyl Aminopeptidase Activity ($A_{540}$ above background) | | | |
|---|---|---|---|---|
| Sample | GPL-bNA | GPM-bNA | APF-bNA | D-FPR-bNA |
| Supernatants | | | | |
| P3-5/23 HRS | Max | Max | Max | 0.02 |
| P3-5/29 HRS | Max | Max | Max | 0.08 |
| SS12/23 HRS | 0.19 | 0.28 | 0.63 | 0.02 |
| SS12/29 HRS | 1.38 | 2.46 | Max | 0.17 |

("Max" indicates a $A_{540}$ reading of >3.0)

At as early as 23 hours of culture, a 1 μl aliquot of the supernatant from S. lividans carrying the P3-5 clone was showing strong activity against the GPL-, GPM- and APF-bNA substrates. At the same time point, a 25-μl aliquot of the control culture had at least 15 to 20 fold lower activity with the same substrates. However, against the D-FPR- and APF-bNA substrates, the Tap over-producer had little activity over the control. An aliquot (1 μl) of each supernatant (which was harvested after 23 hours of growth) was added to a reaction containing 4 μg of purified intact GM-CSF. Following a 2.5-min. incubation at 37° C., the proteins were analyzed by native PAGE and stained with Coomassie Brilliant Blue. The full-length GM-CSF (lane 1 of FIG. 11) was rapidly converted to the –3 form upon incubation with culture supernatants from cells carrying the tap clones. By contrast, no significant degradation was observed when GM-CSF was incubated with the control culture due to the small volumes of culture supernatant and short time of incubation used compared to those described in Example 2.

Example 12

Analysis of Extracellular Proteins From S. lividams 66 Strains Carrying the p3-5 and p3-13 Clones The S. lividans 66 carrying the P3-5 and P3-13 clones were grown in liquid culture, and supernatant fractions were collected following the teaching of Example 11. As described by Laemmli (1970), samples were prepared from aliquots (200 μl) of the supernatant fractions, and SDS-10% polyacrylamide gels were run at 100 v for 5 to 6 hours. The profile of separated proteins was then visualized by staining with Coomassie Brilliant Blue (FIG. 10). An abundant protein with an apparent molecular weight of 55,000 daltons was present among the extracellular proteins from S. lividans 66 carrying either P3-5 (lanes 2 to 7) or P3-13 (lanes 8 to 13). From 23 to 29 h of culture, the level of Tap increased to approximately 0.1 mg/ml, relative to the BSA standards (lanes 14 to 19). Lanes 1 and 20 show molecular weight markers.

Example 13

Amino Terminal Amino Acid Sequence of the Tap Protein Purified From an *S. lividans* 66 Strain Carrying the P3-13 Clone The *S. lividans* 66 strain carrying the P3-13 clone was grown in liquid culture and supernatant fractions were collected, following Example 11. The extracellular proteins were separated by SDS-PAGE, following the teaching of Example 12, and transferred onto Immobilon PVDF (Millipore) membranes as directed by the supplier. After briefly staining the filters with Coomassie Brilliant Blue, the bands containing the major protein (apparent molecular weight 55,000 daltons) were excised from the filter, and subjected to automated Edman degradation analysis. The N-terminal amino acid sequence (SEQ ID NO:10) determined was: Asp-Gly-His-Gly-His-Arg-Ser-Gln (or Ser)-Asp-Ala.

Example 14

Production of Mutant Strains of *S. lividans* Defective in Protease Activities Using Chemical Mutagenesis

*S. lividams* 66 spores were treated with N-methyl-N-nitro-N-nitrosoguanidine (MNNG) according to the method of Hopwood et al., (1985). Briefly, a suspension containing $2.5 \times 10^{12}$ spores in 3 mls of Tris/maleic acid buffer was incubated at 30° C. in a preweighed vial containing 10 mgs of MNNG (which had been solubilized in 0.5 ml DMSO immediately prior to the addition of the spore suspension). 1 ml aliquots were removed from the mixture at 30 minute intervals and washed twice by centrifugation to remove the MNNG. Serial dilutions of the treated spores were plated on agar medium to determine the effectiveness of the mutagenic treatment in terms of the proportion of viable surviving colony forming units remaining compared to untreated spores. Survival rates of $2.8 \times 10^{-3}\%$, $1.2 \times 10^{-4}\%$ and $9 \times 10^{-6}\%$ were observed after 30, 60 and 90 minutes, respectively.

Two hundred surviving colonies from each of the three treatment times were purified and examined for their ability to grow on minimal media. Colonies which were unable to grow were classified as auxotrophic mutants of which 1, 4 and 2 were observed at the 30, 60 and 90 minute treatment times, respectively.

Spores from the 60 minute treatment were, therefore, examined for the presence of strains carrying mutations which inactivated specific proteolytic phenotypes. A direct agar plate screening technique was used in which the colonies were overlayed with substrate mixture (containing 0.1 ml of GPL-bNA (Bachem Inc., 1 mg dissolved in DMSO), 0.1 ml Fast Garnet GBC (Sigma) dye (10 mg.ml$^{-1}$ in water), 6 ml of 50 mM phosphate buffer, pH 7.0 and 0.2 ml DMSO. The plates were incubated for twenty minutes at room temperature and washed three times with saline solution (Atlan et al., 1989, Alvarez et al., 1985). Screening of 2,700 colonies using GPL-bNA revealed two colonies which did not turn red. Testing supernatants from liquid cultures of one of these colonies (12-5 or 12-8), with various chromogenic tripepride substrates (Table V), confirmed that this specific hydrolyric ability had been either eliminated or at least very substantially reduced compared to the original untreated *S. lividans* strain.

TABLE V

| | Tripeptidyl Aminopeptidase Activity ($A_{540}$ above background) | | | |
|---|---|---|---|---|
| Sample | GPL-bNA | GPM-bNA | APF-bNA | D-FPR-bNA |
| Supernatants | | | | |
| 12-5/T2 | 0.01 | 0.01 | 0 | 0 |
| 12-5/T4 | 0.10 | 0.10 | 0.05 | 0.06 |
| 12-8/T2 | 0.02 | 0.02 | 0 | 0 |
| 12-8/T4 | 0.13 | 0.12 | 0.12 | 0.08 |
| 1-5/T2 | 0.01 | 0.01 | 0.01 | 0.02 |
| 1-5/T4 | 2.55 | Max | Max | 0.09 |

("Max" indicates a $A_{540}$ reading of >3.0)

In a similar experiment to that described above, a L-bNA substrate was used, resulting in the isolation of one mutant (lap$^-$) strain (1–5) from 1500 colonies screened. By comparison, the Tap activity of this mutant strain was unchanged from that of wild type *S. lividans* 66.

Aliquots of each culture supernatant were added to reactions containing 2.5 µg GM-CSF and incubated at 32° C. for 2 minutes. The proteins were separated by SDS-PAGE and visualized by Western blotting, using an antiserum raised against the amino terminal 35 amino acids of GM-CSF. At 40 h (T3), the cultures from the tap mutants, #11 and #12 contained less activity for converting GM-CSF to the −3 form than those from the *S. lividans*, MS2 and the lap mutant, #1.

Protoplasts were prepared from the various *S. lividans* 66 mutants, and were transformed using the GM-CSF expression vector pAPO.GMCSF (as described in Canadian patent number 1,295,567 and U.S. Pat. No. 5,200,327). The transformed cells were grown in liquid culture and the supernatant fractions were collected following the teaching of Example 11. Aliquots of each culture supernatant were analyzed by SDS-PAGE. The transformants with the tap mutants, 12-5 and 12-8 generally showed more intact GM-CSF at later time points in the culture than the *S. lividans*, MS2. However, the formation of the −3 form of GM-CSF was not completely eliminated with the tap mutants.

Example 15

Construction of A Deletion Subclone From the tap Clone

Specific deletions were made in the tap clone to localize the gene and enable chromosomal disruption. A 1.2-kbp DNA fragment was removed between BamHI (1100) and BglII (2300) (see FIG. 8B) to construct the deletion clone Δ1. P3-5 DNA was digested by means of EcoRI and BglII, and the vector fragment was isolated; and P3-5 was digested with EcoRI and BamHI and the 1.1-kbp insert fragment was isolated. The vector and insert fragments were ligated, using T4 DNA ligase, and used to transform *E. coli*. The plasmids were screened by restriction analysis and the correct plasmid, Δ1, used to transform protoplasts of *S. lividans* 66. The *S. lividans* 66 carrying the Δ1 deletion clone was screened with a plate assay using GPL-bNA. A transformant was grown in liquid culture, and the level of Tap activity was determined in a liquid assay using tripeptide-βnapthylamide substrates. The *S. lividans* 66 carrying the Δ1 deletion subclone had a similar Tap activity to that of the untransformed host strain.

Deletion clone Δ2 was constructed by subcloning the EcoRI-BglII fragment into the vector pSS12 which had previously been digested with EcoRI and BamHI. Δ3 was made by digestion of P3-5 DNA with BglII, followed by religation, resulting in the loss of the 300 nt BglII fragment around the centre of the tap gene. The high level of Tap activity associated with the P3-5 plasmid was not observed with Δ2 or Δ3, confirming that the deletions resulted in loss of enzyme activity.

Example 16

Deletion Clones Used for Integrational Mutation of tap into the S. lividans 66 Chromosome Subcloning of the DNA insert sequences from the deletion clones was not straightforward due to the presence of multiple BamHI sites. A partial BamHI digestion of P3-5 DNA was followed by a complete EcoRI digestion. The 3.1 kbp tap-encoding fragment was isolated from an agarose gel and subcloned into the E. coli vector pT7T3 which had previously been digested with BamHI and EcoRI. Appropriate transformants were identified and the DNA insert was used to create further subclones in the pINT vector as follows. Δ1int was produced by a three way ligation of the EcoRI-BamHI, BglII-HindIII (in the polylinker of the pT7T3 vector) fragments from the pT7T3 subclone and the EcoRI-HindIII fragment produced by digestion of pINT. Δ2int was the result of a direct subcloning of the EcoRI-BglII fragment from the pT7T3 subclone into piNT digested with EcoRI and BamHI. Δ3int involved the BglII-HindIII fragment from the pT7T3 subclone and BamHI plus HindIII digested pINT. Δ4int was a direct subcloning of the whole inserted fragment in the pT7T3 subclone (EcoRI + HindIII) into the same sites in pINT. Δ5int was made from Δ4int by digestion with BglII and religation. The DNA contained within the various ∴int clones is shown in FIG. 8C.

Plasmid DNA was isolated from the E. coli transformed strains and used to transform protoplasts of S. lividans MS5 (a strain derived from S. lividans 66 by deletion of DNA fragments at the slpA and slpC (Butler el al., 1992) loci; in addition the pepP gene (Butler et al., 1993) and a second PepP-encoding gene (Butler et al., J. Ind. Microbiol., in the press) were also subjected to specific chromosomal DNA deletion events, each of which reduced the PepP activity of the S. lividans strains). Integrative transformants resistant to thiostrepton were purified and allowed to grow in the absence of thiostrepton to allow recombinational resolution to occur. Strains which had undergone excision events were easily identified by screening for the loss of the ability to hydrolyse GPL-bNA. The results obtained were somewhat unexpected. Δ1int did not produce any integrarive thiostrepton-resistant transformants in three independent experiments. Δ2int did lead to integrative transformants, indicating that there was no practical impediment to recombination events at this locus on the S. lividans chromosome. Δ3int failed to produce integrarive transformants, possibly due to the relatively small length of DNA (900nt) available for homologous recombination to occur. Δ4int yielded tranformants as did Δ5int. Subsequent experiments using Δ1int were successful using S. lividams 66 protoplasts (to make a strain designated MS9 which was defective only at the tap locus) suggesting that the earlier failure in the MS5 experiment was due to the lower transformation capability of that particular batch of MS5 protoplasts.

Integrarive transformants from Δ5int were grown in the absence of the thiostrepton selection on agar medium. After sporulation had occurred the spores were harvested and replated onto fresh agar plates. Colonies were screened using the βnaphthylamide substrate assay for tap activity. The frequency of excision events which led to loss of the activity was very low (approximately 1 in 1000). Three colonies were obtained with reduced Tap activity. Chromosomal DNA was isolated and Southern hybridisation analysis (FIG. 9) confirmed that one colony (#2) had lost the 300 nt BglII fragment (lanes 3 and 7 compared to the S. lividans 66 control lanes 2 and 6). Similar experiments with a 3.3 kbp DNA probe revealed a complex hybridising band pattern in colony 1 chromosomal DNA whereas colony 2 DNA showed only the expected bands with a reduction in size of one band consistent with the desired specific chromosomal deletion. Colony 2 was designated Streptomyces lividans MS7. Another strain was constructed using Δ5int and S. lividans 66 protoplasts. This strain was designated MS8 and shown to have properties indistinguishable from those of MS9.

Example 17

The S. lividans MS7 Strain shows a substantial reduction in its ability to hydrolyse Tripepride bNA substrates and GM-CSF in vitro The S. dividans MS7 strain was grown in liquid culture (TSB medium) and supernatants collected by centrifugation to remove the mycelialmaterial. Aliquots (50 μl) of the supernatants were added to each of the tripepride substrates (8 nmol) in a final volume of 100 μl. After incubation at 37° C. for 45 minutes, 50 μl of a solution of Fast Garnet GBC dye was added and the A540 measured using a microtiter plate reader.

Figure 14:
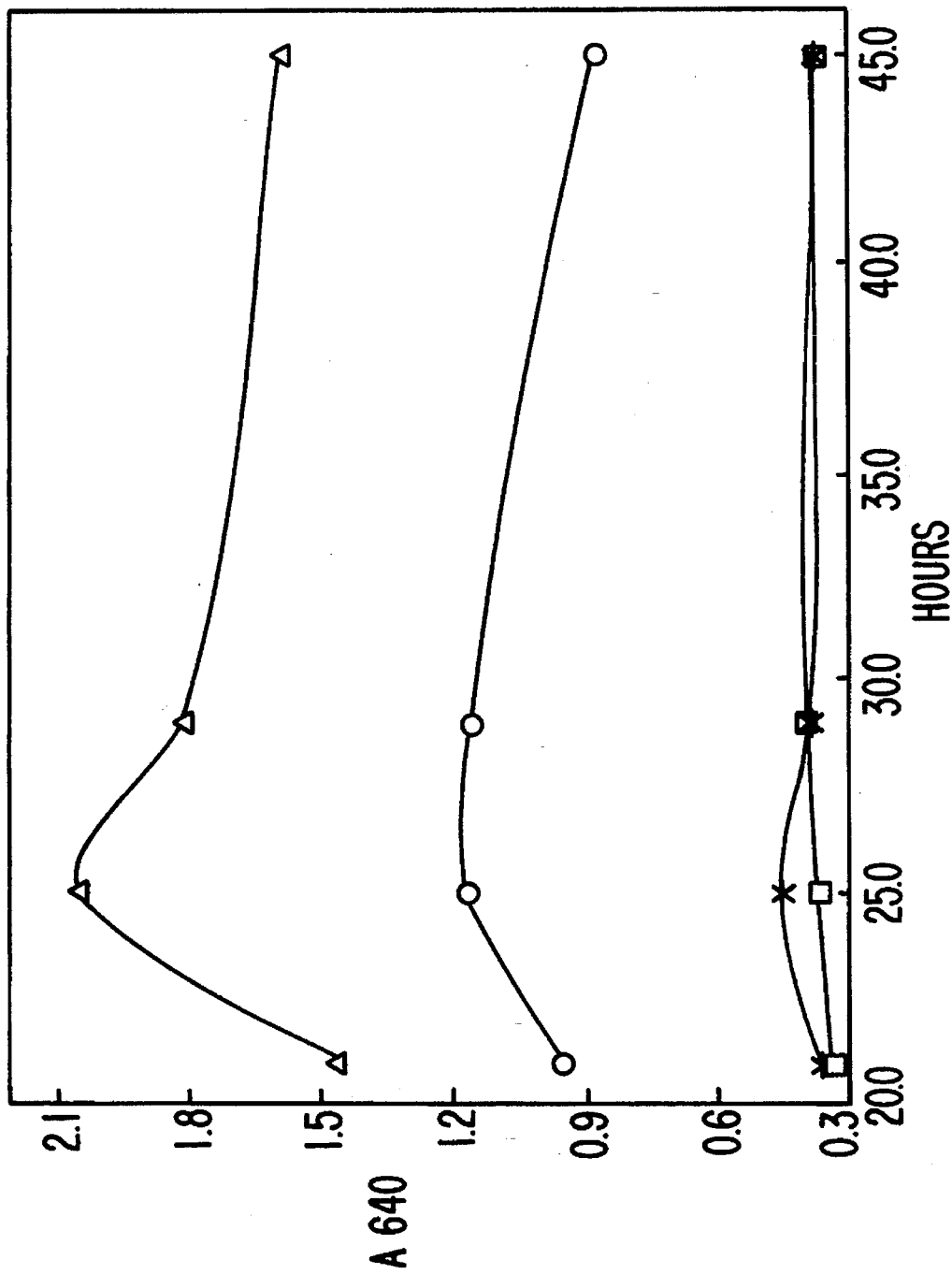
FIG. 14. Activity of fermentation culture supernatants from S. lividans MS5 (tap+) and S. lividans MS7 (tap–) strains against chromogenic tripepride substrates.

FIG. 14 shows the activity of S. lividans MS5 (tap+) and MS7 (tap) strains against chromogenic tripepride substrates. Cell-free broth from the strains was isolated at various times of fermentation (without thiostrepton) and incubated with either APA-bNA or GPL-bNA.

The symbols represent the following combinations:
MS7+APAbNA (-□-)
MS7+GPLbNA (-*-)
MS5+APAbNA (-Δ-)
MS5+APLbNA (-o-)

The results are summarized in FIG. 14 and indicate that under these assay conditions, the supernatants derived from the MS7 culture were (within experimental error) devoid of any significant hydrolyric ability against these substrates, whereas the supernatant derived from S. lividans MS5 showed the ability to rapidly degrade both substrates.

Figure 15:
FIG. 15. Reduction in the rate of degradation of intact GM-CSF by fermentation supernatants of cultures of the tap mutant.

FIG. 15 shows the degradation of full-length GM-CSF by cell-free broth from S. lividans MS5 and MS7. Cell-free broth was isolated from cultures grown without thiostrepton for 25 hours. Degradation was significantly slower for MS7 than MS5.

when the same supernatant samples were analyzed for the ability to degrade GM-CSF in vitro (according to the teaching of Example 15), it was clear that the rate of degradation of GM-CSF for the MS7 samples (FIG. 15, lanes 4–6) was much slower than for the MS5 samples (FIG. 15, lanes 1–3).

Example 18

Production of undegraded GM-CSF by the S. dividans MS7 Strain

The GM-CSF expression plasmid vector pAPO.GMCSF was used to transform Protoplasts of the S. lividans MS7 strain. Following the teaching of Example 11, liquid cultures were prepared from the transformed strain as well as transformants from the S. lividans MS5 strain.

Figure 16:
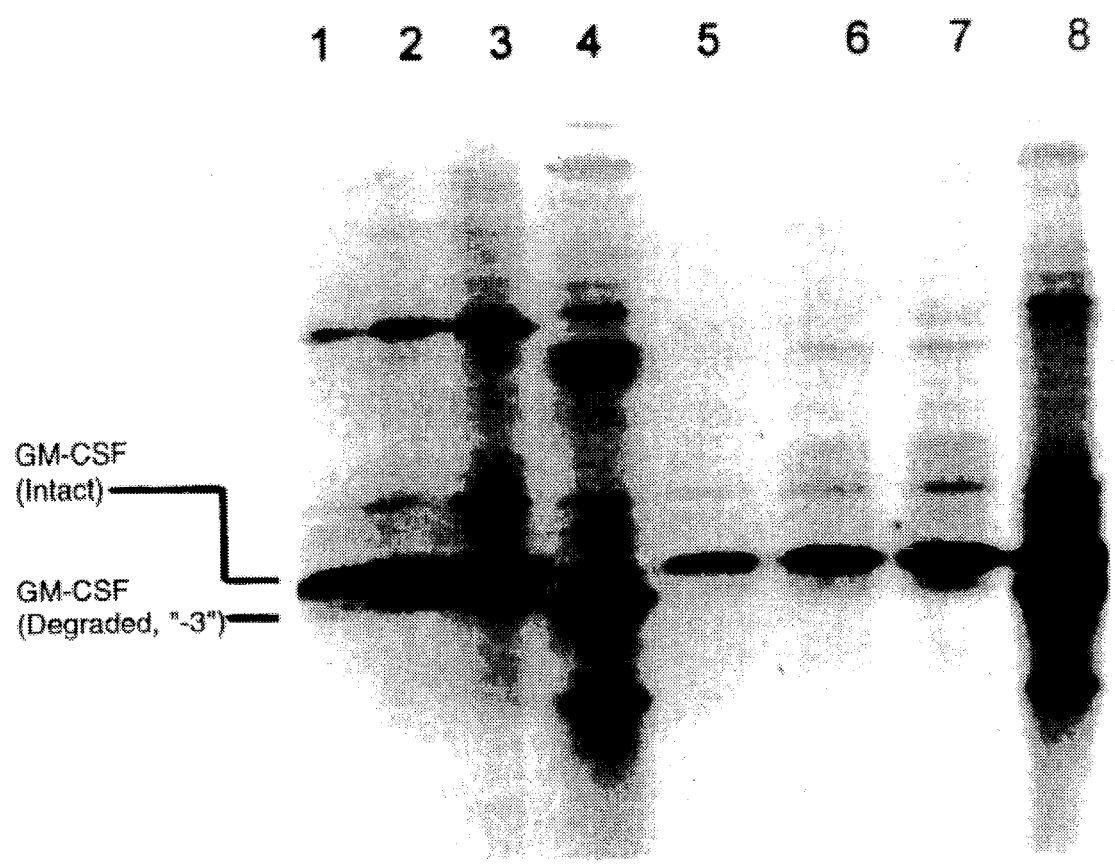
FIG. 16. PAGE resolution and Coomassie Brilliant Blue staining of fermentation supernatants from cultures of S. lividans 66 and S. lividans MS7 mutant protoplasts transformed with the GM-CSF expression vector pAPO.GMCSF.

FIG. 16 illustrates production of GM-CSF by S. lividans 66 and the deletion mutant strain MS7. Cell-free broth from the strains was harvested after fermentation for the times shown and analyzed by native PAGE.

Native PAGE analysis of the culture supernatants revealed that while degradation of the secreted GM-CSF occurred in both strains, it was only evident in the MS7 supernatant material (FIG. 16, lanes 5–8) at later times of growth compared to the MS5 samples (FIG. 16, lanes 1–4). This property of the new S. lividans MS7 strain allowed it to be used to produce a higher yield of undegraded GM-CSF than was possible using the wild-type S. lividans 66 strain.

Example 19

Tap Activity is Present in a Wide Variety of Streptomyces Species

Genomic DNA was isolated from the following Streptomyces strains. S. alboniger 504 (P. Redshaw, Austin College, Tex., USA), (S. coelicolor M130 (John Innes Institute), S. fradiae ATCC 14544, S. griseus IMRU 3499, S. griseus ATCC 10137, S. parvulus 2283 (John Innes Institute) S. rimosus ATCC 10970. 10 µg of each DNA were digested in 100 µl of appropriate buffer for the restriction enzymes BamHI and PstI respectively. 30 units of each enzyme were added together with 1 µl of RNAse A (10 mg/ml, Sigma). The reactions were incubated at 37° C. for 3 hours. A further 15 units of enzyme were added and the samples incubated overnight at 37° C. Digestions were terminated by the addition of 11 µl of stop buffer (Orange G, 0.08%; glycerol, 50%; EDTA, 67 mM; pH5). Approximately 3 µg of each digested DNA sample were loaded onto a 1% agarose horizontal gel and electrophoresed at 100 V for 4 hours. A molecular weight marker was included (Leda DNA digested with HindIII, Bethesda Research Laboratories to calibrate the gel. After electrophoresis the gel was soaked in 0.25M HCl, followed by 0.5M NaOH, 1.5M NaCl and rinsed in water. The DNA was transferred to a Nylon membrane (Boehringer Mannheim) using a Vacublot (Pharmacia) apparatus with 20×SSC buffer for 1 hour at 50 mbars pressure. After transfer the membrane was washed in 2×SSC and baked for 1.5 hours at 80° C.

The DNA insert fragment from the EcoRI site to the right-most BamHI site was isolated by partial BamHI and complete EcoRI digestions of the P3-13 DNA. The fragment was subcloned into the E. coli plasmid vector pT7T3 (Pharmacia). From this clone it was possible to isolate larger quantities of the same DNA fragment by digestion with EcoRI and HindIII. 0.5 µg of this 3.3 kbp-fragment were labelled according to the manufacturers's recommendations (Boehringer Mannheim) to produce a digoxigenin—labelled probe. 25 ng of probe were used per ml of hybridization solution. Lambda DNA was labelled in the same way to allow visualisation of the molecular weight marker fragments. Hybridization was carried out at 68° C. overnight using 2.5 ml of hybridization solution per 100 cm² of nylon membrane. The hybridization solution contained; 5×SSC; blocking reagent, 1% (w/v); N-lauroylsarcosine, 0.1% (w/v); sodium dodecyl sulphate, 0.02% (w/v). Filters were prehybridized for 1 hour at 68° C. Probes were boiled for 10 minutes, quick chilled on an ice/NaCl bath, diluted with 100 µl hybridization solution and added to the prehybridized membrane in a stoppered glass bottle. Hybridization and prehybrization were carried out using a Hybaid mini-hybridization oven. Membranes were washed twice at 68° C. for 30 minutes in 5×SSC, 0.1% SDS (50 ml/100 cm² membrane). The membranes were then transferred to plastic containers and processed according to the manufacturer's instructions.

Finally, membranes were transferred to plastic bags, sealed and incubated at 37° C. for 30 minutes. Membranes were then exposed to X-ray film for 10 minutes. After development of the X-ray film the autoradiogram shown in FIG. 17 was obtained.

Figure 17:
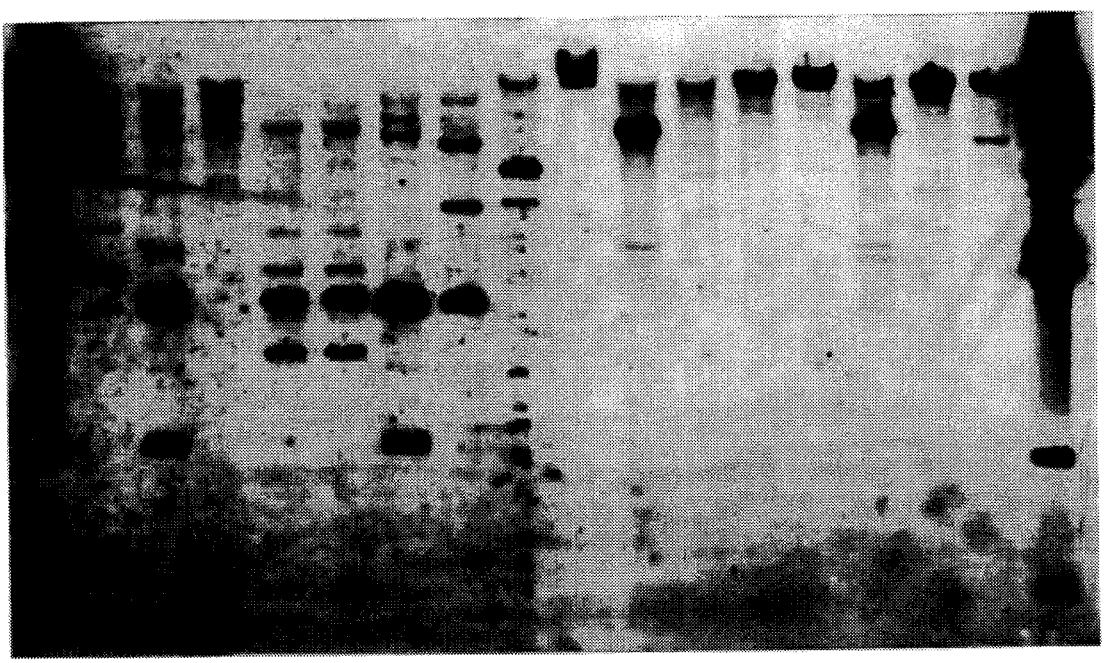
FIG. 17. Homologs of tap are present in many Streptomyces strains.

The autoradiogram showed hybridizing bands in all lanes except those containing S. fradiae DNA. Lanes 1 and 18 contained Lambda/HindIII molecular weight markers. In FIG. 17, lanes 2 and 10, S. alboniger; lanes 3 and 11, S. coelicolor; lanes 4 and 12, S. fradiae; lanes 5 and 13, S. griseus IMRU 3499; lanes 6 and 14, S. griseus ATCC 10137; lanes 7 and 15, S. lividans 66; lanes 8 and 16, S. parvulus; lanes 9 and 17, S. rimosus.

Identical hybridizing bands were observed with S. lividans and S. coelicolor with a common band in both S. griseus strains as well as the S. parvulus DNA. S. rimosus and S. alboniger produced hybridizing bands at different molecular weights suggesting restriction fragment length differences in these species. No strong band was observed for the S. fradiae DNA. Taken overall the results suggested that the Tap-encoding DNA sequence occurs widely throughout the Streptomyces strains examined.

In a similar experiment using S. ambofaciens ATCC 23877 DNA, strongly hybridizing bands were observed after digestion with BamHI, PstI, SacI, and SalI. This indicated the likely presence of a tap gene in S. ambofaciens which would be expected to be detrimental to product yield when expression of secreted proteins is desired in this strain.

The following examples relate to proteases, other than Tap, derived from Streptomyces, their DNA sequences and amino acid sequences. These proteases degrade certain substrates under certain conditions. Example 20 describes one such protease, which displayed a significant amino acid sequence homology with the Bacillus subtills protease BPN' (using the BLAST program [Altschul et al]to screen the protein sequence databases) and was therefore designated Ssp (Subtilisin-like-protein). An improved strain of Streptomyces in which this protease is impaired, was created. Southern blot hybridization indicated that Ssp is present in many Streptomyces species. Three other proteases, the DNA sequences and deduced amino acid sequences for two of them, are described in Examples 21, 23 and the n-terminal amino acid sequence of the third protease is indicated in Example 22.

Example 20

Following the teaching of Example 10, the S. lividans 66 genomic library was used to transform protoplasts of the MS7 mutant strain. Transformant colonies were screened with the substrate APA-bNA. Among the thirteen thousand colonies screened, two clones were isolated by virtue of the plasmid-encoded phenotype (colonies appeared red against a background of pale colonies). Plasmid DNA was isolated from these colonies and used to transform E. coli competent cells from which larger quantities of plasmid DNA were isolated.

Figure 18:
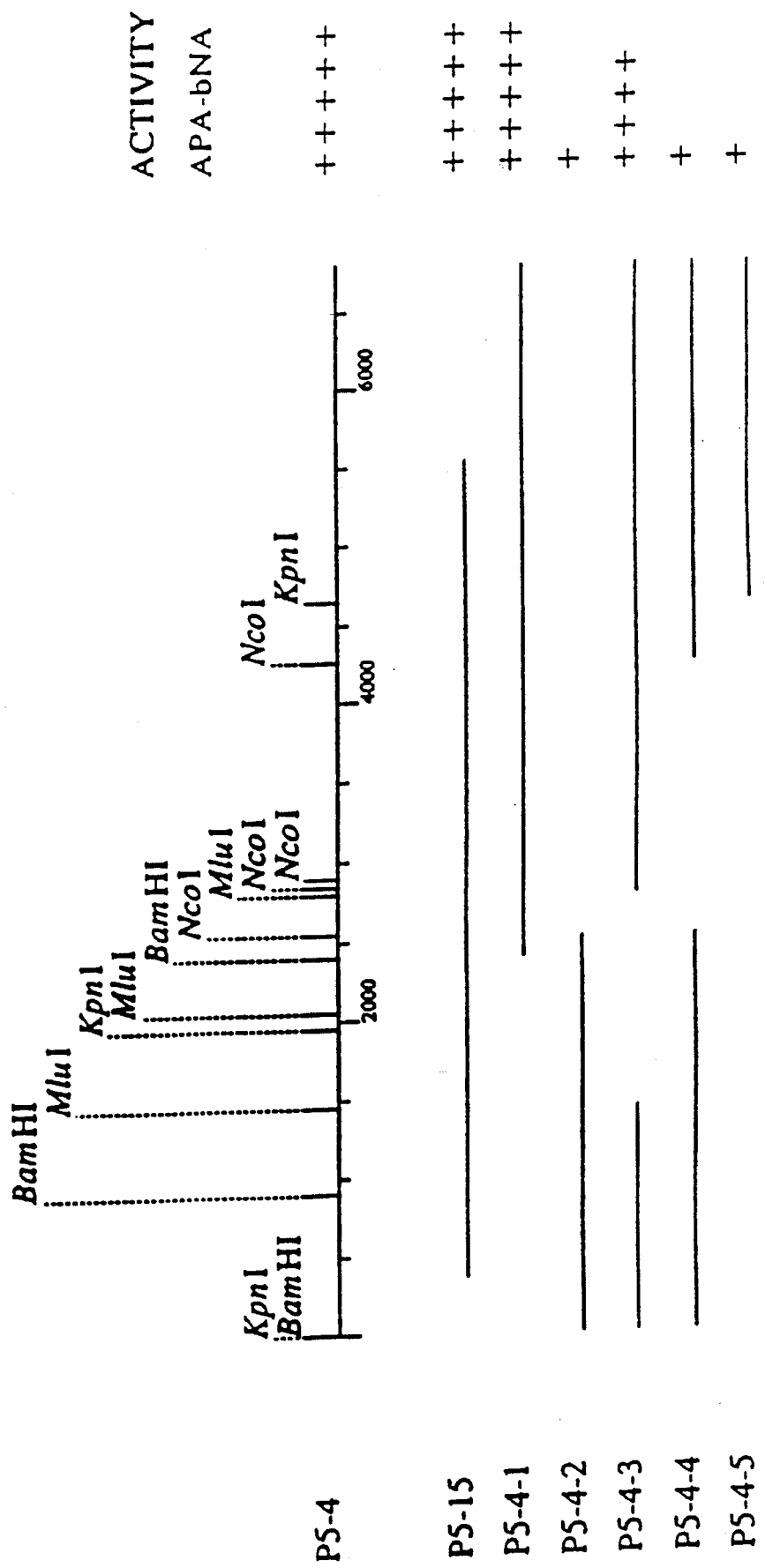
FIG. 18. Common restriction map for P5-4 and P5-15 and their deletion clones.

Restriction enzyme site mapping established that two clones (designated P5-4 and P5-15) were shown to represent overlapping fragments of S. lividans chromosomal DNA containing the Sspencoding gene. FIG. 18 shows the restriction enzyme sites present in the P5-4 and P5-15 DNA. K=KpnI, B=BamHI, M=MluI. The hydrolyric capabilities of strains containing the cloned DNA (or deletions thereof) was measured visually using the agar plate assay method. Southern hybridization against chromosomal DNA showed the expected pattern of hybridizing bands indicating that no major DNA rearrangements had occurred during the isolation of these clones.

Following the teaching of Example 15 the region of DNA encoding the proteolytic activity was defined within the deletion clones P5-4-1 and P5-4-3 (FIG. 18). Specifically, the larger of the two NcoI fragments deleted in P5-4-2, P5-4-4 and P5-4-5 appears to be correlated with the proteolytic activity.

Figure 19:
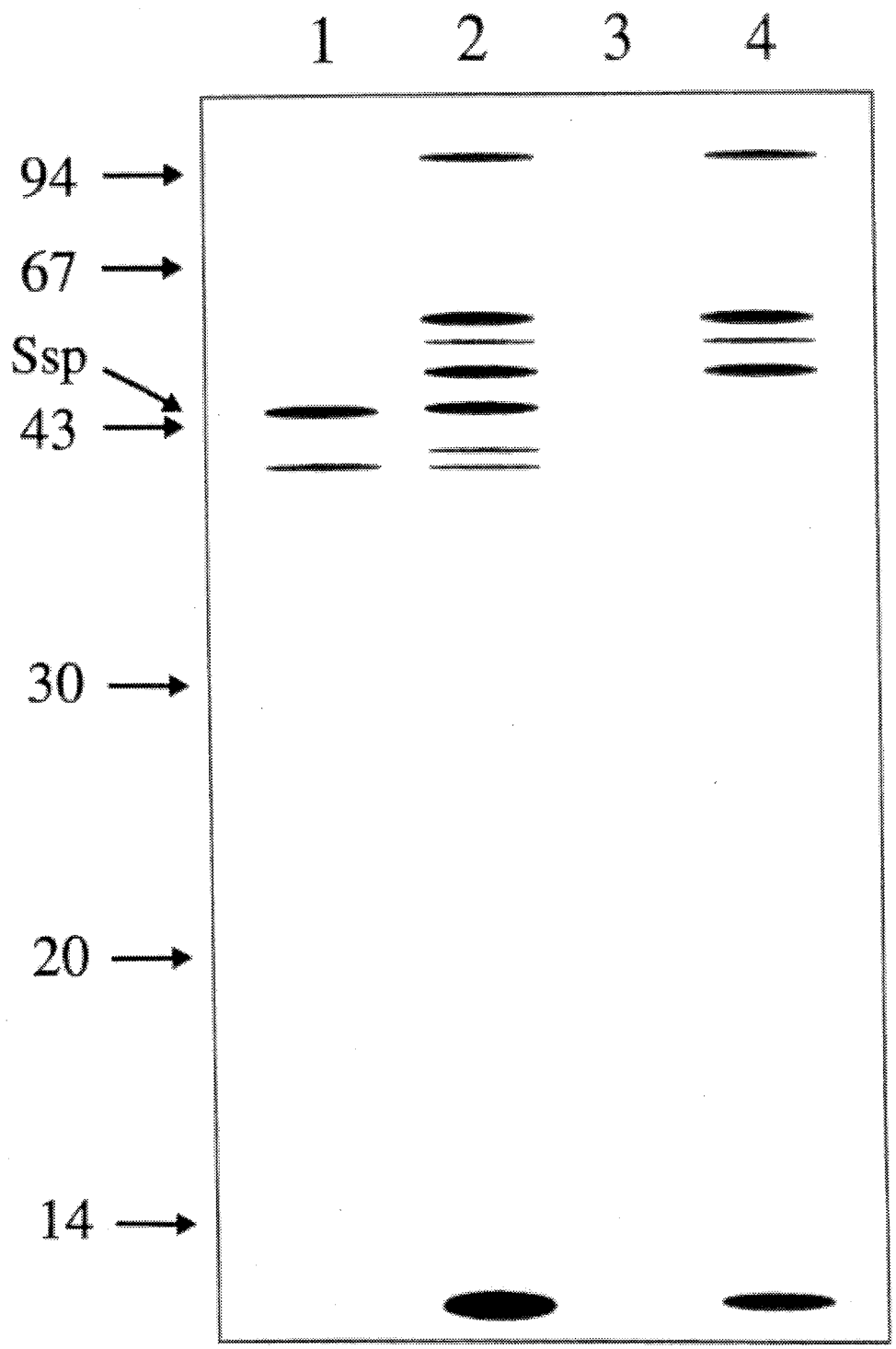
FIG. 19. SDS-PAGE resolution and Silver staining of proteins secreted in a fermentation culture containing the P5-4 plasmid DNA.

FIG. 19 shows SDS-PAGE analysis of protein secreted by strains carrying the P5-4 DNA (Lanes 1 and 2) or the P5-4-4 deletion clone (Lanes 3 and 4). Lanes 1 and 3 contained 30 µl of cell-free broth. Lanes 2 and 4 contained approximately 2 µg protein derived from the cell-free broth samples by ammonium sulphate precipitation. The positions of molecular weight marker are shown by arrows. A major protein specie was observed at a position consistent with a molecular weight of approximately 45,000. Preparative SDS-PAGE followed by electrotransfer to PVDF membrane (as described in Example 13) allowed direct automated Edman degradation to be carried out to yield the amino acid sequence (residues 1–30 of SEQ ID NO:4 $NH_2$-Asp-Thr-Gly-Ala-Pro$^5$-Gln-Val-Leu-Gly-Gly-$^{10}$-Glu-Asp-Leu-Ala-Ala-$^{15}$-Ala-Lys-Ala-Ala-Ser$^{20}$-Ala-Lys-Ala-Glu-Gly$^{25}$-Gln-Asp-pro-Leu-Glu$^{30}$.

DNA sequence analysis (shown in FIGS 21D–26C, SEQ ID NOS 3 and 4 ) of the P5-4 DNA revealed a potential protein coding region located within the region of DNA defined by the two NcoI fragments in FIG. 18. This was consistent with the respective activities of the plasmid deletion clones P5-4-1, P5-4-2, P5-4-3, P5-4-4 and P5-4-5. Inspection of the predicted protein sequence reveals the exactly matching, experimentally determined amino terminal amino acid sequence noted above. Furthermore, the predicted amino acid sequence also shows a putative signal sequence at the amino terminus, followed by a putative pro region defined by the amino terminal end of the experimentally determined mature amino acid sequence.

Figure 30:
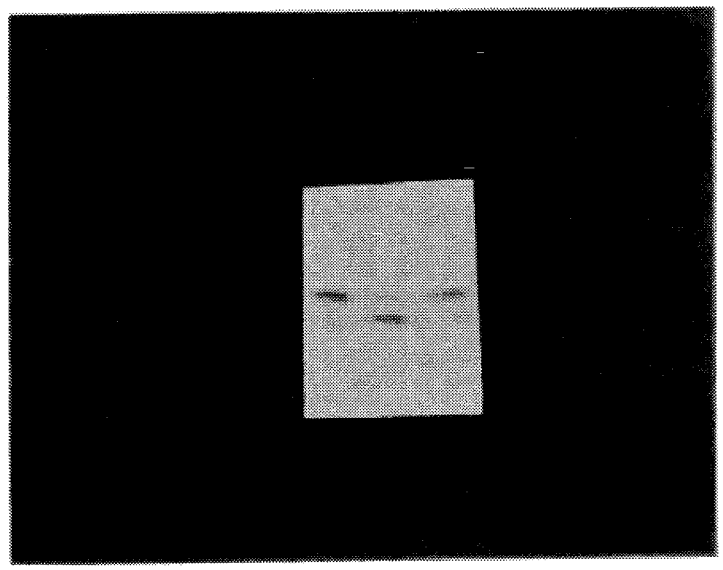
FIG. 30. Conversion of an intact substrate GM-CSF to its "–3 form" upon incubation with fermentation culture supernatants from cells carrying P5-4, P5-10 and P5-15.

FIG. 21 shows a comparison of the amino acid sequence of the proteins predicted from the P5-4 DNA sequence (SEQ ID NO:4) with that of the Bacillus protein subtilisin BPN (SEQ ID NO:12). 1 designates the S. lividans sequence while 2 designates the Bacillus sequence. GM-CSF degradation assays according to methods used in Example 2 using cell-free broth from S. lividans MS7 strain carrying the P5-4 plasmid DNA culture in TSB medium demonstrated that the overproduced Ssp also degraded GM-CSF. In FIG. 30, lane 1 shows such GM-CSF degradation by a P5-4-containing MS7 strain; lane 3 shows a similar result with a P5-15-containing MS7 strain. In contrast, lane 2 shows broth from a P5-10 culture which shows only slight degradation to the "–3 form". The same results were obtained with samples from cultures carrying only the PSS12 plasmid.

Deletion of the Ssp-encoding DNA from the S. lividans chromosome was accomplished following the teaching of Example 16. Specifically, the DNA from plasmid deletion clone P5-4-4 (FIG. 18) was subcloned into pT7T3 using the EcoRI site immediately adjacent to the leftward side of the DNA insert (shown in FIG. 18). Since there was no convenient restriction enzyme site to the rightward side of the DNA insert this was excised using the XhoI site (in the replication origin of the plasmid vector, pSS12) which was subsequently ligated to the SalI-digested pT7T3. Hence, overall the EcoRI-XhoI fragment was inserted in EcoRI and SalI digested T7T3 DNA. The fragment was subsequently excised by digestion with EcoRI and HindIII and inserted into the integration vector, pINT using the same restriction enzyme sites. The pT7T3 intermediate step was required because the SalI site in the multiple cloning site of pINT was not unique and, therefore, not convenient for subcloning purposes.

This integration clone was used to create strains containing the specific deletion at the ssp locus in two S. lividans host strains. Firstly, the MS7 host strain was used to create a new strain designated MS11 (pepP1⁻, pepP2⁻, slpA⁻, slpC⁻, tap⁻, ssp⁻). Secondly, another tap-deleted strain (MS9) was used to create MS12 (tap⁻, ssp⁻). The deletion strains MS7, 9, 11 and 12 were cultured in TSB/PPG liquid medium for 22 hours and examined for the ability of cell-free broth to hydrolyse APA-pNA.

Figure 22:
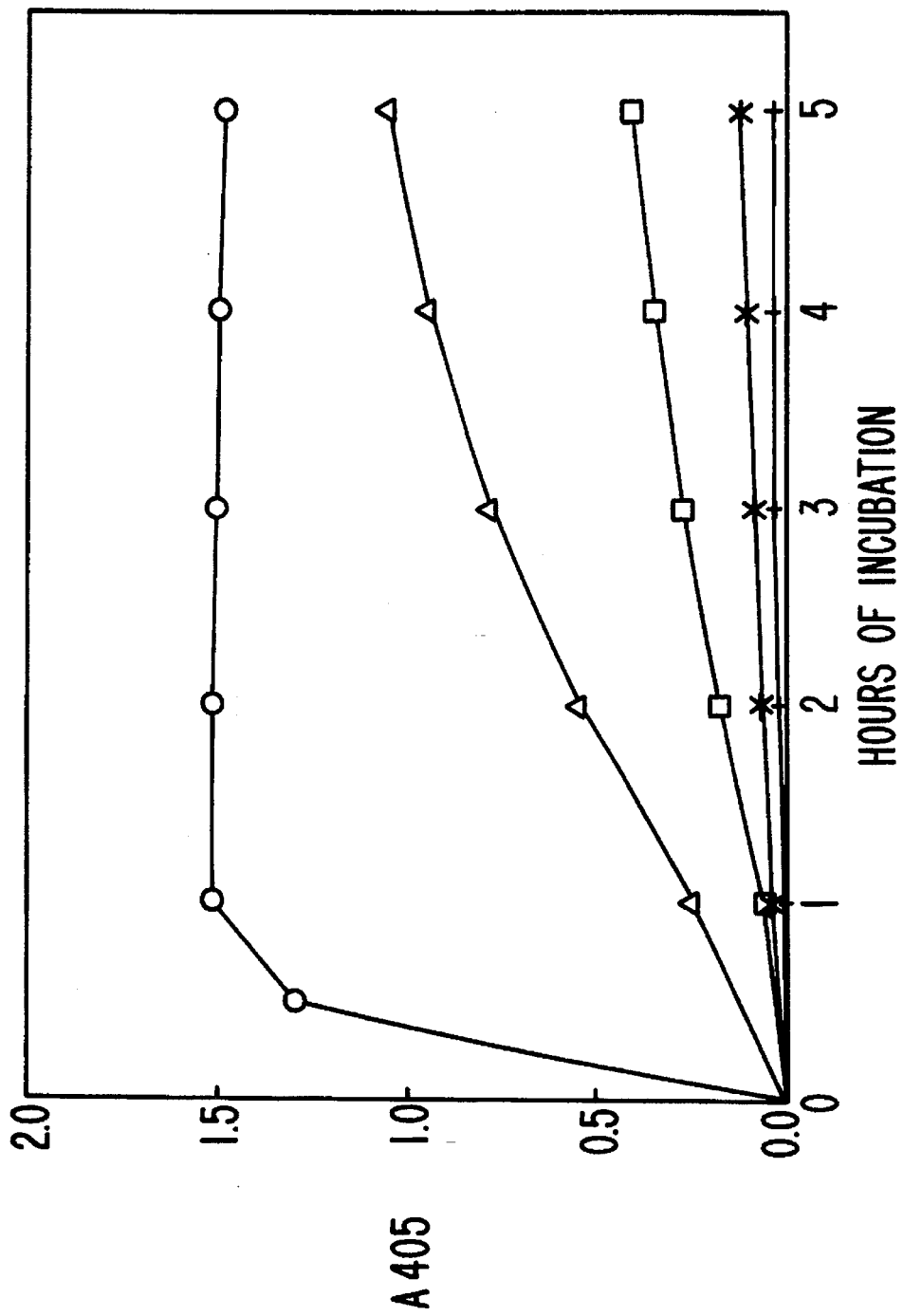
FIG. 22. Proteolytic Activity of S. lividans deletion strains using the substrate APA-pNA.

FIG. 22 shows the activity of cell-free broth samples derived from S. lividans 66 (-0-), MS7 (-Δ-), MS9 (-□-), MS11 (-*-) and MS12 (-+-) strains against the APA-bNA substrate according to the teaching of Example 2.

The results (FIG. 22) showed a reduction in hydrolyric capability with the MS12 strain showing the lowest activity. All the strains displayed a significantly reduced hydrolyric capability compared to S. lividans 66 but the MS9 strain showed a lower level than the MS7 strain. (This was shown in a separate experiment not to be due to the different integration clones used, since MS8 used the same integration clone as MS7 but was derived from S. lividans 66 protoplasts and showed indistinguishable properties to MS9).

Figure 23:
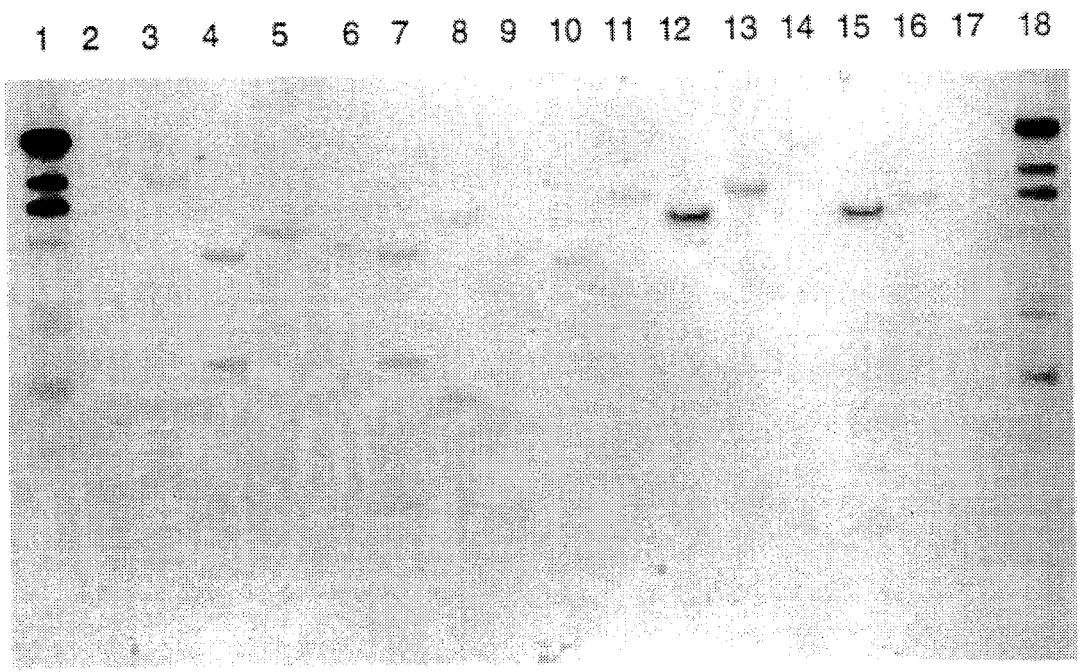
FIG. 23. Homologs of the P5-4 DNA are present in the chromosomal DNA of many Streptomyces strains.

Southern hybridization experiments detected DNA sequences homologous to the ssp DNA in many Streptomyces species. FIG. 23 shows a Southern blot hybrodization experiment using the 2.25 kb BamHI-KpnI DNA fragment which had been subcloned into pT7T3.18 µ. Lanes 1 and 18 are lambda/HindIII molecular weight markers. Lanes 2 to 9 represent chromosomal DNA digested with NcoI while lanes 10 to 17 show DNA digested with SphI. Lanes 2 and 10, S. alboniger; Lanes 3 and 11, S. ambofaciens; Lanes 4 and 12, S. coelicolor; Lanes and 13, S. fradiae; Lanes 6 and 14, S. griseus; Lanes 7 and 15, S. lividans 66; Lanes 8 and 16, S. parvulus; Lanes 9 and 17, S. rimosus.

It should be noted that the same library of clones was screened as in Example 10. Presumably, the lower background level of APA-bNA-hydrolysing activity in MS7 (compared to S. lividans) allowed the P5-4 and P5-15 clones to be identified. This has been noticed by other workers particularly relating to neutral protease activities in B. subtilis (Sloma et al. 1990).

Example 21

Following the teaching of Example 21 yet another protease-encoding gene was isolated from the same library screening experiment. Two clones were identified as being different (in terms of restriction enzyme sites) from the tap or ssp clones described in this application. Clone numbers P5-6 and P5-17 were shown to represent overlapping fragments of chromosomal DNA (FIG. 24) .

Figure 24:
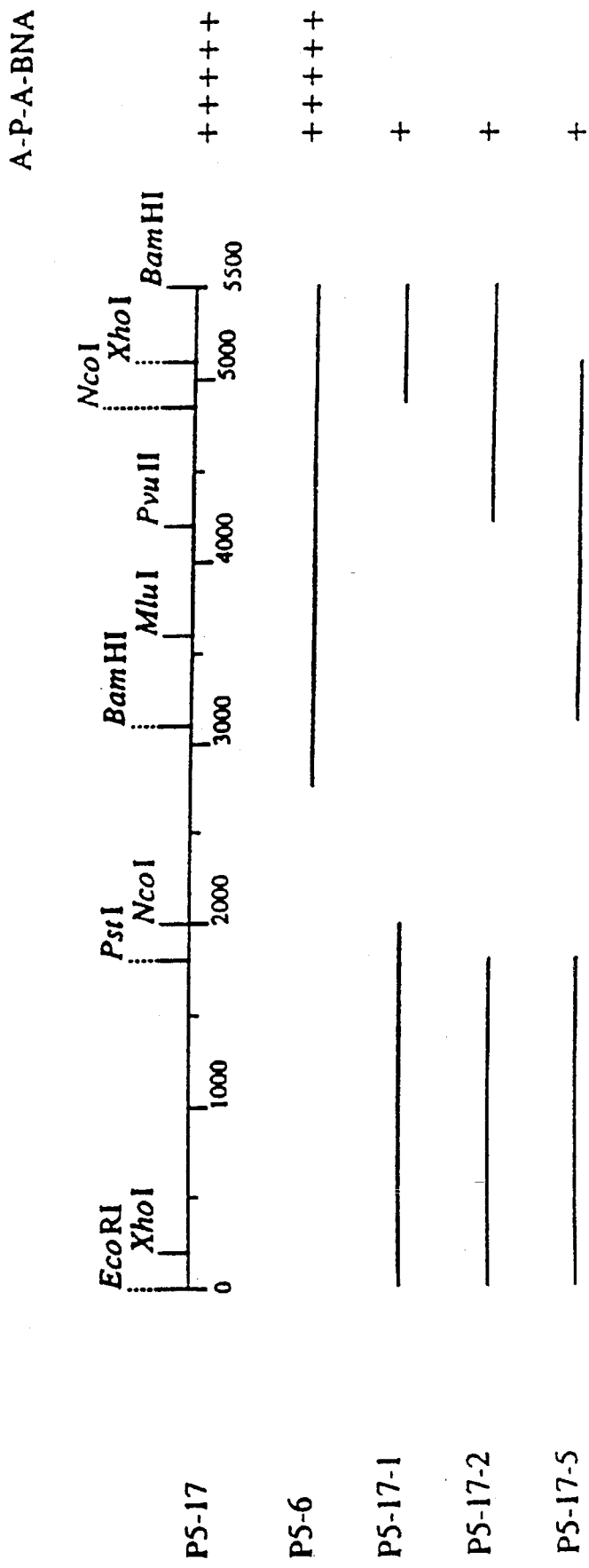
FIG. 24. Common restriction map for P5-6 and P5-15 and their deletion clones (SEQ ID NOS 7 and 8).

FIG. 24 shows the common restriction enzyme site map of the P5-6 and P5-17 DNA and deletion clones derived from P5-17. Activity against APA-bNA is shown by the number of asterisks adjacent to each plasmid and was estimated using the agar plate assay method described in Example 10.

Figure 31:
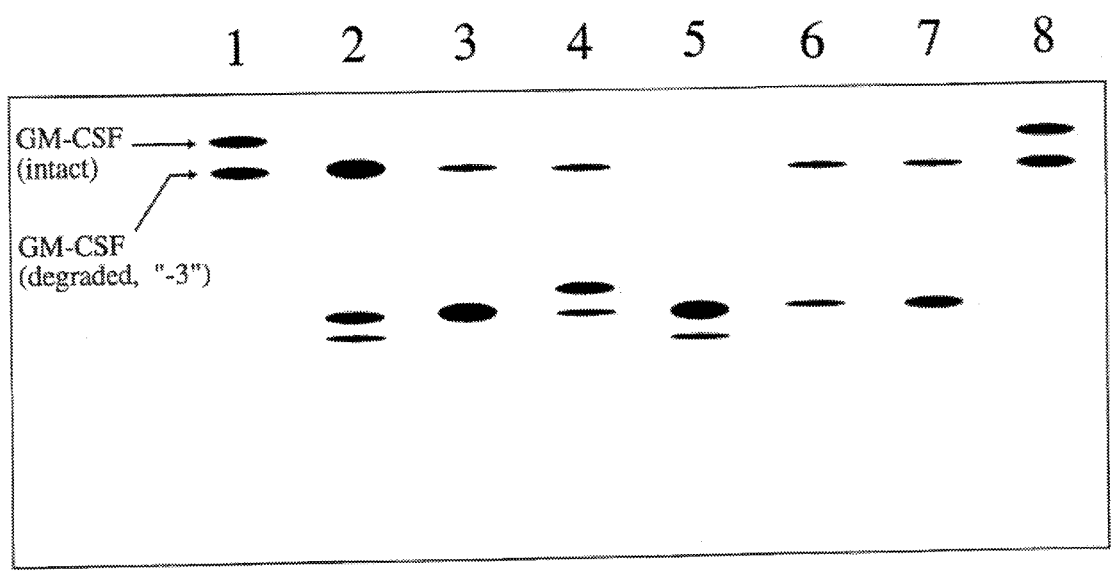
FIG. 31. Conversion of an intact GM-CSF to its "–3 form" upon incubation with fermentation culture supernatants from cells carrying P5-6, P5-10 and P5-17.

Although these clones encoded significant hydrolyric capability against the APA-bNA substrate in the agar plate assay, no activity above background was observed in cell-free broth derived from cultures containing these plasmids grown in TSB media. Neither was it possible to experimentally identify the protein product of this locus. When cultured in liquid medium resembling the agar medium composition (i.e. R2 without added phosphate or agar and containing 0.25% yeast extract—instead of the usual 0.5%) APA-bNA—degrading activity was observed in the cell-free broth. However, in contrast to the Tap and Ssp proteins, this activity was unable to hydrolyse GPL-bNA in R2, although it did show degradation of full-length GM-CSF according to the methods described in Example 2 (FIG. 31, lanes 3 and 7).

DNA sequence analysis of the P5-6 DNA (FIGS. 25A–25C, SEQ ID NOS 7 and 8) revealed a potential coding region. The predicted protein once again displayed a putative secretion signal peptide, followed by a predicted protein of 492 amino acid residues (FIGS 25A–25C ). Furthermore, when the amino acid sequence was compared to that of the Tap (FIGS 26, SEQ ID NOS 8 and 2) a strong homology was obvious around the region encoding the putative active site serine residue.

Plasmid deletion clones were constructed from P5-17 and shown to encode no activity above background in the agar plate assay.

Example 22

Figure 27:
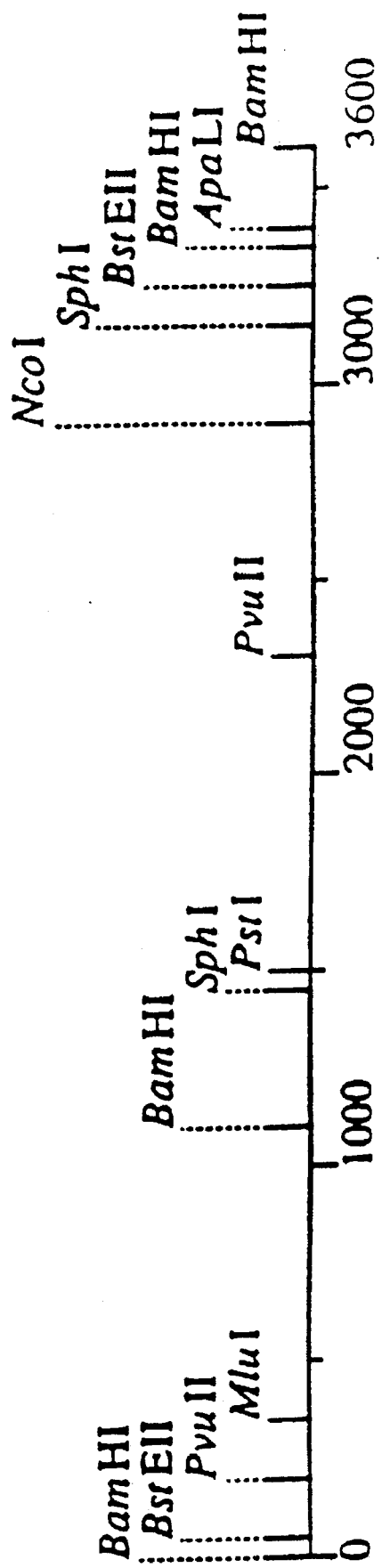
FIG. 27. Restriction map of P5-10 DNA.

Another cloned DNA fragment was isolated from the same APA-bNA screening experiment described in Examples 20 and 21. This DNA species was designated P5-10 and showed a different pattern of characteristic restriction enzyme sites (FIG. 27) than those observed for the other clones described above. A significant protein band was observed by SDS-PAGE analysis of supernatants of strains carrying this plasmid. Its molecular weight is approximately 50,000 daltons. Amino terminal amino acid sequence analysis was carried out according to the teaching of Example 13 yielding the following sequence (SEQ ID NO:13) Ala-Glu-Pro-Xaa-Ala$^5$-Val-Asp-Ile-Asp- Arg$^{10}$-Leu. The activity of supernatantmaterial containing this protein from MS7 host cultures, grown in TSB medium, was very low against APA-bNA and GPL-bNA. However, when cultured in R2YE liquid medium a high level of activity was observed against APA-bNA but not GPL-bNA. Furthermore, degradation of full-length GM-CSF according to the methods described in Example 2, was also detectable in samples grown in R2YE but not TSB (FIG. 31, lane 5).

Example 23

A chromogenic substrate was designed to model the amino terminal region of GM-CSF except that the amino terminal residue was modified by the addition of a Boc-group (or other similar moieties such as Fmoc), such that proteases whose activity requires a free $NH_2$-group would be unable to act directly on this substrate. However, any endoprotease present in the S. lividans host having a recognition sequence compatible with that of the substrate (specifically Boc-APARSPA-bNA) would be able to cleave and remove the Boc-group in addition to some portion of the peptide. Such cleavage would generate a smaller peptide-linked bNA moiety which now contains a free $NH_2$-group at the N-terminus and can be acted upon to release the chromogenic bNA moiety which can subsequently be visualized by reaction with Fast Garnet GBC dye.

Figure 28:
FIG. 28. Restriction map of P8-2 and its deletion clone.

This strategy was used to screen the S. lividans 66 genomic DNA library after transformation into the MS5 host strain (tap+). After screening of eight thousand colonies, six clones were confirmed to encode the ability to degrade the substrate significantly faster than the host strain alone. Two clones proved on restriction enzyme site analysis to be identical to P5-6 described in Example 21. Another clone was similarly shown to be the same as P5-17. Three other clones (P8-1, 2 and 3) were isolated and shown to represent the same region of chromosomal DNA (by Southern hybridization experiments). P8-3 contained a larger DNA fragment which was probably derived from the co-cloning of non-contiguous Sau3AI fragments in the construction of the library. P8-1 contained an inserted DNA fragment of approximately 8 kbp, while P8-2 had a smaller insert (3.6 kbp). Deletion mapping and DNA sequence analysis revealed a potential protein coding region in the central part of the cloned DNA (FIG. 28.) Comparison of the predicted protein sequence derived from the DNA sequence (FIG. 29) with those encoded by the tap and P5-6 clones showed a significant homology between the proteins encoded by P8-2 and P5-6. A smaller but still significant homology was detectable with the Tap protein. Specifically of interest is the conservation of amino acid sequences around the putanive active site serine residues of these proteins as follows:

Tap (residues 204–225 of SEQ ID NO: 2) G V S Y G T Y L G A V Y G T L F P D H V R R P5-6 (residues 199–220 of SEQ ID NO:8) G A S Y G T F L G A T Y A G L F P D R T G R P8-2 (residues 231–252 of SEQ ID NO:6) G I S Y G T E L G G V Y A H L F P E H V G R Example 24

Tap as a unique protease with a well established assay using a synthetic substrate for determination of its activity (described in this patent application, may be applied as a useful tool for immunoassay.

The uses of high performance immunoassay have increased greatly in the last decade, extending to almost every discipline in the life sciences. In the majority of applications, antibodies are labelled with enzymes, biotin or fluorochromes, and serve as components of a signal generating/amplifying system. This technology has a broad applicability and can be used in a wide variety of laboratory techniques including enzyme-linked immunosorbent-assay (ELISA), immunoblotting, immunohisto/cytochemistry and immunoelectrophoresis. In the following example we will show how one can use Tap in the most widely used technique—microwell ELISA.

In microwell ELISA, antigens are immobilized in a microwell and probed by labelled antibody (conjugate). The enzyme-labelled reagents are detected with the appropriate substrate, which is converted to a visible coloured product at the reaction site. The intensity of colour produced is proportional to the amount of measured antigen.

To date, the most common enzymes used for generating colour are alkaline phosphatase or horseradish peroxidase. In this example, we suggest replacing those enzymes with Tap and using the synthetic substrate, developed and described in this patent application, such as APA-pNA for visible colour and APA-AMC for fluorescence technology detection.

To demonstrate this idea, IL-3 was used as an example for antigen quantitation. Rabbit anti-IL-3 antisera (Cangene Corporation, Canada) was used as the first antibody. The second antibody, goat anti-rabbit IgG linked to biotin (Sigma, St. Louis, U.S.A.), and streptoavidin (Boehringer Mannhelm GmbH) were used as the amplification system.

Tap linked to biotin was used as the enzyme. The Tap was purified as described in Example 1 and 9.0 mL of the Tap (approximately 0.3 mg/mL) were biotinylated with D-Biotinyl-E-aminocaproic acid N-hydroxysuccinimide ester as described in Biochemia Bulletin of Boehringer Mannheim (1989, Antibodies and Reagents for Immunochemistry, p.115). Serial dilutions of recombinant hIL-3 (Cangene Corporation, Canada) were applied to the microplate wells (100 μL/well), and then incubated at 4° C. for over 16 hours. The wells were then washed and 5% BSA (bovine serum albumin) was added as a blocker. After 1 hour incubation, the wells were washed and rabbit anti hIL-3 sera (Cangene Corporation, Canada) was added at a dilution of 1/2000. Incubation was performed at 37° C. for 1 hour. The wells were then washed and the second antibody, goat anti-rabbit IgG-Biotin (Sigma), was added at a dilution of 1/2000 for 1 hour at 37° C. After washing, a mixture of Streptoavidin and Biotin-Tap was added. This mixture was prepared previously as follows: 40 μL of Streptoavidin (Boehringer Mannheim, 1 mg/mL) and 35 μL of Biotin-Tap were added to 5 mL Tris buffer pH 8.0 containing 1% BSA. The mixture was pre-incubated for 45 minutes before being added to the microplate assay. The mixture was washed from the microplate after incubation for 45 minutes at room temperature. Then 100 μL of the enzyme substrate (0.8 mM) were added. For colour developing, APA-pNA was used as a substrate and the assay was read after 2 and 16 hours incubation by absorbance at 405 nm. For faster analysis, APA-AMC was used as a fluorescent substrate, where the incubation was performed for 30 minutes and the assay was analyzed at exitation/emission of 400/450 nm by the multiwell plate scanning fluorescent system.

Figure 32A:
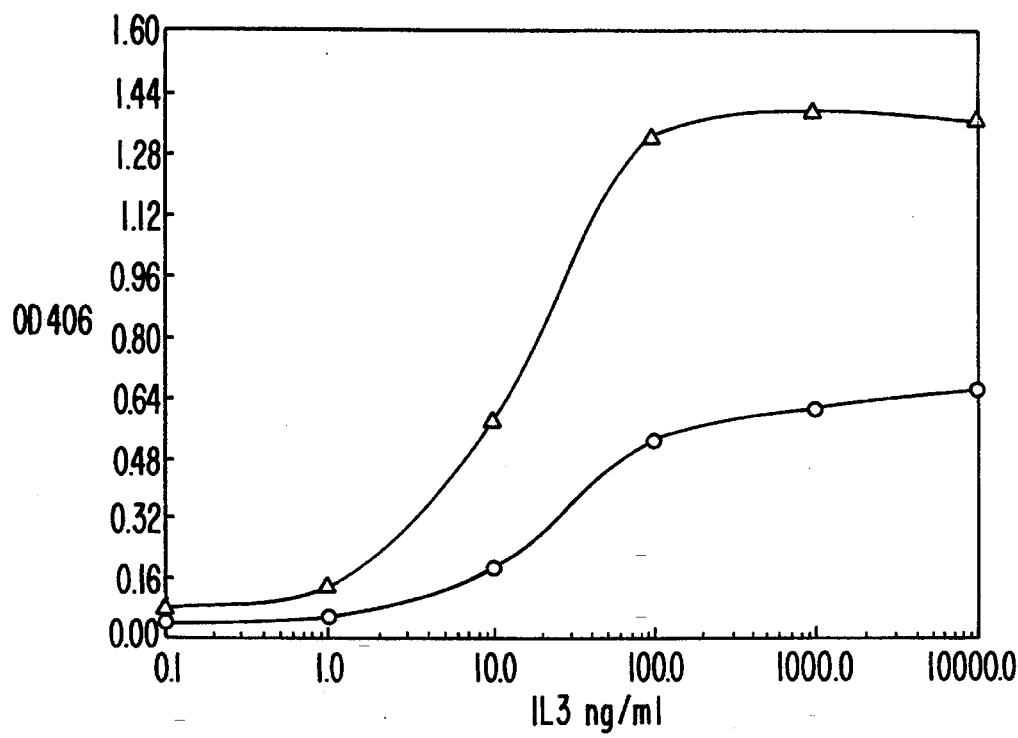
FIGS 32A–32B. Demonstration of the use of Tap in ELISA technology by standard calibration curve in hIL-3.
Figure 32B:
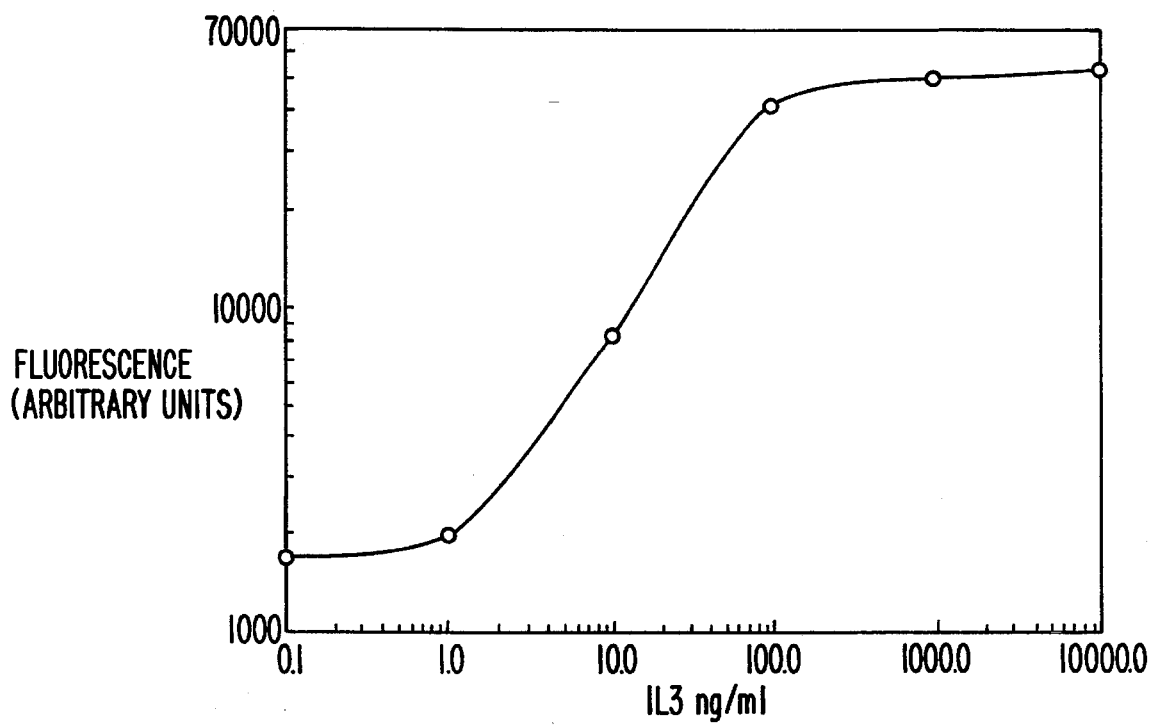

FIG. 32 shows a hIL-3 calibration curve using ELISA technology with Tap as the enzyme and APA-pNA as the substrate for colour forming (Panel A) incubated for either 2 hours (o---o) or 16 hours (Δ---Δ), and APA-AMC as a fluorescent substrate (Panel B) incubated 30 minutes.

There are some advantages to using Tap in the ELISA system compared to the common enzymes. The substates for Tap are much more stable and simple. The reaction can be incubated much longer and can be measured anytime without stopping the reaction. If necessary, the reaction can be stopped specifically by APA-CMK. Tap activity is not affected by peroxidases, catalases, phospatases, chelators, or sodium azide which may interfere with common ELISA enzymes. Using Tap in ELISA does not compromise the sensitivity and may even increase sensitivity by using fluorescent substrate.

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

REFERENCES

The references listed below are incorporated herein by reference to the extent that they supplement, explain, provide a background for, or teach methodology, techniques and/or compositions employed herein.

Atlan, D., P. Laloi and R. Portalier. 1989. Isolation and characterization of aminopeptidase-deficient *Lactobacillus bulgaricus* mutants. Appl. Env. Microbiol. 55:1717–1723.

Alvarez, N. G., C. Bordallo, S. Gascon and P. S. Rendueles. 1985. Purification and characterization of a thermosensitive X-prolyl dipeptidyl aminopeptidase from *S. cersvisiae*. BBA 832:119–125.

Aretz, W., K-P. Koller and G. Riess. 1989. Proteolytic enzymes from recombinant *Streptomyces lividans* TK24. FEMS Microbiol. Lett. 65:31–36.

Balon, R-M., Tomkinson, B., Ragnorsson, U. and Zetterqvist, O. 1986. J. Biol. Chem. Purification, Substrate Specificity and Classification of Tripeptidyl Peptidase II. 261 (5) 2409–2417.

Bender, E., K-P. Koller and J. W. Engels. 1990. Secretory synthesis of human interleukin-2 by *Streptomyces lividans*. Gene 86:227–232.

Bibb, M. J., M. J. Bibb, J. M. Ward and S.N. Cohen. 1985. Nucleotide sequences encoding and promoting expression of three antibiotic resistance genes indigenous to Streptomyces. Mol. Gen. Genet. 199:26–36.

Bibb, M. J., P. R. Findlay and M. W. Johnson. 1984. The relationship between base composition and codon usage in bacterial genes and its use for the simple and reliable identification of protein-coding sequences. Gene 30:157–166.

Brawher, M., D. Taylor and J. Fornwald. 1990. Expression of the soluble CD-4 receptor in Streptomyces. J. Cell. Biochem., supplement 14A p103.

Butler, M. J., C. C. Davey, P. Krygsman, E. Walczyk, and L. T. Malek. 1992. Cloning of genetic loci involved in endoprotease activity in *S. lividans* 66: a novel neutral protease gene with an adjacent divergent putative regulatory gene. Can. J. Microbiol., in the press.

Davies, B. J. 1964. Ann, N. Y. Acad. Sci. 121, 404

Doggette, P. E., and F. R. Blattner. 1986. Personal access of sequence databases on personal computers. Nucleic Acids Res. 14:611–619.

Fukusawa, K. M. and M. Harada. 1981. Purification and properties of dipeptidyl peptidase IV from *Streptococcus mitis* ATCC 9811. Arch. Biochem. Biophys. 210:230–237.

Hanson, H. and M. Frohne. 1976. Crystalline leucine aminopeptidase from lens in proteolytic enzymes (Ed., L. Lorand) Methods Enzymol. 45:504–521.

Henderson, G., P.Krygsman, C. J. Liu, C. C. Davey and L. T. Malek. 1987. Characterization and structure of genes for proteases A and B from *Streptomyces griseus*. 169:3778–3784.

Hopwood, D. A. , M. J. Bibb, K. F. Chater, T. Kieser, C. J. Bruton, H. M. Kieser, D. J. Lydiate, C. J. Thompson, C. P. Smith, J. M. Ward and H. Schrempf . 1985. Genetic manipulation of Streptomyces, a laboratory manual. The John Innes Foundation, Norwich, U. K.

Ingram, C., M. Brawner, P. Youngman and J. Westphaling. 1989. xylE functions as an efficient reporter gene in Streptomyces spp.: Use for the study of gal P1, a catabolite-controlled promoter. J. Bacteriol. 177:6617–6624.

Kreil, G. 1990. Processing of precursors by dipeptidyl aminopeptidases: a case of molecular ticketing. TIBS. 15:23–26.

Lloyd, R. J. and G. G. Pritchard. 1991. Characterization of X-prolyl dipeptidylaminopeptidase from Lactococcus lactis subsp. lactis. J. Gen. Microbiol. 137:49–55.

Malek, L. T., G. Soostmeyer, C. C. Davey, P. Krygsman, J. Compton, J. Gray, T. Zimny and D. Stewart. 1990. Secretion of Granulocyte Macrophase Colony Stimulating Factor (GM-CSF) in Streptomyces lividans. J. Cell. Biochem., supplement 14A, p127.

Maniatis, T., E. F. Fritsch and J. Sambrook. 1982. Molecular cloning: a laboratory manual. Cold Spring Harbor Laboratory, Cold Spring Harbor, N.Y.

McDonald J. K., Hoisington, A. R. and Eisenhauer, D. A. 1985. Partial Purification and Characterization of an Ovarian Tripeptidyl Peptidase: A lysosomal exopeptidase that sequentially releases Collagen-related (Gly-Pro-x) Triplets. 126:63–71.

Menn, F-M., Zylstra, G. J. & Gibson, D. T. 1991. Location and sequence of the tool F gene encoding 2-hydroxy-6-oxohepta-2, 4-dienoate hydrolase in Pseudom . . . putide F1. Gene 104:91–94.

Pearson, W. R. and D. J. Lipman. 1988. Improved tools for biological sequence comparison. Proc. Natl. Acad. Sci. USA. 85:2444–2448.

Schoellmann, G. and Shaw, E. 1963. Direct evidence for the presence of histidine in the active center of chymotrypsin. *Biochemistry*2:252.

Shaw, E., Mares-Guia, M., and Cohen, W. 1975. Evidence for an active center histidine in trypsin through the use of a specific reagent, TLCK, the chloromethyl ketone derived from N-tosyl-lysine. *Biochemistry*4:2219.

Sloma, A., Rufo, G. A., Jr. and Pero, J. Residual protease III WO, A, 92/16642 (see page enclosed)

Tagakuchi, S., I. Kumagai, J. Nakayama, A. Suzuki and K. Miura. 1989. Efficient extracelluar expression of a foreign protein in Streptomyces using secretory protease inhibitor (SSI) gene fusions. Biotechnology 7:1063–66.

Tinoco, I., Jr., P. N. Borer, B. Dengler, M. D. Levine, O. C. Uhlenbech D. M. Crothers and J. Gralla. 1973. Improved estimation of secondary structure in ribonucleic acid. Nature New Biol. 246:40–41.

Tomkinson, B. and Jonsson, A-K. 1991. Characterization of cDNA for Human Tripeptidyl Peptidase II: The N-Terminal Part of the Enzyme is Similar to Subtilising. Biochemistry 30:168–174. White, Handler, and Smith. 1973.

Wilbur, W. J. and D. J. Lipman. 1983. Rapid Similarity searches of nucleic acid and protein data banks. Proc. Natl. Acad. Sci. USA. 80:726–730.

Yoshimoto, T., N. Murayama, T. Honda, H. Tone, and D. Tsuru. 1988. Cloning and expression of aminopeptidase P gene from *E. coli* HB101 and characterization of expressed enzyme. J. Biochem. 104:93–97.

Yoshimoto, T., H. Tone, T. Honda, K. Osatomi, R. Kobayashi, and D. Tsuru. 1989. Sequencing and high expression of aminopeptidase P gene from *E. coli* HB101. J. Biochem. 105:412–416.

---

We claim:

1. An isolated nucleotide molecule encoding a protease, wherein said protease is selected from the group of proteases encoded by nucleotide sequences consisting of SEQ ID NO:1, SEQ ID NO:3, SEQ ID NO:5 and SEQ ID NO:7.

2. An isolated nucleotide molecule isolated from Streptomyces that (i) hybridizes with a molecule encoding a tripeptidyl aminopeptidase having the amino acid sequence of SEQ ID NO:2, under conditions of 5×SSC for 30 minutes at 68 degrees Celsius, and (ii) encodes a protease that hydrolyzes APA-pNA to yield p-nitroaniline.

3. An isolated mutated nucleotide molecule encoding an inactivated protease, wherein said mutated nucleotide molecule has a mutation that inactivates a protease encoded by a nucleotide sequence selected from the group consisting of SEQ ID NO:1, SEQ ID NO:3, SEQ ID NO:5, and SEQ ID NO:7, and wherein said mutation is selected from the group consisting of one or more nucleotide substitutions, one or more nucleotide deletions and both one or more nucleotide substitutions and one or more nucleotide deletions.

4. A mutated molecule according to claim 3, that lacks all or a part of a molecule having SEQ ID NO:1 that is depicted between BamHI sites 2 and 8 of FIG. 8A.

5. A mutated molecule according to claim 3, that lacks all or a part of a molecule having SEQ ID NO:1 that is depicted between Bgl II sites 5 and 7 of FIG. 8A.

6. A *Streptomyces lividans* 66 strain comprising a mutated nucleotide molecule encoding an inactivated protease according to claim 3.

7. A Streptomyces strain comprising a mutated molecule according to claim 3, wherein said mutated molecule is made with respect to a moleucle having SEQ ID NO:1.

8. The strain of claim 7, selected from the group consisting of the species *S. lividans, S. ambofaciens, S. coelicolor, S. alboniger, S. fradiae, S. griseus, S. parvulus, and S. rimosus*.

9. The strain of claim 7, which expresses an exogenous gene product.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 1908 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 146..1759

( i x ) FEATURE:
        ( A ) NAME/KEY: misc_feature
        ( B ) LOCATION: 146..148
        ( D ) OTHER INFORMATION: /note="Met at position -39 represents fMet"

( i x ) FEATURE:
        ( A ) NAME/KEY: sig_peptide
        ( B ) LOCATION: 146..262

( i x ) FEATURE:
        ( A ) NAME/KEY: mat_peptide
        ( B ) LOCATION: 263..1756

( x i ) SEQUENCE DESCRIPTION: SEQ ID NO:1:

```
GGCGGGGACC  GGCCGACGGC  CCCGCCGAAC  GAACGCCCTT  CTCCGTTTAT  CGGATTGGCA              60

AAGAAGTAGC  ACTGGCCCTG  TTCTCAGGAA  ACCCACAGCG  GCGAGGATCC  CCGTACTTGT             120

CGCGAACACG  TACGGGGAGG  GCCAC TTG  AGG  AAG  AGC  AGC  ATA  CGG  CGG  AGG         172
                              Met  Arg  Lys  Ser  Ser  Ile  Arg  Arg  Arg
                              -39            -35

GCG  ACC  GCC  TTC  GGC  ACG  GCC  GGA  GCA  CTG  GTC  ACC  GCC  ACG  CTG  ATC   220
Ala  Thr  Ala  Phe  Gly  Thr  Ala  Gly  Ala  Leu  Val  Thr  Ala  Thr  Leu  Ile
```

|  | -30 |  |  |  | -25 |  |  |  |  | -20 |  |  |  |  | -15 |  |  |
|---|---|---|---|---|---|---|---|---|---|---|---|---|---|---|---|---|---|
| GCC | GGC | GCC | GTC | TCG | GCA | CCC | GCC | GCG | AGC | GCC | GCC | CCG | GCC | GAC | GGC | 268 |
| Ala | Gly | Ala | Val | Ser | Ala | Pro | Ala | Ala | Ser | Ala | Ala | Pro | Ala | Asp | Gly |  |
|  |  |  |  | -10 |  |  |  |  | -5 |  |  |  |  |  | 1 |  |

| CAC | GGG | CAC | GGG | CGG | AGC | TGG | GAC | CGG | GAG | GCG | CGC | GGT | GCC | GCC | ATC | 316 |
|---|---|---|---|---|---|---|---|---|---|---|---|---|---|---|---|---|
| His | Gly | His | Gly | Arg | Ser | Trp | Asp | Arg | Glu | Ala | Arg | Gly | Ala | Ala | Ile |  |
|  |  | 5 |  |  |  |  | 10 |  |  |  |  |  | 15 |  |  |  |

| GCC | GCC | GCC | CGC | GCC | GCC | CGG | GCG | GGC | ATC | GAC | TGG | GAG | GAC | TGC | GCA | 364 |
|---|---|---|---|---|---|---|---|---|---|---|---|---|---|---|---|---|
| Ala | Ala | Ala | Arg | Ala | Ala | Arg | Ala | Gly | Ile | Asp | Trp | Glu | Asp | Cys | Ala |  |
|  | 20 |  |  |  | 25 |  |  |  |  | 30 |  |  |  |  |  |  |

| GCC | GAC | TGG | AAC | CTG | CCC | AAG | CCC | ATC | CAG | TGC | GGC | TAC | GTC | ACG | GTG | 412 |
|---|---|---|---|---|---|---|---|---|---|---|---|---|---|---|---|---|
| Ala | Asp | Trp | Asn | Leu | Pro | Lys | Pro | Ile | Gln | Cys | Gly | Tyr | Val | Thr | Val |  |
| 35 |  |  |  |  | 40 |  |  |  |  | 45 |  |  |  |  | 50 |  |

| CCG | ATG | GAC | TAC | GCC | AAG | CCG | TAC | GGC | AAG | CAG | ATC | AGG | CTC | GCC | GTC | 460 |
|---|---|---|---|---|---|---|---|---|---|---|---|---|---|---|---|---|
| Pro | Met | Asp | Tyr | Ala | Lys | Pro | Tyr | Gly | Lys | Gln | Ile | Arg | Leu | Ala | Val |  |
|  |  |  |  | 55 |  |  |  |  | 60 |  |  |  |  | 65 |  |  |

| GAC | CGC | ATC | GGC | AAC | ACC | GGA | ACC | AGG | AGC | GAG | CGC | CAG | GGC | GCC | CTG | 508 |
|---|---|---|---|---|---|---|---|---|---|---|---|---|---|---|---|---|
| Asp | Arg | Ile | Gly | Asn | Thr | Gly | Thr | Arg | Ser | Glu | Arg | Gln | Gly | Ala | Leu |  |
|  |  |  | 70 |  |  |  |  | 75 |  |  |  |  | 80 |  |  |  |

| ATC | TAC | AAC | CCC | GGC | GGT | CCC | GGC | GGC | TCC | GGC | CTG | CGT | TTC | CCG | GCC | 556 |
|---|---|---|---|---|---|---|---|---|---|---|---|---|---|---|---|---|
| Ile | Tyr | Asn | Pro | Gly | Gly | Pro | Gly | Gly | Ser | Gly | Leu | Arg | Phe | Pro | Ala |  |
|  |  | 85 |  |  |  |  | 90 |  |  |  |  | 95 |  |  |  |  |

| CGC | GTC | ACG | AAC | AAG | AGC | GCG | GTC | TGG | GCC | AAC | ACG | GCC | AAG | GCC | TAC | 604 |
|---|---|---|---|---|---|---|---|---|---|---|---|---|---|---|---|---|
| Arg | Val | Thr | Asn | Lys | Ser | Ala | Val | Trp | Ala | Asn | Thr | Ala | Lys | Ala | Tyr |  |
| 100 |  |  |  |  | 105 |  |  |  |  | 110 |  |  |  |  |  |  |

| GAC | TTC | GTC | GGC | TTC | GAC | CCG | CGC | GGC | GTC | GGC | CAC | TCC | GCG | CCC | ATC | 652 |
|---|---|---|---|---|---|---|---|---|---|---|---|---|---|---|---|---|
| Asp | Phe | Val | Gly | Phe | Asp | Pro | Arg | Gly | Val | Gly | His | Ser | Ala | Pro | Ile |  |
| 115 |  |  |  |  | 120 |  |  |  |  | 125 |  |  |  |  | 130 |  |

| TCC | TGC | GTC | GAC | CCG | CAG | GAG | TTC | GTC | AAG | GCA | CCC | AAG | GCC | GAC | CCC | 700 |
|---|---|---|---|---|---|---|---|---|---|---|---|---|---|---|---|---|
| Ser | Cys | Val | Asp | Pro | Gln | Glu | Phe | Val | Lys | Ala | Pro | Lys | Ala | Asp | Pro |  |
|  |  |  |  | 135 |  |  |  |  | 140 |  |  |  |  | 145 |  |  |

| GTG | CCC | GGC | TCC | GAG | GCC | GAC | AAG | CGC | GCC | CAG | CGC | AAG | CTC | GCC | CGC | 748 |
|---|---|---|---|---|---|---|---|---|---|---|---|---|---|---|---|---|
| Val | Pro | Gly | Ser | Glu | Ala | Asp | Lys | Arg | Ala | Gln | Arg | Lys | Leu | Ala | Arg |  |
|  |  |  | 150 |  |  |  |  | 155 |  |  |  |  | 160 |  |  |  |

| GAG | TAC | GCC | GAG | GGC | TGC | TTC | GAG | CGC | AGC | GGC | GAG | ATG | CTC | CCG | CAC | 796 |
|---|---|---|---|---|---|---|---|---|---|---|---|---|---|---|---|---|
| Glu | Tyr | Ala | Glu | Gly | Cys | Phe | Glu | Arg | Ser | Gly | Glu | Met | Leu | Pro | His |  |
|  |  | 165 |  |  |  |  | 170 |  |  |  |  | 175 |  |  |  |  |

| ATG | ACC | ACG | CCG | AAC | ACC | GCG | CGC | GAC | CTC | GAC | GTC | ATC | CGC | GCC | GCC | 844 |
|---|---|---|---|---|---|---|---|---|---|---|---|---|---|---|---|---|
| Met | Thr | Thr | Pro | Asn | Thr | Ala | Arg | Asp | Leu | Asp | Val | Ile | Arg | Ala | Ala |  |
| 180 |  |  |  |  | 185 |  |  |  |  | 190 |  |  |  |  |  |  |

| CTC | GGC | GAG | AAG | AAG | CTC | AAC | TAC | CTC | GGC | GTC | TCC | TAC | GGC | ACC | TAC | 892 |
|---|---|---|---|---|---|---|---|---|---|---|---|---|---|---|---|---|
| Leu | Gly | Glu | Lys | Lys | Leu | Asn | Tyr | Leu | Gly | Val | Ser | Tyr | Gly | Thr | Tyr |  |
| 195 |  |  |  |  | 200 |  |  |  |  | 205 |  |  |  |  | 210 |  |

| CTC | GGC | GCC | GTC | TAC | GGC | ACC | CTC | TTC | CCG | GAC | CAC | GTC | CGC | CGC | ATG | 940 |
|---|---|---|---|---|---|---|---|---|---|---|---|---|---|---|---|---|
| Leu | Gly | Ala | Val | Tyr | Gly | Thr | Leu | Phe | Pro | Asp | His | Val | Arg | Arg | Met |  |
|  |  |  |  | 215 |  |  |  |  | 220 |  |  |  |  | 225 |  |  |

| GTC | GTC | GAC | AGC | GTC | GTC | AAC | CCG | TCC | CGC | GAC | AAG | ATC | TGG | TAC | CAG | 988 |
|---|---|---|---|---|---|---|---|---|---|---|---|---|---|---|---|---|
| Val | Val | Asp | Ser | Val | Val | Asn | Pro | Ser | Arg | Asp | Lys | Ile | Trp | Tyr | Gln |  |
|  |  |  | 230 |  |  |  |  | 235 |  |  |  |  | 240 |  |  |  |

| GCC | AAC | CTG | GAC | CAG | GAC | GTC | GCC | TTC | GAG | GGC | CGC | TGG | AAG | GAC | TGG | 1036 |
|---|---|---|---|---|---|---|---|---|---|---|---|---|---|---|---|---|
| Ala | Asn | Leu | Asp | Gln | Asp | Val | Ala | Phe | Glu | Gly | Arg | Trp | Lys | Asp | Trp |  |
|  |  | 245 |  |  |  |  | 250 |  |  |  |  | 255 |  |  |  |  |

| CAG | GAC | TGG | GTC | GCC | GCG | AAC | GAC | GCC | GCC | TAC | CAC | CTC | GGC | GAC | ACC | 1084 |
|---|---|---|---|---|---|---|---|---|---|---|---|---|---|---|---|---|
| Gln | Asp | Trp | Val | Ala | Ala | Asn | Asp | Ala | Ala | Tyr | His | Leu | Gly | Asp | Thr |  |
| 260 |  |  |  |  | 265 |  |  |  |  | 270 |  |  |  |  |  |  |

| CGC | GCC | GAG | GTC | CAG | GAC | CAG | TGG | CTG | AAG | CTG | CGC | GCC | GCC | GCC | GCG | 1132 |
|---|---|---|---|---|---|---|---|---|---|---|---|---|---|---|---|---|
| Arg | Ala | Glu | Val | Gln | Asp | Gln | Trp | Leu | Lys | Leu | Arg | Ala | Ala | Ala | Ala |  |
| 275 |  |  |  |  | 280 |  |  |  |  | 285 |  |  |  |  | 290 |  |

| AAG | AAG | CCG | CTG | GGC | GGC | GTC | GTC | GGA | CCG | GCC | GAG | CTG | ATC | TCC | TTC | 1180 |
|---|---|---|---|---|---|---|---|---|---|---|---|---|---|---|---|---|
| Lys | Lys | Pro | Leu | Gly | Gly | Val | Val | Gly | Pro | Ala | Glu | Leu | Ile | Ser | Phe |  |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 295 |     |     |     |     | 300 |     |     |     |     |     | 305 |     |      |
| TTC | CAG | AGC | GCC | CCG | TAC | TAC | GAC | TCC | GCC | TGG | GCG | CCG | ACC | GCG | GAG | 1228 |
| Phe | Gln | Ser | Ala | Pro | Tyr | Tyr | Asp | Ser | Ala | Trp | Ala | Pro | Thr | Ala | Glu |      |
|     |     |     | 310 |     |     |     |     | 315 |     |     |     |     | 320 |     |     |      |
| ATC | TTC | AGC | AAG | TAC | GTC | GCC | GGC | GAC | ACC | CAG | GCG | CTC | GTC | GAC | GCC | 1276 |
| Ile | Phe | Ser | Lys | Tyr | Val | Ala | Gly | Asp | Thr | Gln | Ala | Leu | Val | Asp | Ala |      |
|     |     | 325 |     |     |     |     |     | 330 |     |     |     | 335 |     |     |     |      |
| GCC | GCA | CCC | GAC | CTG | TCC | GAC | ACC | GCG | GGC | AAC | GCC | TCC | GCG | GAG | AAC | 1324 |
| Ala | Ala | Pro | Asp | Leu | Ser | Asp | Thr | Ala | Gly | Asn | Ala | Ser | Ala | Glu | Asn |      |
|     | 340 |     |     |     |     | 345 |     |     |     |     | 350 |     |     |     |     |      |
| GGC | AAC | GCC | GTC | TAC | ACG | GCC | GTC | GAG | TGC | ACC | GAC | GCC | AAG | TGG | CCC | 1372 |
| Gly | Asn | Ala | Val | Tyr | Thr | Ala | Val | Glu | Cys | Thr | Asp | Ala | Lys | Trp | Pro |      |
| 355 |     |     |     |     | 360 |     |     |     |     | 365 |     |     |     |     | 370 |      |
| GCC | AAC | TGG | CGC | ACC | TGG | GAC | CGG | GAC | AAC | ACC | CGG | CTC | CAC | CGC | GAC | 1420 |
| Ala | Asn | Trp | Arg | Thr | Trp | Asp | Arg | Asp | Asn | Thr | Arg | Leu | His | Arg | Asp |      |
|     |     |     |     | 375 |     |     |     |     | 380 |     |     |     |     | 385 |     |      |
| CAC | CCG | TTC | ATG | ACC | TGG | GCC | AAC | GCC | TGG | ATG | AAC | CTG | CCC | TGT | GCC | 1468 |
| His | Pro | Phe | Met | Thr | Trp | Ala | Asn | Ala | Trp | Met | Asn | Leu | Pro | Cys | Ala |      |
|     |     |     | 390 |     |     |     |     | 395 |     |     |     |     | 400 |     |     |      |
| ACC | TGG | CCG | GTC | AAG | CAG | CAG | ACC | CCG | CTG | AAC | GTG | AAG | ACC | GGC | AAG | 1516 |
| Thr | Trp | Pro | Val | Lys | Gln | Gln | Thr | Pro | Leu | Asn | Val | Lys | Thr | Gly | Lys |      |
|     |     | 405 |     |     |     |     |     | 410 |     |     |     | 415 |     |     |     |      |
| GGA | CTT | CCG | CCG | GTG | CTG | ATC | GTC | CAG | TCC | GAG | CGT | GAC | GCC | GCC | ACC | 1564 |
| Gly | Leu | Pro | Pro | Val | Leu | Ile | Val | Gln | Ser | Glu | Arg | Asp | Ala | Ala | Thr |      |
|     | 420 |     |     |     |     | 425 |     |     |     |     | 430 |     |     |     |     |      |
| CCG | TAC | GAG | GGC | GCC | GTC | GAA | CTG | CAC | CAG | CGG | TTC | CGG | GGA | TCC | CGC | 1612 |
| Pro | Tyr | Glu | Gly | Ala | Val | Glu | Leu | His | Gln | Arg | Phe | Arg | Gly | Ser | Arg |      |
| 435 |     |     |     |     | 440 |     |     |     |     | 445 |     |     |     |     | 450 |      |
| CTG | ATC | ACC | GAG | CGG | GAC | GCC | GGC | TCC | CAC | GGC | GTC | ACC | GGC | CTG | GTC | 1660 |
| Leu | Ile | Thr | Glu | Arg | Asp | Ala | Gly | Ser | His | Gly | Val | Thr | Gly | Leu | Val |      |
|     |     |     |     | 455 |     |     |     |     | 460 |     |     |     |     | 465 |     |      |
| AAC | CCG | TGC | ATC | AAC | GAC | CGG | GTC | GAC | ACC | TAC | CTG | CTC | ACC | GGC | AGG | 1708 |
| Asn | Pro | Cys | Ile | Asn | Asp | Arg | Val | Asp | Thr | Tyr | Leu | Leu | Thr | Gly | Arg |      |
|     |     |     | 470 |     |     |     |     | 475 |     |     |     |     | 480 |     |     |      |
| ACG | GAC | GCC | CGC | GAC | GTG | ACC | TGC | GCG | CCG | CAC | GCC | ACG | CCC | AGG | CCG | 1756 |
| Thr | Asp | Ala | Arg | Asp | Val | Thr | Cys | Ala | Pro | His | Ala | Thr | Pro | Arg | Pro |      |
|     |     | 485 |     |     |     |     | 490 |     |     |     |     | 495 |     |     |     |      |

| TAACCCGGGC | TCAGGCCAAG | CGGGGGGAGG | GGGCGACCGG | TCCGACCGGC | CGCCCCTCC | 1816 |
| CCCCACCTGT | CGCTACCGTC | CCTCGGCCCA | GGCGTCCTCC | GCCGCGTAGT | CGAAGAGGTC | 1876 |
| GCCGTACGCC | TTGAACATCT | TCGGGTAGGC | CT         |            |           | 1908 |

( 2 ) INFORMATION FOR SEQ ID NO:2:

( i ) SEQUENCE CHARACTERISTICS:
        ( A ) LENGTH: 537 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|     |     |     |     |     |     |     |     |     |     |     |     |     |     |
|-----|-----|-----|-----|-----|-----|-----|-----|-----|-----|-----|-----|-----|-----|
| Met | Arg | Lys | Ser | Ser | Ile | Arg | Arg | Arg | Ala | Thr | Ala | Phe | Gly | Thr | Ala |
| -39 |     |     |     | -35 |     |     |     | -30 |     |     |     | -25 |     |     |     |
| Gly | Ala | Leu | Val | Thr | Ala | Thr | Leu | Ile | Ala | Gly | Ala | Val | Ser | Ala | Pro |
|     |     |     | -20 |     |     |     | -15 |     |     |     | -10 |     |     |     |     |
| Ala | Ala | Ser | Ala | Ala | Pro | Ala | Asp | Gly | His | Gly | His | Gly | Arg | Ser | Trp |
|     |     | -5  |     |     |     | 1   |     |     |     | 5   |     |     |     |     |     |
| Asp | Arg | Glu | Ala | Arg | Gly | Ala | Ala | Ile | Ala | Ala | Ala | Arg | Ala | Ala | Arg |
| 10  |     |     |     |     | 15  |     |     |     | 20  |     |     |     |     | 25  |     |

| | | | | | | | | | | | | | |
|---|---|---|---|---|---|---|---|---|---|---|---|---|---|
| Ala | Gly | Ile | Asp | Trp 30 | Glu | Asp | Cys | Ala | Ala 35 | Asp | Trp | Asn | Leu | Pro 40 | Lys |
| Pro | Ile | Gln | Cys 45 | Gly | Tyr | Val | Thr | Val 50 | Pro | Met | Asp | Tyr | Ala 55 | Lys | Pro |
| Tyr | Gly | Lys 60 | Gln | Ile | Arg | Leu | Ala 65 | Val | Asp | Arg | Ile | Gly 70 | Asn | Thr | Gly |
| Thr | Arg 75 | Ser | Glu | Arg | Gln | Gly 80 | Ala | Leu | Ile | Tyr | Asn 85 | Pro | Gly | Gly | Pro |
| Gly 90 | Gly | Ser | Gly | Leu | Arg 95 | Phe | Pro | Ala | Arg | Val 100 | Thr | Asn | Lys | Ser | Ala 105 |
| Val | Trp | Ala | Asn | Thr 110 | Ala | Lys | Ala | Tyr | Asp 115 | Phe | Val | Gly | Phe | Asp 120 | Pro |
| Arg | Gly | Val | Gly 125 | His | Ser | Ala | Pro | Ile 130 | Ser | Cys | Val | Asp | Pro 135 | Gln | Glu |
| Phe | Val | Lys 140 | Ala | Pro | Lys | Ala | Asp 145 | Pro | Val | Pro | Gly | Ser 150 | Glu | Ala | Asp |
| Lys | Arg 155 | Ala | Gln | Arg | Lys | Leu 160 | Ala | Arg | Glu | Tyr | Ala 165 | Glu | Gly | Cys | Phe |
| Glu 170 | Arg | Ser | Gly | Glu | Met 175 | Leu | Pro | His | Met | Thr 180 | Thr | Pro | Asn | Thr | Ala 185 |
| Arg | Asp | Leu | Asp | Val 190 | Ile | Arg | Ala | Ala | Leu 195 | Gly | Glu | Lys | Lys | Leu 200 | Asn |
| Tyr | Leu | Gly | Val 205 | Ser | Tyr | Gly | Thr | Tyr 210 | Leu | Gly | Ala | Val | Tyr 215 | Gly | Thr |
| Leu | Phe | Pro 220 | Asp | His | Val | Arg | Arg 225 | Met | Val | Val | Asp | Ser 230 | Val | Val | Asn |
| Pro | Ser 235 | Arg | Asp | Lys | Ile | Trp 240 | Tyr | Gln | Ala | Asn | Leu 245 | Asp | Gln | Asp | Val |
| Ala 250 | Phe | Glu | Gly | Arg | Trp 255 | Lys | Asp | Trp | Gln | Asp 260 | Trp | Val | Ala | Ala | Asn 265 |
| Asp | Ala | Ala | Tyr | His 270 | Leu | Gly | Asp | Thr | Arg 275 | Ala | Glu | Val | Gln | Asp 280 | Gln |
| Trp | Leu | Lys | Leu 285 | Arg | Ala | Ala | Ala | Lys 290 | Lys | Pro | Leu | Gly 295 | Gly | Val |
| Val | Gly | Pro 300 | Ala | Glu | Leu | Ile | Ser 305 | Phe | Phe | Gln | Ser | Ala 310 | Pro | Tyr | Tyr |
| Asp | Ser 315 | Ala | Trp | Ala | Pro | Thr 320 | Ala | Glu | Ile | Phe | Ser 325 | Lys | Tyr | Val | Ala |
| Gly 330 | Asp | Thr | Gln | Ala | Leu 335 | Val | Asp | Ala | Ala | Ala 340 | Pro | Asp | Leu | Ser | Asp 345 |
| Thr | Ala | Gly | Asn | Ala 350 | Ser | Ala | Glu | Asn | Gly 355 | Asn | Ala | Val | Tyr | Thr 360 | Ala |
| Val | Glu | Cys | Thr 365 | Asp | Ala | Lys | Trp | Pro 370 | Ala | Asn | Trp | Arg | Thr 375 | Trp | Asp |
| Arg | Asp | Asn 380 | Thr | Arg | Leu | His | Arg 385 | Asp | His | Pro | Phe | Met 390 | Thr | Trp | Ala |
| Asn | Ala 395 | Trp | Met | Asn | Leu | Pro 400 | Cys | Ala | Thr | Trp | Pro 405 | Val | Lys | Gln | Gln |
| Thr 410 | Pro | Leu | Asn | Val | Lys 415 | Thr | Gly | Lys | Gly | Leu 420 | Pro | Pro | Val | Leu | Ile 425 |
| Val | Gln | Ser | Glu | Arg 430 | Asp | Ala | Ala | Thr | Pro 435 | Tyr | Glu | Gly | Ala | Val 440 | Glu |
| Leu | His | Gln | Arg 445 | Phe | Arg | Gly | Ser | Arg 450 | Leu | Ile | Thr | Glu | Arg 455 | Asp | Ala |

```
Gly Ser His Gly Val Thr Gly Leu Val Asn Pro Cys Ile Asn Asp Arg
        460                 465                 470

Val Asp Thr Tyr Leu Leu Thr Gly Arg Thr Asp Ala Arg Asp Val Thr
    475                 480                 485

Cys Ala Pro His Ala Thr Pro Arg Pro
490                 495
```

( 2 ) INFORMATION FOR SEQ ID NO:3:

( i ) SEQUENCE CHARACTERISTICS:
        ( A ) LENGTH: 2185 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 531..2069

( i x ) FEATURE:
        ( A ) NAME/KEY: sig_peptide
        ( B ) LOCATION: 531..902

( i x ) FEATURE:
        ( A ) NAME/KEY: mat_peptide
        ( B ) LOCATION: 903..2069

( i x ) FEATURE:
        ( A ) NAME/KEY: misc_feature
        ( B ) LOCATION: 531..533
        ( D ) OTHER INFORMATION: /note="Met at position -124 represents fMet"

( x i ) SEQUENCE DESCRIPTION: SEQ ID NO:3:

```
GGTACCAGGC GACGAAGGCG ACGGTCAGCG GGAACGCGAA GGAACGGAAG GAGCGGCGCA     60

GTTCGGCGAA CTCGGCGCTC TGCTGCACTT CGGAGAACTC CTCGGCGGAG GGGAGGCGGT    120

GCTCCTCTTG CGAGGGGGGC TCCTCTTTGG AGGGGGGCGG TGCGTCGGGT GGCCACGGAG    180

TCTCCTCGTA CGACGGACAT GACGGCTTGG ACCTCGGTGT CTCGCAGGG GGCTGATCGT     240

GCTCGGGCTC CCTGTCCAAC GACACGGCGC CCCGCGGGGC CCGGTTCAAC ACCCGTGGCA    300

CTTTCCGAAG TCGTCCTCGG CGGGTCATTG CTGGCCAGGG ACTTCGGGGG ATAGCTTCAC    360

CCTGCACCAC TACGTCATGT ACCTGCCCGG CCCGTTTCAC CCGTGCCCGG GCAGGTGCTG    420

TTTGCCGGAT GATGTGGAGA CCCCATGGAT CATCTGCGCT TCCCGCGCGA CCCGCGCTCC    480

AGACGCGGGC TCGTTTCCCG AGCTTTCCCG ACGGACTGGA GACATCACGC ATG ACC       536
                                                        Met Thr
                                                        -124

GCT CCC CTC TCG CGT CAC CGC CGT GCC CTC GCG ATT CCG GCG GGC CTG      584
Ala Pro Leu Ser Arg His Arg Arg Ala Leu Ala Ile Pro Ala Gly Leu
        -120                -115                -110

GCC GTG GCC GCG TCG CTC GCG TTC CTG CCG GGC ACC CCG GCC GCC GCG      632
Ala Val Ala Ala Ser Leu Ala Phe Leu Pro Gly Thr Pro Ala Ala Ala
-105                -100                -95

ACC CCC GCG GCC GAG GCC GCG CCC TCG ACG GCG GCG GAC GCG ACC TCG      680
Thr Pro Ala Ala Glu Ala Ala Pro Ser Thr Ala Ala Asp Ala Thr Ser
-90                 -85                 -80                 -75

CTC AGC TAC GTC GTC AAC GTC GCC TCC GGG CAC CGT CCT TCG GCC ACC      728
Leu Ser Tyr Val Val Asn Val Ala Ser Gly His Arg Pro Ser Ala Thr
            -70                 -65                 -60

GTG CGG CGG GCG ATA GCC AAG GCG GGC GGC ACG ATC GTC ACG TCG TAC      776
Val Arg Arg Ala Ile Ala Lys Ala Gly Gly Thr Ile Val Thr Ser Tyr
        -55                 -50                 -45

GAC CGG ATC GGC GTG ATC GTC GTC CAC TCC GCC AAC CCC GAC TTC GCC      824
```

```
Asp  Arg  Ile  Gly  Val  Ile  Val  Val  His  Ser  Ala  Asn  Pro  Asp  Phe  Ala
          -40                      -35                      -30

AAG  ACC  GTG  CGC  AAG  GTG  CGC  GGC  GTG  CAG  TCG  GCC  GGT  GCC  ACC  CGC        872
Lys  Thr  Val  Arg  Lys  Val  Arg  Gly  Val  Gln  Ser  Ala  Gly  Ala  Thr  Arg
     -25                 -20                      -15

ACC  GCG  CCA  CTG  CCC  TCG  GCC  GCC  ACC  ACC  GAC  ACG  GGC  GCG  CCG  CAG        920
Thr  Ala  Pro  Leu  Pro  Ser  Ala  Ala  Thr  Thr  Asp  Thr  Gly  Ala  Pro  Gln
-10                      -5                       1                    5

GTG  CTC  GGC  GGC  GAG  GAC  CTG  GCC  GCC  GCC  AAG  GCC  GCC  TCC  GCG  AAG        968
Val  Leu  Gly  Gly  Glu  Asp  Leu  Ala  Ala  Ala  Lys  Ala  Ala  Ser  Ala  Lys
               10                      15                      20

GCC  GAG  GGC  CAG  GAC  CCG  CTG  GAG  TCG  CTC  CAG  TGG  GAC  CTG  CCC  GCC       1016
Ala  Glu  Gly  Gln  Asp  Pro  Leu  Glu  Ser  Leu  Gln  Trp  Asp  Leu  Pro  Ala
               25                      30                      35

ATC  AAG  GCG  GAC  AAG  GCG  CAC  GAG  AAG  TCG  CTG  GGC  AGC  AGG  AAG  GTG       1064
Ile  Lys  Ala  Asp  Lys  Ala  His  Glu  Lys  Ser  Leu  Gly  Ser  Arg  Lys  Val
          40                      45                      50

ACC  GTC  GCC  GTC  ATC  GAC  ACC  GGC  GTC  GAC  GAC  ACC  CAC  CCG  GAC  ATC       1112
Thr  Val  Ala  Val  Ile  Asp  Thr  Gly  Val  Asp  Asp  Thr  His  Pro  Asp  Ile
55                       60                      65                       70

GCC  CCG  AAC  TTC  GAC  CGG  CAG  GCG  TCC  GTC  AAC  TGT  GTG  GCG  GGC  AAG       1160
Ala  Pro  Asn  Phe  Asp  Arg  Gln  Ala  Ser  Val  Asn  Cys  Val  Ala  Gly  Lys
                    75                      80                      85

CCG  GAC  ACC  GCC  GAC  GGG  GCC  TGG  CGG  CCG  AGC  GCG  GCG  GAG  AGC  CCG       1208
Pro  Asp  Thr  Ala  Asp  Gly  Ala  Trp  Arg  Pro  Ser  Ala  Ala  Glu  Ser  Pro
               90                      95                      100

CAC  GGC  ACC  CAC  GTG  GCC  GGG  GAG  ATA  GCC  GCC  GCC  AAG  AAC  GGC  GTC       1256
His  Gly  Thr  His  Val  Ala  Gly  Glu  Ile  Ala  Ala  Ala  Lys  Asn  Gly  Val
               105                     110                     115

GGC  ATG  ACC  GGC  GTG  GCA  CCC  GGG  GTG  AAG  GTG  GCC  GGC  ATC  AAG  GTC       1304
Gly  Met  Thr  Gly  Val  Ala  Pro  Gly  Val  Lys  Val  Ala  Gly  Ile  Lys  Val
120                      125                     130

TCC  AAC  CCC  GAC  GGC  TTC  TTC  TAC  ACC  GAG  GCC  GTG  GTC  TGC  GGC  TTC       1352
Ser  Asn  Pro  Asp  Gly  Phe  Phe  Tyr  Thr  Glu  Ala  Val  Val  Cys  Gly  Phe
135                      140                     145                     150

ATG  TGG  GCG  GCC  GAG  CAC  GGC  GTC  GAC  GTG  ACC  AAC  AAC  AGC  TAT  TAC       1400
Met  Trp  Ala  Ala  Glu  His  Gly  Val  Asp  Val  Thr  Asn  Asn  Ser  Tyr  Tyr
               155                     160                     165

ACC  GAC  CCG  TGG  TAC  TTC  AAC  TGC  AAG  GAC  GAC  CCC  GAC  CAG  AAG  GCG       1448
Thr  Asp  Pro  Trp  Tyr  Phe  Asn  Cys  Lys  Asp  Asp  Pro  Asp  Gln  Lys  Ala
               170                     175                     180

CTC  GTC  GAG  GCC  GTC  TCG  CGG  GCC  TCC  CGG  TAC  GCG  GAG  AAG  AAG  GGC       1496
Leu  Val  Glu  Ala  Val  Ser  Arg  Ala  Ser  Arg  Tyr  Ala  Glu  Lys  Lys  Gly
               185                     190                     195

GCG  GTC  AAC  GTC  GCC  GCG  GCC  GGC  AAC  GAG  AAC  TAC  GAC  CTC  ACC  TCC       1544
Ala  Val  Asn  Val  Ala  Ala  Ala  Gly  Asn  Glu  Asn  Tyr  Asp  Leu  Thr  Ser
200                      205                     210

GAC  GAG  ATC  ACC  GAC  CCG  TCC  TCG  CCC  AAC  GAC  ACC  ACG  CCC  GGC  GAC       1592
Asp  Glu  Ile  Thr  Asp  Pro  Ser  Ser  Pro  Asn  Asp  Thr  Thr  Pro  Gly  Asp
215                      220                     225                     230

CGG  ACC  GTC  GAC  CCG  TCG  AAG  TGC  CTG  GAC  ATC  CCG  ACC  CAG  CTG  CCG       1640
Arg  Thr  Val  Asp  Pro  Ser  Lys  Cys  Leu  Asp  Ile  Pro  Thr  Gln  Leu  Pro
               235                     240                     245

GGT  GTC  GTG  ACG  GTC  GCG  GCG  ACC  GGT  GCG  AAG  GGC  CTC  AAG  TCG  TCC       1688
Gly  Val  Val  Thr  Val  Ala  Ala  Thr  Gly  Ala  Lys  Gly  Leu  Lys  Ser  Ser
               250                     255                     260

TTC  TCC  AAC  CAC  GGG  CTG  GGC  GTC  ATC  GAC  ATC  GCC  GCG  CCC  GGC  GGC       1736
Phe  Ser  Asn  His  Gly  Leu  Gly  Val  Ile  Asp  Ile  Ala  Ala  Pro  Gly  Gly
               265                     270                     275

GAC  TCG  ACG  GCC  TAC  CAG  ACC  CCG  GAG  CCG  CCC  GCC  ACG  AGC  GGC  CTG       1784
```

|     |     |     |     |     |     |     |     |     |     |     |     |     |     | |
|---|---|---|---|---|---|---|---|---|---|---|---|---|---|---|
| Asp | Ser | Thr | Ala | Tyr | Gln | Thr | Pro | Glu | Pro | Pro | Ala | Thr | Ser | Gly Leu |
|     | 280 |     |     |     | 285 |     |     |     |     |     | 290 |     |     |         |

```
ATC CTG GGC ACG CTG CCC GGC GGC AAG TGG GGC TAC ATG GCC GGT ACG        1832
Ile Leu Gly Thr Leu Pro Gly Gly Lys Trp Gly Tyr Met Ala Gly Thr
295             300                 305                 310

TCC ATG GCC TCC CCG CAC GTC GCG GGC GTC GCC GCC CTC ATC AAG TCG        1880
Ser Met Ala Ser Pro His Val Ala Gly Val Ala Ala Leu Ile Lys Ser
                315                 320                 325

ACG CAC CCG CAC GCC TCC CCC GCC ATG GTG AAG GCG CTG CTG TAC GCC        1928
Thr His Pro His Ala Ser Pro Ala Met Val Lys Ala Leu Leu Tyr Ala
            330                 335                 340

GAG GCC GAC GCC ACG GCG TGC ACC AAG CCG TAC GAC ATC GAC GGC GAC        1976
Glu Ala Asp Ala Thr Ala Cys Thr Lys Pro Tyr Asp Ile Asp Gly Asp
        345                 350                 355

GGC AAG GTC GAC GCG GTG TGC GAG GGC CCG AAG AAC CGC AAC GGC TTC        2024
Gly Lys Val Asp Ala Val Cys Glu Gly Pro Lys Asn Arg Asn Gly Phe
    360                 365                 370

TAC GGC TGG GGC ATG GCC GAC GCG CTG GAC GCG GTG ACC TGG TAGCCGGTAC    2076
Tyr Gly Trp Gly Met Ala Asp Ala Leu Asp Ala Val Thr Trp
375             380                 385

GCGTACCCGT GCGTGAGGCG GGGGCGGCGG TCCGGTTCCC GTCCGGTCCG CCGCCCCCGT     2136

CGTCGTCGTC GTACGACAGT ATCTTCGCCA TGGACACTTA CGAGGATCC                 2185
```

( 2 ) INFORMATION FOR SEQ ID NO:4:

( i ) SEQUENCE CHARACTERISTICS:
        ( A ) LENGTH: 512 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Thr Ala Pro Leu Ser Arg His Arg Arg Ala Leu Ala Ile Pro Ala
-124            -120            -115                    -110

Gly Leu Ala Val Ala Ala Ser Leu Ala Phe Leu Pro Gly Thr Pro Ala
            -105            -100                -95

Ala Ala Thr Pro Ala Ala Glu Ala Ala Pro Ser Thr Ala Ala Asp Ala
        -90             -85                 -80

Thr Ser Leu Ser Tyr Val Val Asn Val Ala Ser Gly His Arg Pro Ser
    -75             -70                 -65

Ala Thr Val Arg Arg Ala Ile Ala Lys Ala Gly Gly Thr Ile Val Thr
-60             -55                 -50                     -45

Ser Tyr Asp Arg Ile Gly Val Ile Val Val His Ser Ala Asn Pro Asp
                -40             -35                     -30

Phe Ala Lys Thr Val Arg Lys Val Arg Gly Val Gln Ser Ala Gly Ala
            -25             -20                 -15

Thr Arg Thr Ala Pro Leu Pro Ser Ala Ala Thr Thr Asp Thr Gly Ala
        -10              -5                  1

Pro Gln Val Leu Gly Gly Glu Asp Leu Ala Ala Lys Ala Ala Ser
 5              10                  15                      20

Ala Lys Ala Glu Gly Gln Asp Pro Leu Glu Ser Leu Gln Trp Asp Leu
                25                  30                  35

Pro Ala Ile Lys Ala Asp Lys Ala His Glu Lys Ser Leu Gly Ser Arg
            40                  45                  50

Lys Val Thr Val Ala Val Ile Asp Thr Gly Val Asp Asp Thr His Pro
        55                  60                  65

Asp Ile Ala Pro Asn Phe Asp Arg Gln Ala Ser Val Asn Cys Val Ala
```

|     | 70  |     |     |     | 75  |     |     |     | 80  |     |     |     |     |     |
|-----|-----|-----|-----|-----|-----|-----|-----|-----|-----|-----|-----|-----|-----|-----|
| Gly | Lys | Pro | Asp | Thr | Ala | Asp | Gly | Ala | Trp | Arg | Pro | Ser | Ala | Ala | Glu |
| 85  |     |     |     |     | 90  |     |     |     | 95  |     |     |     |     |     | 100 |
| Ser | Pro | His | Gly | Thr | His | Val | Ala | Gly | Glu | Ile | Ala | Ala | Ala | Lys | Asn |
|     |     |     |     | 105 |     |     |     |     | 110 |     |     |     |     | 115 |     |
| Gly | Val | Gly | Met | Thr | Gly | Val | Ala | Pro | Gly | Val | Lys | Val | Ala | Gly | Ile |
|     |     |     | 120 |     |     |     |     | 125 |     |     |     |     | 130 |     |     |
| Lys | Val | Ser | Asn | Pro | Asp | Gly | Phe | Phe | Tyr | Thr | Glu | Ala | Val | Val | Cys |
|     |     | 135 |     |     |     |     | 140 |     |     |     |     | 145 |     |     |     |
| Gly | Phe | Met | Trp | Ala | Ala | Glu | His | Gly | Val | Asp | Val | Thr | Asn | Asn | Ser |
|     | 150 |     |     |     |     | 155 |     |     |     |     | 160 |     |     |     |     |
| Tyr | Tyr | Thr | Asp | Pro | Trp | Tyr | Phe | Asn | Cys | Lys | Asp | Asp | Pro | Asp | Gln |
| 165 |     |     |     |     | 170 |     |     |     |     | 175 |     |     |     |     | 180 |
| Lys | Ala | Leu | Val | Glu | Ala | Val | Ser | Arg | Ala | Ser | Arg | Tyr | Ala | Glu | Lys |
|     |     |     |     | 185 |     |     |     |     | 190 |     |     |     |     | 195 |     |
| Lys | Gly | Ala | Val | Asn | Val | Ala | Ala | Gly | Asn | Glu | Asn | Tyr | Asp | Leu |
|     |     |     | 200 |     |     |     |     | 205 |     |     |     | 210 |     |     |
| Thr | Ser | Asp | Glu | Ile | Thr | Asp | Pro | Ser | Ser | Pro | Asn | Asp | Thr | Thr | Pro |
|     |     | 215 |     |     |     |     | 220 |     |     |     |     | 225 |     |     |     |
| Gly | Asp | Arg | Thr | Val | Asp | Pro | Ser | Lys | Cys | Leu | Asp | Ile | Pro | Thr | Gln |
|     | 230 |     |     |     |     | 235 |     |     |     |     | 240 |     |     |     |     |
| Leu | Pro | Gly | Val | Val | Thr | Val | Ala | Ala | Thr | Gly | Ala | Lys | Gly | Leu | Lys |
| 245 |     |     |     |     | 250 |     |     |     |     | 255 |     |     |     |     | 260 |
| Ser | Ser | Phe | Ser | Asn | His | Gly | Leu | Gly | Val | Ile | Asp | Ile | Ala | Ala | Pro |
|     |     |     |     | 265 |     |     |     |     | 270 |     |     |     |     | 275 |     |
| Gly | Gly | Asp | Ser | Thr | Ala | Tyr | Gln | Thr | Pro | Glu | Pro | Ala | Thr | Ser |
|     |     |     | 280 |     |     |     |     | 285 |     |     |     |     | 290 |     |
| Gly | Leu | Ile | Leu | Gly | Thr | Leu | Pro | Gly | Gly | Lys | Trp | Gly | Tyr | Met | Ala |
|     |     | 295 |     |     |     |     | 300 |     |     |     |     | 305 |     |     |     |
| Gly | Thr | Ser | Met | Ala | Ser | Pro | His | Val | Ala | Gly | Val | Ala | Ala | Leu | Ile |
|     |     | 310 |     |     |     |     | 315 |     |     |     |     | 320 |     |     |     |
| Lys | Ser | Thr | His | Pro | His | Ala | Ser | Pro | Ala | Met | Val | Lys | Ala | Leu | Leu |
| 325 |     |     |     |     | 330 |     |     |     |     | 335 |     |     |     |     | 340 |
| Tyr | Ala | Glu | Ala | Asp | Ala | Thr | Ala | Cys | Thr | Lys | Pro | Tyr | Asp | Ile | Asp |
|     |     |     |     | 345 |     |     |     |     | 350 |     |     |     |     | 355 |     |
| Gly | Asp | Gly | Lys | Val | Asp | Ala | Val | Cys | Glu | Gly | Pro | Lys | Asn | Arg | Asn |
|     |     |     | 360 |     |     |     |     | 365 |     |     |     |     | 370 |     |     |
| Gly | Phe | Tyr | Gly | Trp | Gly | Met | Ala | Asp | Ala | Leu | Asp | Ala | Val | Thr | Trp |
|     |     | 375 |     |     |     |     | 380 |     |     |     |     | 385 |     |     |     |

(2) INFORMATION FOR SEQ ID NO:5:

(i) SEQUENCE CHARACTERISTICS:
        (A) LENGTH: 1777 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 190..1731

(ix) FEATURE:
        (A) NAME/KEY: misc_feature
        (B) LOCATION: 190..192
        (D) OTHER INFORMATION: /note="Met at position 1 represents fMet"

(xi) SEQUENCE DESCRIPTION: SEQ ID NO:5:

| | | | | | | | | | | | | | | | | |
|---|---|---|---|---|---|---|---|---|---|---|---|---|---|---|---|---|
| GGTACCGGCG | GCCAAGACCG | TGTGCTCCTG | ACCGCGGACG | CCACCACAGG | TCGGCAGAAG | | | | | | | | | | | 60 |
| CAGCAGATCG | ACAGAAGTAG | CAGGTCAGAG | CGTTATCCAC | AGGCGTCGGC | GGGTGCTGCC | | | | | | | | | | | 120 |
| CCCGCCACCT | ACCATGGCAG | GAACGCCATC | CGCCGCACGG | CGCGGACGGC | TTGCCAGGGG | | | | | | | | | | | 180 |

```
GGAGAGGAC ATG GCG CGT CTC GTC CGG TGG ACG GCT CTG ACG GCC GCC                228
          Met Ala Arg Leu Val Arg Trp Thr Ala Leu Thr Ala Ala
           1               5                      10

GCC GCA CTG CTG ACG GCG GGC TGC AGC GGC GGC TCG TCC GAC GAG GAC              276
Ala Ala Leu Leu Thr Ala Gly Cys Ser Gly Gly Ser Ser Asp Glu Asp
         15                  20                  25

AAG GAC GAC GGG GGC AGG AGC AGC GCG GGA CCT TCG GCG GCG GCA CCC              324
Lys Asp Asp Gly Gly Arg Ser Ser Ala Gly Pro Ser Ala Ala Ala Pro
 30              35                  40                      45

TCC GGG GTG CCG GAG GCA CTG GCG TCC CAG ACG CTG GAC TGG GCC CGA              372
Ser Gly Val Pro Glu Ala Leu Ala Ser Gln Thr Leu Asp Trp Ala Arg
             50                  55                  60

TGC GAG GGC AGC GAC GAT GCC CCG GCG CCG GAC GGC GAC TGG CGG TGC              420
Cys Glu Gly Ser Asp Asp Ala Pro Ala Pro Asp Gly Asp Trp Arg Cys
             65                  70                  75

GCC ACG CTG AAG GCA CCG CTG GAC TGG TCC GAC CCC GAC GGC GAG ACG              468
Ala Thr Leu Lys Ala Pro Leu Asp Trp Ser Asp Pro Asp Gly Glu Thr
         80                  85                  90

ATC GAT CTC GCG CTG ATC CGG TCC CGG GCG AGC GGG GAC GAC CGC ATC              516
Ile Asp Leu Ala Leu Ile Arg Ser Arg Ala Ser Gly Asp Asp Arg Ile
         95                 100                 105

GGC TCC CTG CTG TTC AAC TTC GGC GGC CCG GGC GCC TCC GGC GTC TCC              564
Gly Ser Leu Leu Phe Asn Phe Gly Gly Pro Gly Ala Ser Gly Val Ser
110             115                 120                     125

ACG ATG CCG TCC TAC GCC GAC ACC GTC TCC TCC CTG CAC GAG CGG TAC              612
Thr Met Pro Ser Tyr Ala Asp Thr Val Ser Ser Leu His Glu Arg Tyr
             130                 135                 140

GAC CTG GTG AGC TGG GAC CCG CGC GGG GTG GCC GCC AGC GAG GGC GTC              660
Asp Leu Val Ser Trp Asp Pro Arg Gly Val Ala Ala Ser Glu Gly Val
             145                 150                 155

CGC TGC CGC ACC GAC GAG GCG ATC GAG GCC GCC GAG TCG GTG GAC TCC              708
Arg Cys Arg Thr Asp Glu Ala Ile Glu Ala Ala Glu Ser Val Asp Ser
             160                 165                 170

ACG CCG GAC TCC CCG GCC GAG GAG CAG GCC TAC CTG AAG GAC GCC GCC              756
Thr Pro Asp Ser Pro Ala Glu Glu Gln Ala Tyr Leu Lys Asp Ala Ala
175                 180                 185

GAC TTC GGC AGG GGC TGC GAG AAG GCC GCC GGC AAG CTC ATG GAA CAC              804
Asp Phe Gly Arg Gly Cys Glu Lys Ala Ala Gly Lys Leu Met Glu His
190                 195                 200                 205

GTC TCG ACC ACG GAC ACG GCC CGC GAC ATG GAC CTG ATG CGG CAC GTC              852
Val Ser Thr Thr Asp Thr Ala Arg Asp Met Asp Leu Met Arg His Val
             210                 215                 220

CTG GGC GAC GAG AGG ATG CAC TAC TTC GGC ATC TCC TAC GGC ACC GAA              900
Leu Gly Asp Glu Arg Met His Tyr Phe Gly Ile Ser Tyr Gly Thr Glu
             225                 230                 235

CTC GGC GGC GTC TAC GCC CAT CTG TTC CCC GAG CAC GTG GGC CGC GTG              948
Leu Gly Gly Val Tyr Ala His Leu Phe Pro Glu His Val Gly Arg Val
             240                 245                 250

ATC CTC GAC GCG GTG GTG GAC CCG GGC GCC GAC ACG ATG GGC CAC GCC              996
Ile Leu Asp Ala Val Val Asp Pro Gly Ala Asp Thr Met Gly His Ala
255                 260                 265

GAG AAC CAG GCC AGG GGT TTC CAG CGC GCG CTG GAC GAC TAC CTG GAG              1044
Glu Asn Gln Ala Arg Gly Phe Gln Arg Ala Leu Asp Asp Tyr Leu Glu
270                 275                 280                 285

TCG ACC GGC CAG GAA CCC GAA CAG GGG TCG CGG AAG ATC GCC GGC CTG              1092
Ser Thr Gly Gln Glu Pro Glu Gln Gly Ser Arg Lys Ile Ala Gly Leu
```

|  |  |  | 290 |  |  |  |  | 295 |  |  |  |  | 300 |  |  |
|---|---|---|---|---|---|---|---|---|---|---|---|---|---|---|---|
| CTG | GAG | CGG | CTG | GAC | GCC | GAG | CCA | CTG | CCC | ACG | TCC | TCG | CCG | GGG | CGG | 1140 |
| Leu | Glu | Arg | Leu | Asp | Ala | Glu | Pro | Leu | Pro | Thr | Ser | Ser | Pro | Gly | Arg |
|  |  | 305 |  |  |  |  |  | 310 |  |  |  |  | 315 |  |  |
| GAG | CTG | ACG | CAG | ACC | CTC | GCG | TTC | ACC | GGC | ATC | GTG | CTG | CCG | CTG | TAC | 1188 |
| Glu | Leu | Thr | Gln | Thr | Leu | Ala | Phe | Thr | Gly | Ile | Val | Leu | Pro | Leu | Tyr |
|  |  | 320 |  |  |  |  | 325 |  |  |  |  | 330 |  |  |  |
| AGC | GAG | AGC | GGC | TGG | CCG | GCC | CTG | ACC | AGT | GCG | CTG | AAG | GCG | GCC | GAG | 1236 |
| Ser | Glu | Ser | Gly | Trp | Pro | Ala | Leu | Thr | Ser | Ala | Leu | Lys | Ala | Ala | Glu |
|  | 335 |  |  |  | 340 |  |  |  |  | 345 |  |  |  |  |  |
| GAG | GGC | GAC | GGC | TCG | GAG | TTG | CTG | GCC | CTC | GCC | GAC | GGC | TAC | AAC | GAG | 1284 |
| Glu | Gly | Asp | Gly | Ser | Glu | Leu | Leu | Ala | Leu | Ala | Asp | Gly | Tyr | Asn | Glu |
| 350 |  |  |  |  | 355 |  |  |  | 360 |  |  |  |  | 365 |  |
| CGT | GAT | CCC | TCG | GGG | CGC | TAC | GGC | ACG | ACG | ACC | CAC | TCG | CAA | AGG | GTC | 1332 |
| Arg | Asp | Pro | Ser | Gly | Arg | Tyr | Gly | Thr | Thr | Thr | His | Ser | Gln | Arg | Val |
|  |  |  |  | 370 |  |  |  |  | 375 |  |  |  |  | 380 |  |
| ATA | TCG | TGC | CTG | GAC | GAC | AAG | CAG | AGG | CCG | ACC | GTG | GAG | GAG | ACG | AAG | 1380 |
| Ile | Ser | Cys | Leu | Asp | Asp | Lys | Gln | Arg | Pro | Thr | Val | Glu | Glu | Thr | Lys |
|  |  |  | 385 |  |  |  |  | 390 |  |  |  |  | 395 |  |  |
| AAG | CTG | CTG | CCG | AGG | TTC | GAG | AAG | GTC | TCT | CCC | GTC | TTC | GGC | GCC | TTC | 1428 |
| Lys | Leu | Leu | Pro | Arg | Phe | Glu | Lys | Val | Ser | Pro | Val | Phe | Gly | Ala | Phe |
|  |  | 400 |  |  |  |  | 405 |  |  |  |  | 410 |  |  |  |
| CTC | GGC | TGG | GAC | ACG | GCC | GGG | TGG | TGC | CAC | GAC | TGG | CCG | GTG | GCC | GGT | 1476 |
| Leu | Gly | Trp | Asp | Thr | Ala | Gly | Trp | Cys | His | Asp | Trp | Pro | Val | Ala | Gly |
|  | 415 |  |  |  |  | 420 |  |  |  |  | 425 |  |  |  |  |
| CAG | CAC | GAG | ACC | GCG | GAG | GTG | AGC | GCG | CCC | GAC | GCG | GCC | CCG | GTC | CTG | 1524 |
| Gln | His | Glu | Thr | Ala | Glu | Val | Ser | Ala | Pro | Asp | Ala | Ala | Pro | Val | Leu |
| 430 |  |  |  |  | 435 |  |  |  | 440 |  |  |  |  | 445 |  |
| GTG | GTC | GGC | AAC | ACG | GGC | GAC | CCG | GCC | ACG | CCC | TAC | GAG | GGC | GCC | CGC | 1572 |
| Val | Val | Gly | Asn | Thr | Gly | Asp | Pro | Ala | Thr | Pro | Tyr | Glu | Gly | Ala | Arg |
|  |  |  | 450 |  |  |  |  | 455 |  |  |  |  | 460 |  |  |
| AGG | ATG | GCG | GAC | GAG | CTG | GGC | AAG | GAC | GTC | GGC | GTG | GTG | CTG | ACC | TGG | 1620 |
| Arg | Met | Ala | Asp | Glu | Leu | Gly | Lys | Asp | Val | Gly | Val | Val | Leu | Thr | Trp |
|  |  | 465 |  |  |  |  | 470 |  |  |  |  | 475 |  |  |  |
| CAG | GGC | GAG | GGA | CAC | GGT | GCC | TAC | GGG | AAC | GGA | AGC | GAC | TGT | GTC | GAC | 1668 |
| Gln | Gly | Glu | Gly | His | Gly | Ala | Tyr | Gly | Asn | Gly | Ser | Asp | Cys | Val | Asp |
|  | 480 |  |  |  | 485 |  |  |  |  | 490 |  |  |  |  |  |
| TCC | GCG | GTG | GAC | GCC | TAC | CTG | TTG | AAG | GGG | ACG | GTG | CCG | AAG | GAC | GGC | 1716 |
| Ser | Ala | Val | Asp | Ala | Tyr | Leu | Leu | Lys | Gly | Thr | Val | Pro | Lys | Asp | Gly |
| 495 |  |  |  |  | 500 |  |  |  | 505 |  |  |  |  |  |  |
| AAG | GTC | TGC | TCA | TGACGGCGGC | GGGGGCTTCG | GGCACCTGCG | GTGCGCGAAA |  |  |  |  |  |  |  |  | 1768 |
| Lys | Val | Cys | Ser |
| 510 |

CCCCGCCG                                                                                                                     1777

( 2 ) INFORMATION FOR SEQ ID NO:6:

( i ) SEQUENCE CHARACTERISTICS:
        ( A ) LENGTH: 513 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Ala | Arg | Leu | Val | Arg | Trp | Thr | Ala | Leu | Thr | Ala | Ala | Ala | Ala | Leu |
|---|---|---|---|---|---|---|---|---|---|---|---|---|---|---|---|
| 1 |  |  |  | 5 |  |  |  |  | 10 |  |  |  |  | 15 |  |
| Leu | Thr | Ala | Gly | Cys | Ser | Gly | Gly | Ser | Asp | Glu | Asp | Lys | Asp | Asp |
|  |  |  | 20 |  |  |  |  | 25 |  |  |  |  | 30 |  |
| Gly | Gly | Arg | Ser | Ser | Ala | Gly | Pro | Ser | Ala | Ala | Ala | Pro | Ser | Gly | Val |
|  |  |  | 35 |  |  |  |  | 40 |  |  |  |  | 45 |  |  |

Pro Glu Ala Leu Ala Ser Gln Thr Leu Asp Trp Ala Arg Cys Glu Gly
50                    55                      60

Ser Asp Asp Ala Pro Ala Pro Asp Gly Asp Trp Arg Cys Ala Thr Leu
65              70              75                              80

Lys Ala Pro Leu Asp Trp Ser Asp Pro Asp Gly Glu Thr Ile Asp Leu
                85                  90                      95

Ala Leu Ile Arg Ser Arg Ala Ser Gly Asp Asp Arg Ile Gly Ser Leu
            100             105                     110

Leu Phe Asn Phe Gly Gly Pro Gly Ala Ser Gly Val Ser Thr Met Pro
        115                 120                 125

Ser Tyr Ala Asp Thr Val Ser Ser Leu His Glu Arg Tyr Asp Leu Val
    130                 135                 140

Ser Trp Asp Pro Arg Gly Val Ala Ala Ser Glu Gly Val Arg Cys Arg
145                 150                 155                     160

Thr Asp Glu Ala Ile Glu Ala Ala Glu Ser Val Asp Ser Thr Pro Asp
                165                 170                 175

Ser Pro Ala Glu Glu Gln Ala Tyr Leu Lys Asp Ala Ala Asp Phe Gly
            180                 185                 190

Arg Gly Cys Glu Lys Ala Ala Gly Lys Leu Met Glu His Val Ser Thr
        195                 200                 205

Thr Asp Thr Ala Arg Asp Met Asp Leu Met Arg His Val Leu Gly Asp
    210                 215                 220

Glu Arg Met His Tyr Phe Gly Ile Ser Tyr Gly Thr Glu Leu Gly Gly
225                 230                 235                     240

Val Tyr Ala His Leu Phe Pro Glu His Val Gly Arg Val Ile Leu Asp
                245                 250                 255

Ala Val Val Asp Pro Gly Ala Asp Thr Met Gly His Ala Glu Asn Gln
            260                 265                 270

Ala Arg Gly Phe Gln Arg Ala Leu Asp Asp Tyr Leu Glu Ser Thr Gly
        275                 280                 285

Gln Glu Pro Glu Gln Gly Ser Arg Lys Ile Ala Gly Leu Leu Glu Arg
290                 295                 300

Leu Asp Ala Glu Pro Leu Pro Thr Ser Ser Pro Gly Arg Glu Leu Thr
305                 310                 315                     320

Gln Thr Leu Ala Phe Thr Gly Ile Val Leu Pro Leu Tyr Ser Glu Ser
                325                 330                 335

Gly Trp Pro Ala Leu Thr Ser Ala Leu Lys Ala Ala Glu Glu Gly Asp
            340                 345                 350

Gly Ser Glu Leu Leu Ala Leu Ala Asp Gly Tyr Asn Glu Arg Asp Pro
        355                 360                 365

Ser Gly Arg Tyr Gly Thr Thr His Ser Gln Arg Val Ile Ser Cys
    370                 375                 380

Leu Asp Asp Lys Gln Arg Pro Thr Val Glu Glu Thr Lys Lys Leu Leu
385                 390                 395                     400

Pro Arg Phe Glu Lys Val Ser Pro Val Phe Gly Ala Phe Leu Gly Trp
                405                 410                 415

Asp Thr Ala Gly Trp Cys His Asp Trp Pro Val Ala Gly Gln His Glu
            420                 425                 430

Thr Ala Glu Val Ser Ala Pro Asp Ala Ala Pro Val Leu Val Val Gly
        435                 440                 445

Asn Thr Gly Asp Pro Ala Thr Pro Tyr Glu Gly Ala Arg Arg Met Ala
    450                 455                 460

Asp Glu Leu Gly Lys Asp Val Gly Val Val Leu Thr Trp Gln Gly Glu

| | | | | | | | | | | | | | | | |
|---|---|---|---|---|---|---|---|---|---|---|---|---|---|---|---|
|465| | | |470| | | |475| | | |480| | | |
|Gly|His|Gly|Ala|Tyr|Gly|Asn|Gly|Ser|Asp|Cys|Val|Asp|Ser|Ala|Val|
| | | | |485| | | |490| | | |495| | | |
|Asp|Ala|Tyr|Leu|Leu|Lys|Gly|Thr|Val|Pro|Lys|Asp|Gly|Lys|Val|Cys|
| | | |500| | | |505| | | |510| | | | |
|Ser| | | | | | | | | | | | | | | |

(2) INFORMATION FOR SEQ ID NO:7:

(i) SEQUENCE CHARACTERISTICS:
        (A) LENGTH: 1820 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 104..1720

(ix) FEATURE:
        (A) NAME/KEY: sig_peptide
        (B) LOCATION: 104..244

(ix) FEATURE:
        (A) NAME/KEY: mat_peptide
        (B) LOCATION: 245..1720

(xi) SEQUENCE DESCRIPTION: SEQ ID NO:7:

```
CCCGGGCCCG CGTCGGAGTC ATGACCGGTT GACGCCGTAA CACGTACGGG GCACGCGCAC        60

CACGCACCGC AACTGCTTCG TCGCGGAGAG TTACGCTCGC TGA ATG GAC ACA AGG        115
                                            Met Asp Thr Arg
                                            -47         -45

CGC ACT CAC CGC AGG ACC CGC ACC GGC GGC ACC CGT TTC CGG GCC ACG        163
Arg Thr His Arg Arg Thr Arg Thr Gly Gly Thr Arg Phe Arg Ala Thr
            -40             -35             -30

CTG CTC ACC GCC GCG CTG CTC GCC ACC GCC TGC TCG GCC GGG GGC GCG        211
Leu Leu Thr Ala Ala Leu Leu Ala Thr Ala Cys Ser Ala Gly Gly Ala
        -25             -20             -15

TCG ACG TCC GCC GGA TCC CCC GCG GCC AAG GCG GCC GGC GCG ACG GAG        259
Ser Thr Ser Ala Gly Ser Pro Ala Ala Lys Ala Ala Gly Ala Thr Glu
    -10              -5              1               5

GCG GCC ACG GCG ACC CTG ACC CCC CTG CCG AAG GCC ACG CCC GCC GAG        307
Ala Ala Thr Ala Thr Leu Thr Pro Leu Pro Lys Ala Thr Pro Ala Glu
                10              15              20

CTG TCC CCG TAC TAC GAG CAG AAG CTC GGC TGG CGC GAC TGC GGC GTC        355
Leu Ser Pro Tyr Tyr Glu Gln Lys Leu Gly Trp Arg Asp Cys Gly Val
            25              30              35

CCG GGC TTC CAG TGC GCC ACC ATG AAG GCC CCG CTC GAC TAC GCC AAG        403
Pro Gly Phe Gln Cys Ala Thr Met Lys Ala Pro Leu Asp Tyr Ala Lys
        40              45              50

CCC GCC GAC GGC GAC GTC CGG CTC GCG GTG GCC CGC AAG AAG GCC ACG        451
Pro Ala Asp Gly Asp Val Arg Leu Ala Val Ala Arg Lys Lys Ala Thr
    55              60              65

GGG CCG GGC AAG CGC CTC GGC TCG CTG CTG GTC AAC CCG GGC GGA CCG        499
Gly Pro Gly Lys Arg Leu Gly Ser Leu Leu Val Asn Pro Gly Gly Pro
70              75              80              85

GGC GGC TCG GCG ATC GGC TAC CTC CAG CAG TAC GCG GGC ATC GGC TAC        547
Gly Gly Ser Ala Ile Gly Tyr Leu Gln Gln Tyr Ala Gly Ile Gly Tyr
            90              95              100

CCG GCG AAG GTC CGC GCC CAG TAC GAC ATG GTG GCG GTC GAC CCC CGG        595
Pro Ala Lys Val Arg Ala Gln Tyr Asp Met Val Ala Val Asp Pro Arg
        105             110             115

GGC GTG GCC CGC AGT GAA CCC GTC GAG TGC CTG GAC GGG CGC GAG ATG        643
```

-continued

```
Gly Val Ala Arg Ser Glu Pro Val Glu Cys Leu Asp Gly Arg Glu Met
        120                 125                 130

GAC GCG TAC ACG CGC ACC GAC GTC ACC CCG GAC GAC GCG GGC GAG ACG    691
Asp Ala Tyr Thr Arg Thr Asp Val Thr Pro Asp Asp Ala Gly Glu Thr
135                 140                 145

GAC GAG CTG GTC GAC GCC TAC AAG GAG TTC GCC GAG GGC TGC GGG GCG    739
Asp Glu Leu Val Asp Ala Tyr Lys Glu Phe Ala Glu Gly Cys Gly Ala
150                 155                 160                 165

GAC GCG CCG AAG CTG CTG CGC CAC GTC TCC ACG GTC GAG GCG GCA CGC    787
Asp Ala Pro Lys Leu Leu Arg His Val Ser Thr Val Glu Ala Ala Arg
                170                 175                 180

GAC ATG GAC GTC CTG CGC GCG GTG CTG GGC GAC GAG AAG CTG ACC TAC    835
Asp Met Asp Val Leu Arg Ala Val Leu Gly Asp Glu Lys Leu Thr Tyr
            185                 190                 195

GTG GGA GCG TCG TAC GGC ACC TTC CTG GGC GCG ACC TAC GCC GGT CTG    883
Val Gly Ala Ser Tyr Gly Thr Phe Leu Gly Ala Thr Tyr Ala Gly Leu
        200                 205                 210

TTC CCC GAC CGG ACG GGC CGC CTG GTC CTG GAC GGC GCG ATG GAC CCC    931
Phe Pro Asp Arg Thr Gly Arg Leu Val Leu Asp Gly Ala Met Asp Pro
    215                 220                 225

TCG CTG CCC GCC CGC CGC CTG AAC CTG GAG CAG ACG GAG GGC TTC GAG    979
Ser Leu Pro Ala Arg Arg Leu Asn Leu Glu Gln Thr Glu Gly Phe Glu
230                 235                 240                 245

ACG GCG TTC CAG TCC TTC GCG AAG GAC TGC GTG AAG CAG CCG GAC TGC   1027
Thr Ala Phe Gln Ser Phe Ala Lys Asp Cys Val Lys Gln Pro Asp Cys
                250                 255                 260

CCC CTC GGC GAC AAG GAC ACC ACC CCC GAC CAG GTC GGC AAG AAC CTC   1075
Pro Leu Gly Asp Lys Asp Thr Thr Pro Asp Gln Val Gly Lys Asn Leu
            265                 270                 275

AAG TCC TTC TTC GAC GAC CTG GAC GCG AAG CCC CTG CCC GCC GGC GAC   1123
Lys Ser Phe Phe Asp Asp Leu Asp Ala Lys Pro Leu Pro Ala Gly Asp
        280                 285                 290

GCC GAC GGC CGC AAG CTC ACC GAA TCC CTC GCC ACC ACC GGC GTG ATC   1171
Ala Asp Gly Arg Lys Leu Thr Glu Ser Leu Ala Thr Thr Gly Val Ile
    295                 300                 305

GCC GCG ATG TAC GAC GAG GGC GCC TGG CAG CAG CTG CGC GAG TCC CTC   1219
Ala Ala Met Tyr Asp Glu Gly Ala Trp Gln Gln Leu Arg Glu Ser Leu
310                 315                 320                 325

ACC TCG GCG ATC AAG GAG AAG GAC GGT GCG GGC CTG CTG ATC CTC TCC   1267
Thr Ser Ala Ile Lys Glu Lys Asp Gly Ala Gly Leu Leu Ile Leu Ser
                330                 335                 340

GAC AGC TAC TAC GAG CGC GAG GCC GAC GGC GGC TAC AGC AAC CTG ATG   1315
Asp Ser Tyr Tyr Glu Arg Glu Ala Asp Gly Gly Tyr Ser Asn Leu Met
            345                 350                 355

TTC GCC AAC GCC GCC GTG AAC TGC CTC GAC CTC CCC GCC GCC TTC TCC   1363
Phe Ala Asn Ala Ala Val Asn Cys Leu Asp Leu Pro Ala Ala Phe Ser
        360                 365                 370

TCC CCG GAC GAG GTG CGC GAC GCC CTC CCC GAC TTC GAG AAG GCG TCC   1411
Ser Pro Asp Glu Val Arg Asp Ala Leu Pro Asp Phe Glu Lys Ala Ser
    375                 380                 385

CCG GTC TTC GGC GAG GGC CTC GCC TGG TCC TCC CTG AAC TGC GCG TAC   1459
Pro Val Phe Gly Glu Gly Leu Ala Trp Ser Ser Leu Asn Cys Ala Tyr
390                 395                 400                 405

TGG CCG GTG AAG CCC ACG GGG GAG CCG CAC CGC ATC GAG GCG GCC GGC   1507
Trp Pro Val Lys Pro Thr Gly Glu Pro His Arg Ile Glu Ala Ala Gly
                410                 415                 420

GCC ACC CCG ATC GTC GTG GTC GGC ACC ACC CGC GAC CCG GCC ACC CCC   1555
Ala Thr Pro Ile Val Val Val Gly Thr Thr Arg Asp Pro Ala Thr Pro
            425                 430                 435

TAC CGC TGG GCC GAG GCC CTC TCC GAC CAG CTC ACC TCC GGC CAC CTC   1603
```

|   |   |   |   |   |   |   |   |   |   |   |   |   |   |   |   |   |
|---|---|---|---|---|---|---|---|---|---|---|---|---|---|---|---|---|
| Tyr | Arg | Trp<br>440 | Ala | Glu | Ala | Leu | Ser<br>445 | Asp | Gln | Leu | Thr | Ser<br>450 | Gly | His | Leu |   |
| CTC | ACC | TAC | GAG | GGA | GAC | GGC | CAC | ACC | GCG | TAC | GGC | CGC | GGC | AGC | TCC | 1651 |
| Leu<br>455 | Thr | Tyr | Glu | Gly | Asp | Gly<br>460 | His | Thr | Ala | Tyr | Gly<br>465 | Arg | Gly | Ser | Ser |   |
| TGC | ATC | GAC | TCC | GCG | ATC | AAC | ACG | TAC | CTG | CTG | ACC | GGC | ACC | GCC | CCG | 1699 |
| Cys<br>470 | Ile | Asp | Ser | Ala | Ile<br>475 | Asn | Thr | Tyr | Leu | Leu<br>480 | Thr | Gly | Thr | Ala | Pro<br>485 |   |
| GAG | GAC | GGC | AAG | CGC | TGC | TCG | TAACCCCGC | CTGCCCGCCC | CGGGACCCAC |   |   |   |   |   |   | 1750 |
| Glu | Asp | Gly | Lys | Arg<br>490 | Cys | Ser |   |   |   |   |   |   |   |   |   |   |

GCCTCCGGGG CGGGTTCGGA GCACCCCGGG AAACTGTGTA GACTTGCCGA CGTTGCTGAT 1810

CGCACCATGG 1820

( 2 ) INFORMATION FOR SEQ ID NO:8:

( i ) SEQUENCE CHARACTERISTICS:
( A ) LENGTH: 539 amino acids
( B ) TYPE: amino acid
( D ) TOPOLOGY: linear ( i i ) MOLECULE TYPE: protein ( x i ) SEQUENCE DESCRIPTION: SEQ ID NO:8:

| Met<br>-47 | Asp | Thr<br>-45 | Arg | Arg | Thr | His | Arg<br>-40 | Arg | Thr | Arg | Thr | Gly<br>-35 | Gly | Thr | Arg |
|---|---|---|---|---|---|---|---|---|---|---|---|---|---|---|---|
| Phe | Arg<br>-30 | Ala | Thr | Leu | Leu | Thr<br>-25 | Ala | Ala | Leu | Leu | Ala<br>-20 | Thr | Ala | Cys | Ser |
| Ala<br>-15 | Gly | Gly | Ala | Ser | Thr<br>-10 | Ser | Ala | Gly | Ser | Pro<br>-5 | Ala | Ala | Lys | Ala | Ala<br>1 |
| Gly | Ala | Thr | Glu<br>5 | Ala | Ala | Thr | Ala | Thr<br>10 | Leu | Thr | Pro | Leu | Pro<br>15 | Lys | Ala |
| Thr | Pro | Ala<br>20 | Glu | Leu | Ser | Pro | Tyr<br>25 | Tyr | Glu | Gln | Lys | Leu<br>30 | Gly | Trp | Arg |
| Asp | Cys<br>35 | Gly | Val | Pro | Gly | Phe<br>40 | Gln | Cys | Ala | Thr | Met<br>45 | Lys | Ala | Pro | Leu |
| Asp<br>50 | Tyr | Ala | Lys | Pro | Ala<br>55 | Asp | Gly | Asp | Val | Arg<br>60 | Leu | Ala | Val | Ala | Arg<br>65 |
| Lys | Lys | Ala | Thr | Gly<br>70 | Pro | Gly | Lys | Arg | Leu<br>75 | Gly | Ser | Leu | Leu | Val<br>80 | Asn |
| Pro | Gly | Gly | Pro<br>85 | Gly | Gly | Ser | Ala | Ile<br>90 | Gly | Tyr | Leu | Gln | Gln<br>95 | Tyr | Ala |
| Gly | Ile | Gly<br>100 | Tyr | Pro | Ala | Lys | Val<br>105 | Arg | Ala | Gln | Tyr | Asp<br>110 | Met | Val | Ala |
| Val | Asp<br>115 | Pro | Arg | Gly | Val | Ala<br>120 | Arg | Ser | Glu | Pro | Val<br>125 | Glu | Cys | Leu | Asp |
| Gly<br>130 | Arg | Glu | Met | Asp | Ala<br>135 | Tyr | Thr | Arg | Thr | Asp<br>140 | Val | Thr | Pro | Asp | Asp<br>145 |
| Ala | Gly | Glu | Thr | Asp<br>150 | Glu | Leu | Val | Asp | Ala<br>155 | Tyr | Lys | Glu | Phe | Ala<br>160 | Glu |
| Gly | Cys | Gly | Ala<br>165 | Asp | Ala | Pro | Lys | Leu<br>170 | Leu | Arg | His | Val | Ser<br>175 | Thr | Val |
| Glu | Ala | Ala<br>180 | Arg | Asp | Met | Asp | Val<br>185 | Leu | Arg | Ala | Val | Leu<br>190 | Gly | Asp | Glu |
| Lys | Leu<br>195 | Thr | Tyr | Val | Gly | Ala<br>200 | Ser | Tyr | Gly | Thr | Phe<br>205 | Leu | Gly | Ala | Thr |
| Tyr | Ala | Gly | Leu | Phe | Pro | Asp | Arg | Thr | Gly | Arg | Leu | Val | Leu | Asp | Gly |

```
                        210                           215                           220                           225

Ala    Met    Asp    Pro    Ser    Leu    Pro    Ala    Arg    Arg    Leu    Asn    Leu    Glu    Gln    Thr
                            230                                  235                                  240

Glu    Gly    Phe    Glu    Thr    Ala    Phe    Gln    Ser    Phe    Ala    Lys    Asp    Cys    Val    Lys
                     245                                  250                                  255

Gln    Pro    Asp    Cys    Pro    Leu    Gly    Asp    Lys    Asp    Thr    Thr    Pro    Asp    Gln    Val
              260                                  265                                  270

Gly    Lys    Asn    Leu    Lys    Ser    Phe    Phe    Asp    Asp    Leu    Asp    Ala    Lys    Pro    Leu
       275                                  280                                  285

Pro    Ala    Gly    Asp    Ala    Asp    Gly    Arg    Lys    Leu    Thr    Glu    Ser    Leu    Ala    Thr
290                                  295                                  300                                  305

Thr    Gly    Val    Ile    Ala    Ala    Met    Tyr    Asp    Glu    Gly    Ala    Trp    Gln    Gln    Leu
                            310                                  315                                  320

Arg    Glu    Ser    Leu    Thr    Ser    Ala    Ile    Lys    Glu    Lys    Asp    Gly    Ala    Gly    Leu
                     325                                  330                                  335

Leu    Ile    Leu    Ser    Asp    Ser    Tyr    Tyr    Glu    Arg    Glu    Ala    Asp    Gly    Gly    Tyr
              340                                  345                                  350

Ser    Asn    Leu    Met    Phe    Ala    Asn    Ala    Ala    Val    Asn    Cys    Leu    Asp    Leu    Pro
       355                                  360                                  365

Ala    Ala    Phe    Ser    Ser    Pro    Asp    Glu    Val    Arg    Asp    Ala    Leu    Pro    Asp    Phe
370                                  375                                  380                                  385

Glu    Lys    Ala    Ser    Pro    Val    Phe    Gly    Glu    Gly    Leu    Ala    Trp    Ser    Ser    Leu
                     390                                  395                                  400

Asn    Cys    Ala    Tyr    Trp    Pro    Val    Lys    Pro    Thr    Gly    Glu    Pro    His    Arg    Ile
                     405                                  410                                  415

Glu    Ala    Ala    Gly    Ala    Thr    Pro    Ile    Val    Val    Val    Gly    Thr    Thr    Arg    Asp
              420                                  425                                  430

Pro    Ala    Thr    Pro    Tyr    Arg    Trp    Ala    Glu    Ala    Leu    Ser    Asp    Gln    Leu    Thr
       435                                  440                                  445

Ser    Gly    His    Leu    Leu    Thr    Tyr    Glu    Gly    Asp    Gly    His    Thr    Ala    Tyr    Gly
450                                  455                                  460                                  465

Arg    Gly    Ser    Ser    Cys    Ile    Asp    Ser    Ala    Ile    Asn    Thr    Tyr    Leu    Leu    Thr
                     470                                  475                                  480

Gly    Thr    Ala    Pro    Glu    Asp    Gly    Lys    Arg    Cys    Ser
              485                                  490
```

(2) INFORMATION FOR SEQ ID NO:9:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:9:

```
Gly    Xaa    Ser    Xaa    Gly
 1                            5
```

(2) INFORMATION FOR SEQ ID NO:10:

(i) SEQUENCE CHARACTERISTICS:
        (A) LENGTH: 10 amino acids
        (B) TYPE: amino acid
        (D) TOPOLOGY: linear (ix) FEATURE:
        (A) NAME/KEY: Modified-site
        (B) LOCATION: 8
        (D) OTHER INFORMATION: /note="Xaa at position 8
            represents Gln or Ser"

( x i ) SEQUENCE DESCRIPTION: SEQ ID NO:10:

Asp Gly His Gly His Arg Ser Xaa Asp Ala
1               5                   10

(2) INFORMATION FOR SEQ ID NO:11:

( i ) SEQUENCE CHARACTERISTICS:
     ( A ) LENGTH: 30 amino acids
     ( B ) TYPE: amino acid
     ( D ) TOPOLOGY: linear ( x i ) SEQUENCE DESCRIPTION: SEQ ID NO:11:

Arg Val Asp Leu Val Gly Asn Ser Phe Gly Gly Ala Leu Ser Leu Ala
1               5                   10                  15

Phe Ala Ile Arg Phe Pro His Arg Val Arg Arg Leu Val Leu
            20              25                  30

(2) INFORMATION FOR SEQ ID NO:12:

( i ) SEQUENCE CHARACTERISTICS:
     ( A ) LENGTH: 381 amino acids
     ( B ) TYPE: amino acid
     ( D ) TOPOLOGY: linear ( x i ) SEQUENCE DESCRIPTION: SEQ ID NO:12:

Met Arg Gly Lys Lys Val Trp Ile Ser Leu Leu Phe Ala Leu Ala Leu
1               5                   10                  15

Ile Phe Thr Met Ala Phe Gly Ser Thr Ser Ser Ala Gln Ala Ala Gly
            20              25                  30

Lys Ser Asn Gly Glu Lys Lys Tyr Ile Val Gly Phe Lys Gln Thr Met
            35              40                  45

Ser Thr Met Ser Ala Ala Lys Lys Asp Val Ile Ser Glu Lys Gly
        50              55                  60

Gly Lys Val Gln Lys Gln Phe Lys Tyr Val Asp Ala Ala Ser Ala Thr
65                  70                  75                  80

Leu Asn Glu Lys Ala Val Lys Glu Leu Lys Lys Asp Pro Ser Val Ala
                85              90                  95

Tyr Val Glu Glu Asp His Val Ala His Ala Tyr Ala Gln Ser Val Pro
                100             105                 110

Tyr Gly Val Ser Gln Ile Lys Ala Pro Ala Leu His Ser Gln Gly Tyr
            115             120                 125

Thr Gly Ser Asn Val Lys Val Ala Val Ile Asp Ser Gly Ile Asp Ser
    130                 135                 140

Ser His Pro Asp Leu Lys Val Ala Gly Gly Ala Ser Met Val Pro Ser
145                 150                 155                 160

Glu Thr Asn Pro Phe Gln Asp Asn Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Ala Ser Leu Tyr Ala Val Lys Val Leu Gly Ala Asp Gly Ser
        195                 200                 205

Gly Gln Tyr Ser Trp Ile Ile Asn Gly Ile Glu Trp Ala Ile Ala Asn
    210                 215                 220

Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
                245                 250                 255

Val Ala Ala Ala Gly Asn Glu Gly Thr Ser Gly Ser Ser Ser Thr Val

|     |     | 260 |     |     |     |     | 265 |     |     |     |     | 270 |     |     |     |
| --- | --- | --- | --- | --- | --- | --- | --- | --- | --- | --- | --- | --- | --- | --- | --- |
| Gly | Tyr | Pro 275 | Gly | Lys | Tyr | Pro | Ser 280 | Val | Ile | Ala | Val | Gly 285 | Ala | Val | Asp |
| Ser | Ser 290 | Asn | Arg | Ala | Ser | Phe 295 | Ser | Ser | Val | Gly | Pro 300 | Glu | Leu | Asp | Val |
| Met 305 | Ala | Pro | Gly | Val | Ser 310 | Ile | Gln | Ser | Thr | Leu 315 | Pro | Gly | Asn | Lys | Tyr 320 |
| Gly | Ala | Tyr | Asn | Gly 325 | Thr | Ser | Met | Ala | Ser 330 | Pro | His | Val | Ala | Gly 335 | Ala |
| Ala | Ala | Leu | Ile 340 | Leu | Ser | Lys | His | Pro 345 | Asn | Trp | Thr | Asn | Thr 350 | Gln | Val |
| Arg | Ser | Ser 355 | Leu | Glu | Asn | Thr | Thr 360 | Thr | Lys | Leu | Gly | Asp 365 | Ser | Phe | Tyr |
| Tyr | Gly 370 | Lys | Gly | Leu | Ile | Asn 375 | Val | Gln | Ala | Ala | Ala 380 | Gln |     |     |     |

( 2 ) INFORMATION FOR SEQ ID NO:13:

( i ) SEQUENCE CHARACTERISTICS:
( A ) LENGTH: 11 amino acids
( B ) TYPE: amino acid
( D ) TOPOLOGY: linear ( x i ) SEQUENCE DESCRIPTION: SEQ ID NO:13:

|     |     |     |     |     |     |     |     |     |     |     |
| --- | --- | --- | --- | --- | --- | --- | --- | --- | --- | --- |
| Ala 1 | Glu | Pro | Xaa | Ala 5 | Val | Asp | Ile | Asp | Arg 10 | Leu |